(12) United States Patent
Zimmer et al.

(10) Patent No.: US 9,890,407 B2
(45) Date of Patent: Feb. 13, 2018

(54) METHOD FOR SYNTHESIZING CELLULOSE IN VITRO

(71) Applicants: University of Virginia Patent Foundation, Charlottesville, VA (US); Jochen Gottfried Zimmer, Charlottesville, VA (US); Jacob Lowell Whitten Morgan, Colorado Springs, CO (US)

(72) Inventors: Jochen Gottfried Zimmer, Charlottesville, VA (US); Jacob Lowell Whitten Morgan, Colorado Springs, CO (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/027,238

(22) PCT Filed: Oct. 3, 2014

(86) PCT No.: PCT/US2014/058952
§ 371 (c)(1),
(2) Date: Apr. 4, 2016

(87) PCT Pub. No.: WO2015/051203
PCT Pub. Date: Apr. 9, 2015

(65) Prior Publication Data
US 2016/0244796 A1    Aug. 25, 2016

Related U.S. Application Data

(60) Provisional application No. 61/886,411, filed on Oct. 3, 2013.

(51) Int. Cl.
| | | |
|---|---|---|
| *C12N 9/10* | (2006.01) | |
| *C12P 19/04* | (2006.01) | |
| *C12P 19/18* | (2006.01) | |

(52) U.S. Cl.
CPC ............ *C12P 19/04* (2013.01); *C12N 9/1059* (2013.01); *C12P 19/18* (2013.01); *C07K 2299/00* (2013.01); *C12Y 204/01012* (2013.01)

(58) Field of Classification Search
None
See application file for complete search history.

(56) References Cited

U.S. PATENT DOCUMENTS

| | | | | |
|---|---|---|---|---|
| 5,268,274 A | * | 12/1993 | Ben-Bassat | C07K 14/195 435/101 |
| 5,382,656 A | * | 1/1995 | Benziman | C12N 9/1059 435/194 |
| 6,541,238 B1 | * | 4/2003 | Saxena | C12N 9/1059 435/193 |
| 2002/0129401 A1 | * | 9/2002 | Stalker | C12N 9/1059 800/278 |

OTHER PUBLICATIONS

Omadjela O. et al. BcsA and BcsB Form the Catalytically Active Core of Bacterial Cellulose Synthase Sufficient for In vitro Celllose Synthesis. PNAS 110(44)17856-61, Oct. 29, 2013.*
Morgan J. et al. Crystallographic Snapshot of Cellulose Synthesis and Membrane Translocation. Nature 493(7431)181-187, Jan. 10, 2013.*

* cited by examiner

*Primary Examiner* — Ralph J Gitomer
(74) *Attorney, Agent, or Firm* — Rodney L. Sparks

(57) ABSTRACT

Disclosed herein is in vitro cellulose synthesis reconstituted from purified BcsA and BcsB proteins from *Rhodobacter sphaeroides*. Further disclosed is that BcsB is essential for catalysis by BcsA. The purified BcsA-B complex produces cellulose chains of a degree of polymerization in the range 200-300. Catalytic activity of native proteins depends on the presence of cyclic-di-GMP, but is independent of lipid-linked reactants. Further disclosed is strict substrate specificity of cellulose synthase for UDP-glucose. Truncation analysis of BcsB localized the region required for activity of BcsA within its C-terminal membrane-associated domain. Further disclosed are crystal structures of the cyclic-di-GMP-activated BcsA-B complex revealing that cyclic-di-GMP releases an auto-inhibited state of the enzyme by breaking a salt bridge which otherwise tethers a conserved gating loop that controls access to and substrate coordination at the active site. Unexpectedly, disrupting the salt bridge by mutagenesis generates a constitutively and fully active cellulose synthase.

20 Claims, 39 Drawing Sheets
(21 of 39 Drawing Sheet(s) Filed in Color)

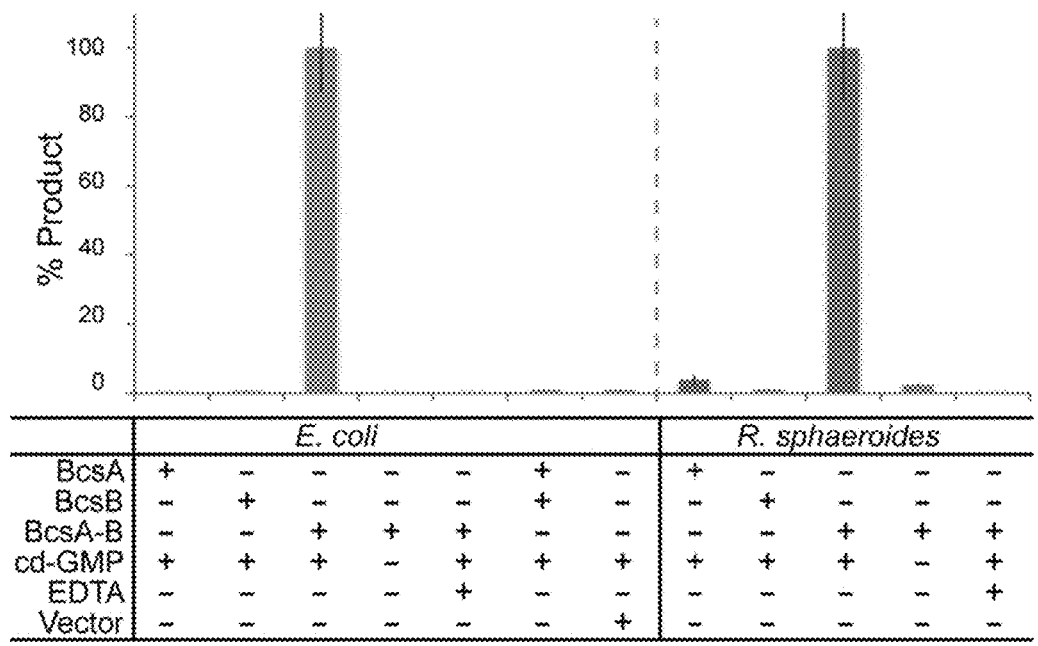
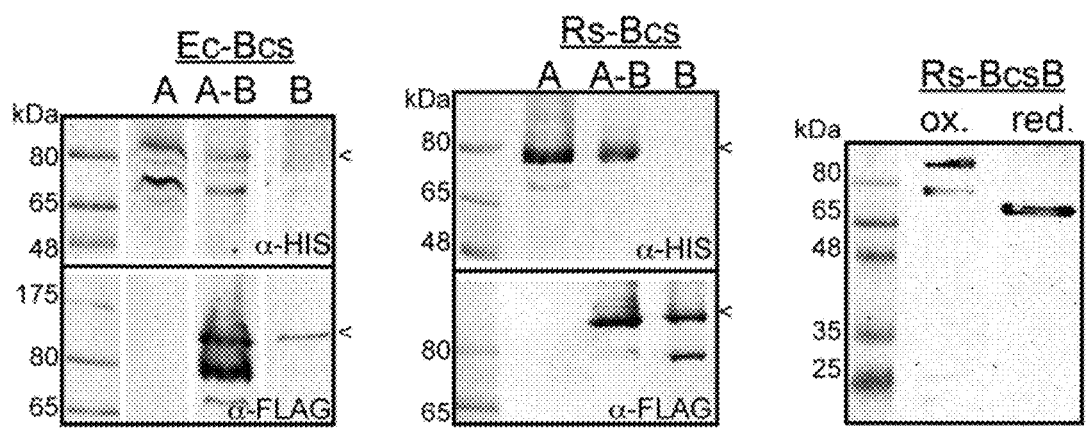
FIG. 1B
FIG. 1C

FIG. 18A   FIG. 18B

```
                              Gating Loop
                         IF3
R. sphaeroides    492  VTTLLRPRSARFAVTAKDETLSENYI
G. xylinus        463  FVTLLAPHKGKFNVTDKGGLLDRERF
R. leguminosarum  491  VSVMLNPRKPTFKVTAKDESIAVSRL
E. coli           606  LVALINPHKGKFNVTAKGGLVEEEYV
A. aeolicus       503  ILTLLNPKNPTFRVTPKGELLDRDYI
C. difficile      425  ILETFAISKNKFSVTNKSKLEENRMY
P. patens         960  LLKVFAGIDTNFTVTSKQAEDEDFAE
A. thaliana       943  LLKVLAGIDTNFTVTSKATDEDGDFA
O. sativa         955  LLKVIAGIDTSFTVTSKGGDDEEFSE
Z. mays           940  FLKVLGGVDTSFTVTSKAAGDEADAF
P. trichocarpa    946  LLKVLAGIDTNFTVTSKASDEDGDFA
```

FIG. 21A

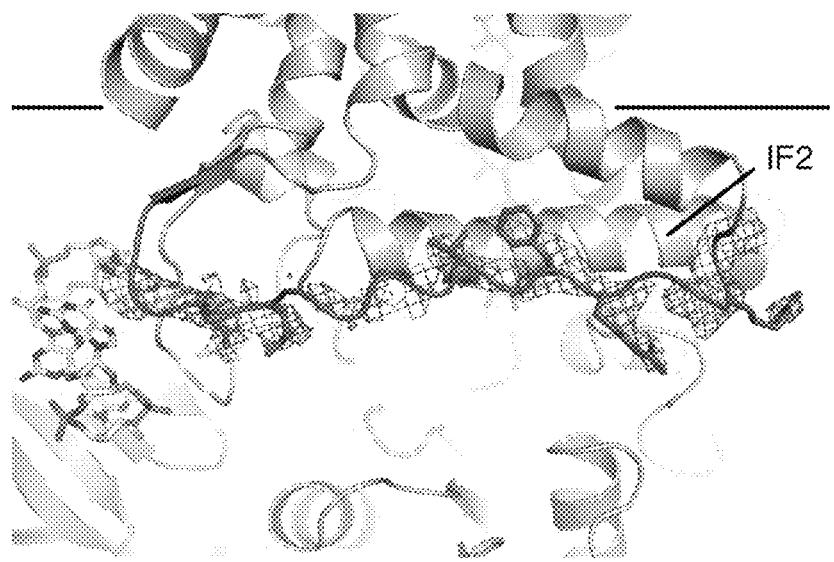

FIG. 21B

|  |  |  |
|---|---|---|
| R. sphaeroides | 334 | GFAGETITEDAETALEIHSRGW |
| G. xylinum | 305 | GFATETVTEDAHTALRMQRQGW |
| R. leguminosarum | 333 | GFSGISITEDCETALALHGSGW |
| E. coli | 448 | GIAVETVTEDAHTSLRLHRRGY |
| A. aeolicus | 345 | GIQTTTVTEDAETALELHSRGY |
| C. difficile | 267 | GFYTYSITEDFATGILIQSKGY |
| P. patens | 784 | GWIYGSVTEDILTGFKMHCRGW |
| A. thaliana | 771 | GWIYGSVTEDILTGFKMHARGW |
| O. sativa | 783 | GWIYGSVTEDILTGFKMHCHGW |
| Z. mays | 768 | GWIYGSVTEDILTGFKMHCRGW |
| P. trichocarpa | 774 | GWIYGSVTEDILTGFKMHARGW |

(Small Loop / Finger Helix)

FIG. 24A

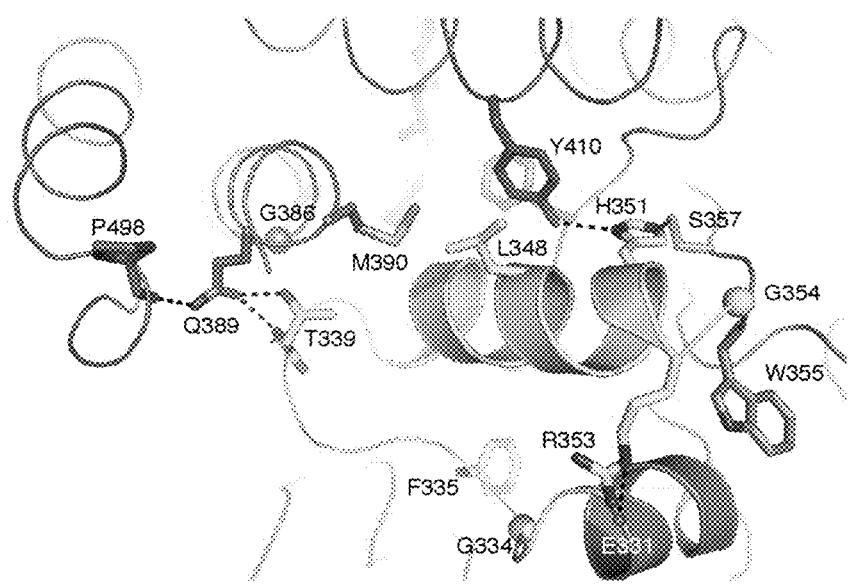

FIG. 24B

METHOD FOR SYNTHESIZING CELLULOSE IN VITRO

CROSS REFERENCE TO RELATED APPLICATIONS

This application is a National Stage application filed under Rule 371 based upon PCT/US14/58952 filed Oct. 3, 2014 which is a national stage filing of International Application No. PCT/US2014/058952, filed Oct. 3, 2014, which claims benefit of priority pursuant to 35 U.S.C. § 119(e) to U.S. provisional patent application No. 61/886,411, filed on Oct. 3, 2013. The entire disclosures of the afore-mentioned patent applications are incorporated herein by reference.

STATEMENT REGARDING FEDERALLY SPONSORED RESEARCH OR DEVELOPMENT

This invention was made with government support under Grant Nos. GM101001, awarded by The National Institutes of Health. The government has certain rights in the invention.

BACKGROUND

Polysaccharides are essential biopolymers performing diverse biological functions, ranging from energy storage to osmoregulation and cell wall formation. Extracellular polysaccharides, including cellulose, chitin, and alginate, are synthesized inside the cell from nucleotide-activated sugars and are transported across the cell membrane during their synthesis. This remarkable task is performed by membrane-integrated glycosyltransferases (GT) that couple polymer elongation with translocation (1, 2). Cellulose is the most abundant biopolymer on earth primarily formed by vascular plants, but also by some bacteria. Bacterial extracellular polysaccharides, such as cellulose and alginate, are an important component of biofilms, which are multi-cellular, usually sessile, aggregates of bacteria. Biofilms exhibit a greater resistance to antimicrobial treatments compared to isolated bacteria and thus are a particular concern to human health.

Cellulose is a linear polymer of glucose molecules linked via β-1,4 glycosidic linkages (3, 4) and is primarily formed by vascular plants, but also by some algae, protists, and bacteria (4-6). Cellulose is synthesized by cellulose synthase (CesA), a family 2 member of GT (7) that processively polymerizes UDP-activated glucose via an evolutionarily conserved mechanism (2). CesAs contain eight predicted transmembrane (TM) segments and at least one extended intracellular domain adopting a GT-A fold (2, 8). The intracellular GT-A domain is responsible for donor and acceptor sugar binding as well as for catalyzing the GT reaction and the membrane-embedded part forms a TM pore in close juxtaposition with the catalytic site, thereby allowing translocation of the nascent polysaccharide (2).

While most eukaryotic CesAs are believed to form supramolecular complexes that organize the secreted glucans into cable-like structures, i.e. the cellulose microfibrils (9), many Gram-negative bacteria synthesize cellulose as a biofilm component (10, 11). Biofilm formation is stimulated by the bacterial messenger cyclic-di-GMP (c-di-GMP) (12), which affects a diverse group of enzymes via interaction with either covalently or non-covalently attached c-di-GMP-binding domains, such as PilZ (13-15).

Bacterial cellulose synthase (Bcs) is a multi-component protein complex encoded in an operon containing at least 3 genes, bcsA, -B and -C (16, 17). While BcsA is the catalytic subunit that synthesizes cellulose and forms the TM pore across the inner membrane, BcsB is a large periplasmic protein that is anchored to the inner membrane via a single C-terminal TM helix. BcsB may guide the polymer across the periplasm towards the outer membrane via two carbohydrate-binding domains (CBD) (2). BcsA and BcsB are fused into a single polypeptide chain in some species (18). BcsC is predicted to form a β-barrel in the outer membrane, preceded by a large periplasmic domain containing tetratricopeptide repeats likely involved in complex assembly (16). Most cellulose synthase operons also code for a periplasmic cellulase, BcsZ, whose biological function is unknown, yet it appears to enhance cellulose production in vivo (19, 20). While most biofilm-forming bacteria likely produce amorphous cellulose that is embedded in a 3-dimensional matrix of polysaccharides, proteinaceous fibers and nucleic acids (21), some bacteria produce cellulose microfibrils resembling those synthesized by eukaryotic cells (22). In such bacteria, CesA complexes are linearly arranged along the cell axis and the CesA operons encode at least one additional subunit, BcsD, that might facilitate the linear organization of the synthases (18).

Despite the numerous studies available on a large number of pro- and eukaryotic model systems, revealing the mechanism of cellulose synthesis and translocation has been hampered by difficulties in reconstituting functional cellulose synthases in a purified system, either from eukaryotic or prokaryotic enzymes (23-26). To date, cellulose biosynthetic activities have only been recovered from detergent extracts of native membranes (24-26).

There is a long felt need in the art for compositions and methods useful making cellulose in an acellular manner. The present invention satisfies these needs.

SUMMARY OF THE INVENTION

Despite numerous attempts, reconstituting cellulose synthesis in vitro from purified components has been difficult. However, disclosed herein is the complete reconstitution of bacterial cellulose synthesis from components from *Rhodobacter sphaeroides*, thereby establishing an experimental basis for cellulose and biofilm research. The present application discloses for the first time reconstitution of cellulose synthesis in vitro based on the recovery of cellulose synthase activity from purified bacterial components.

To overcome these challenges, an active cellulose synthetic system was reconstituted in vitro from a purified *Rhodobacter sphaeroides* BcsA-B complex. It is disclosed herein that the purified complex efficiently synthesizes amorphous, high molecular weight (HMW) cellulose upon incubation with UDP-Glc and c-di-GMP, both in a detergent-solubilized state as well as after reconstitution into proteoliposomes (PLs). It is further disclosed that cellulose elongation occurs directly from UDP-Glc without lipid-linked intermediates, that c-di-GMP activates the synthase, and a strict substrate specificity of BcsA for UDP-Glc. Furthermore, it was unexpectedly found that BcsB is crucial for the catalytic activity of BcsA.

Truncation analysis of BcsB disclosed herein localized the region required for activity of BcsA within its C-terminal membrane-associated domain. Further disclosed are crystal structures of the cyclic-di-GMP-activated BcsA-B complex revealing that cyclic-di-GMP releases an auto-inhibited state of the enzyme by breaking a salt bridge which otherwise tethers a conserved gating loop that controls access to and substrate coordination at the active site. It is further disclosed herein that, unexpectedly, disrupting the salt bridge by mutagenesis generates a constitutively active cellulose synthase.

In one embodiment, the present invention provides methods useful for synthesizing cellulose using purified bacterial components and reconstituting the synthesis in vitro or in another cell. In one aspect, the method comprises adding BcsA, or a biologically active fragment or homolog thereof, reconstituted into a membrane mimetic, and BcsB, or a biologically active fragment or homolog thereof, to a mixture of uridine diphosphate glucose (UDP-Glc), a divalent cation, optionally dimeric guanosine monophosphate (c-di-GMP), and a physiological buffer, thereby synthesizing cellulose. In one aspect, the membrane mimetic is part of the composition into which BcsA or a BcsA-B complex is added.

In one embodiment, the present invention provides compositions for synthesizing cellulose using purified bacterial components and reconstituting the synthesis in vitro or in another cell. In one aspect, the compositions comprise purified BcsA, or a biologically active fragment or homolog thereof, purified BcsB, or a biologically active fragment or homolog thereof, UDP-Glc, a divalent cation, optionally c-di-GMP, a membrane mimetic, and a physiologic buffer.

In one embodiment, the present invention provides an expression vector or plasmid comprising a nucleic acid sequence encoding BcsA protein, or a biologically active fragment or homolog thereof and optionally encoding BcsB protein, or a biologically active fragment or homolog thereof. In one aspect, when the vector does not encode BcsB, the invention provides a second vector or plasmid encoding BcsB, or a biologically active fragment or homolog thereof.

In one embodiment, the present invention provides a host cell for synthesizing cellulose, wherein the cell comprises an expression vector comprising a nucleic acid sequence encoding BcsA protein, or a biologically active fragment or homolog thereof and optionally encoding BcsB protein, or a biologically active fragment or homolog thereof. In one aspect, when the vector does not encode BcsB, said cell comprises a second vector encoding BcsB.

In one embodiment, the host cell is a recombinant cell. In one aspect, the host cell does not express endogenous BcsA or BcsB. In one aspect, it does not express other cellulose synthases. In one aspect, the host cell does not have endogenous BcsA or BcsB genes.

The present invention further provides cellulose synthesized using the compositions and methods of the invention. In one aspect, it is high molecular weight cellulose. In one aspect, it is amorphous cellulose.

In one aspect, one or more nucleic acids encoding BcsA and BcsB, or biologically active fragments or homologs thereof, are used for transforming a host cell. In one aspect, cellulose synthesis occurs in the host cell. In one aspect, the cell is an *E. coli* or other bacteria.

The present application discloses the surprising result of the strict dependence of BcsA's catalytic activity on BcsB.

The present invention provides compositions and methods for synthesizing cellulose using purified bacterial components. In one aspect, the components are purified bacterial cellulose synthases A and B (BcsA and BcsB).

In one aspect, BcsA and BcsB are purified separately and then combined to form a complex. In another aspect, BcsA and BcsB are purified together as a complex.

In one aspect, BcsB interaction with BcsA is essential for catalysis. In one aspect, the membrane domain of BcsB is essential for cellulose synthesis. In one aspect, only the C-terminal membrane-associated region of BcsB is required for function, i.e., catalytic activity, although it does not directly contribute to forming the active site or translocation channel. In another aspect, residues 684-725 (C-terminal region) of BcsB (SEQ ID NO:3 or equivalent hybrid or other species) suffice to mediate the interaction with BcsA and maintain the catalytic activity of BcsA.

In one aspect, the purified BcsA-B complex produces high molecular weigh cellulose.

The present application discloses the unexpected result that the cellulose synthase complex is functional as a monomeric BcsA-B complex, not as a BcsA-B dimer, tetramer, etc. The result is surprising because previous models proposed that cellulose synthases must form at least dimers to function. It is further disclosed herein that the outer membrane component is not required for catalysis, nor is the periplasmic cellulase BcsZ.

In vivo, BcsA and BcsB must be synthesized as individual proteins, which assemble after they have been incorporated into the cell membrane. Based on the results disclosed herein, it is hypothesized that complex formation occurs before cellulose synthesis; however, without wishing to be bound by any particular theory it is further hypothesized that BcsA starts to produce cellulose and the presence of the polymer stabilizes the interaction with BcsB (this would require that there is sufficient residual activity of BcsA to produce a short polymer without BcsB).

In one aspect, BcsA and BcsB are purified before being added to the other components of the cellulose synthesis composition. In one aspect, BcsA and BcsB are purified as a complex. In another aspect, BcsA and BcsB are purified separately.

In one embodiment, cellulose synthesis is performed in vitro. In one aspect, some cellular components such as inverted membranes can be used in a composition of the invention.

In one aspect, a membrane mimetic is part of the composition. Membrane mimetics include, but are not limited to, detergent micelles, lipid vesicles, and planar lipid bilayers. In one aspect, the planar lipid bilayer is native. In another aspect, it is synthetic.

In one aspect, one component of a composition of the invention is a physiologic buffer. One of ordinary skill in the art will appreciate that different buffers can be used based on the disclosure and teachings herein. In one aspect, the buffer has a pH of about 6.5 to about 9.5. In one aspect, the buffer has a pH of about 7.5. In one aspect, the buffer comprises a salt. In one aspect the salt is NaCl. In one aspect, NaCl is used at 100 mM.

In one aspect, UDP-Glc is a component of the composition. One of ordinary skill in the art will appreciate that depending on the conditions and components being used the final concentration of UDP-Glc being used can vary. In one aspect, a final concentration of about 2 mM UDP-Glc is used.

In one aspect, a protein stabilizer can be added to the composition. In one aspect, glycerol can be used. In one aspect, about 10% glycerol is used as a protein stabilizer.

One of ordinary skill in the art will appreciate that the temperature of the incubation can vary, but in one aspect, the incubation is done at 37° C.

In one aspect, at least one divalent cation is added to the composition. Useful divalent cations of the invention include, but are not limited to, $Mn^{2+}$ and $Mg^{2+}$. In one aspect, the divalent cation is used at a concentration of 20 mM.

The composition of the present invention can be prepared and used without added lipid-linked reactants.

The entire BcsB protein (SEQ ID NO:3 or 5) can be used in the compositions and methods of the invention. The protein can be obtained from any species. Additionally, fragments from different species can be combined and can be used as a hybrid (see SEQ ID NO:5), particularly if the protein to be isolated is synthesized in a cell that needs a particular leader sequence. In one aspect, a biologically active homolog or fragment of BcsB can be used. For example, fragments of BcsB with the desired activity include fragments comprising amino acid residues 190-725, 309-725, 456-725, and 684-725 (SEQ ID NO:4). Equivalent fragments of BcsB protein from other species can be used as well.

In one embodiment, the BcsB protein, or a biologically active fragment or homolog thereof, mediates interaction with BcsA. In one aspect, it maintains the catalytic activity of BcsA.

In one embodiment, BcsA comprises an amino acid sequence having SEQ ID NOs:1 or 2, or a biologically active fragment or homolog thereof. In one aspect, BcsA comprises one or more mutations. In one aspect, BcsA, or a biologically active fragment or homolog thereof, comprises a mutation at position 580 (of SEQ ID NO:1) replacing arginine with alanine. In one aspect, the position 580 mutation confers constitutive catalytic activity to BcsA, or a biologically active fragment or homolog thereof. In one aspect, when a mutant BcsA is constitutively active, no c-di-GMP is required in the composition of the invention. The invention further includes the use of BcsA proteins or fragments from multiple species, including *Rhodobacter sphaeroides* and *E. coli*. When other species are used the site of the mutation may vary from position 580, but will still be at the first R of the RxxxR motif as described herein. In one aspect, BcsA, or a biologically active fragment or homolog thereof, comprises a mutation at position 371 replacing glutamic acid with alanine. In one aspect, the mutation at position 371 increases the catalytic activity of BcsA. When a BcsA other than from *Rhodobacter sphaeroides* is used, the glutamic acid to alanine replacement may not be at position 371, but can be determined by one of ordinary skill in the art.

In one embodiment, the bacterial cellulose synthases (A and B) are from *Rhodobacter sphaeroides*. In one aspect, the bacterial cellulose synthases (A and B) are from other bacteria comprising the bacterial cellulose synthases (A and B), including *E. coli*.

In one embodiment, the present invention provides compositions and methods for analyzing the salt bridge described herein and for mutating residues to generate a constitutively active enzyme as disclosed herein. One of ordinary skill in the art will be able to use this method on cellulose synthase A derived from other bacteria.

In one embodiment, the method provides for the synthesis of high molecular weight cellulose. In one aspect, the method provides for the synthesis of cellulose chains with a degree of polymerization of at least about 200. In one aspect, the method provides for the synthesis of cellulose chains with a degree of polymerization in the range of about 200-300. In one aspect, the cellulose comprises 1,4-linked glucosyl residues.

The synthesis of cellulose as disclosed herein has many potential uses, including, for example, the synthesis of biofilms.

In one embodiment, in the reconstituted bacterial cellulose synthesis composition of the invention, the activator c-di-GMP stimulates cellulose synthesis. One of ordinary skill in the art will appreciate that the concentration used can vary depending on the conditions of the synthesis, the amount of other ingredients used, etc. In one aspect, c-di-GMP is used at a final concentration of 0.3 µM.

One of ordinary skill in the art will appreciate that UDP-glc can be used at varying concentrations depending on the amounts of the other components being used and the conditions of the incubation. In one aspect, UDP-glc is used at a final concentration of 2.0 mM.

The present invention discloses that BcsA and BcsB are the sole Bcs proteins required for cellulose synthesis. It was previously thought that the native bacterial cellulose synthase complex is a multi-subunit complex that spans the inner and outer bacterial membrane. However, it is disclosed herein that the inner membrane components are sufficient to synthesize and transport cellulose across the inner membrane. It is further disclosed herein that, contrary to previous models suggesting that the cellulose synthases must form a multimeric complex such as a dimer, trimer, etc., the cellulose synthase complex is instead functional as a monomeric BcsA-B complex. Furthermore, BcsB is required for catalytic activity of BcsA, although it does not directly contribute to forming the active site or translocation channel. Therefore, in one aspect of the invention, BcsA and BcsB form a complex, wherein BcsB is required for BcsA catalytic activity.

The present invention further provides for the synthesis of cellulose using only BcsA and BcsB, in the absence of other synthase subunits. Therefore, BcsZ is not required for the synthesis disclosed herein and is not needed in the composition of the invention.

In one aspect, synthesis can be performed using proteoliposomes or nanodiscs.

Some Useful Sequences of the Invention—

In addition to the sequences summarized below, various fragments are also described herein based on their residue positions relative to the mature protein.

```
                                              SEQ ID NO: 1
Rhodobacter sphaeroides BcsA- (GenBank accession
number ABA79509.1; 788 amino acid residues)
mtvrakarsplrvvpvllfllwvallvpfgllaaapvapsaqglialsav vlvallkpfadkmvprflllsaasmlvmrywfwrlfetlpppaldasflf alllfavetfsisifflngflsadptdrpfprplqpeelptvdilvpsyn epadmlsvtlaaaknmiyparlrtvvlcddggtdqrcmspdpelaqkaqe rrrelqqlcrelgvvystrernehakagnmsaalerlkgelvvvfdadhv psrdflartvgyfvedpdlflvqtphffinpdpiqrnlalgdrcppenem fygkihrgldrwggaffcgsaavlrrraldeaggfagetitedaetalei hsrgwkslyidramiaglqpetfasfiqqrgrwatgmmqmlllknplfrr glgiaqrlcylnsmsfwffplvrmmflvapliylffgieifvatfeevla ympgylavsflvqnalfarqrwplvsevyevaqapylaraivttllrprs arfavtakdetlsenyispiyrpllftfllclsgvlatlvrwvafpgdrs vllvvggwavlnvllvgfalravaekqqrraaprvqmevpaeaqipafgn rsltatvldastsgvrllvrlpgvgdphpaleaggliqfqpkfpdapqle rmvrgrirsarreggtvmvgvifeagqpiavretvaylifgesahwrtmr
```

-continued eatmrpigllhgmarilwmaaaslpktardfmdeparrrrrheepkekqa hllafgtdfstepdwagelldptaqvsarpntvawgsn SEQ ID NO: 2
Rhodobacter sphaeroides BcsA with His Tags (803
amino acid residues)-
mgtvrakarsplrvvpvllfllwvallvpfgllaaapvapsaqglialsa vvlvallkpfadkmvprflllsaasmlvmrywfwrlfetlpppaldasfl falllfavetfsisifflngflsadptdrpfprplqpeelptvdilvpsy nepadmlsvtlaaaknmiyparlrtvvlcddggtdqrcmspdpelaqkaq errrelqqlcrelgvvystrernehakagnmsaalerlkgelvvvfdadh vpsrdflartvgyfvedpdlflvqtphffinpdpiqrnlalgdrcppene mfygkihrgldrwggaffcgsaavlrrraldeaggfagetitedaetale ihsrgwkslyidramiaglqpetfasfiqqrgrwatgmmqmlllknplfr rglgiaqrlcylnsmsfwffplvrmmflvapliylffgieifvatfeevl aympgylavsflvqnalfarqrwplvsevyevaqapylaraivttllrpr sarfavtakdetlsenyispiyrpllftfllclsgvlatlvrwvafpgdr svllvvggwavlnvllvgfalravaekqqrraaprvqmevpaeaqipafg nrsltatvldastsgvrllvrlpgvgdphpaleaggliqfqpkfpdapql ermvrgrirsarreggtvmvgvifeagqpiavretvaylifgesahwrtm reatmrpigllhgmarilwmaaaslpktardfmdeparrrrrheepkekq ahllafgtdfstepdwagelldptaqvsarpntvawgsnhhhhhhklhhh hhh SEQ ID NO: 3
Rhodobacter sphaeroides BcsB- (GenBank accession
number ABA79508.1; 725 amino acid residues; the
underlined portion is the sequence of SEQ
ID NO: 4)
mdmrllpflflgtlasmaaaqdapmivieglteeepqaspdavaeavpaa evapwiiplrplaetaqvgplfrlqgqqaraafrlflpteavggtltlaq rssidilpessqiivrmndqeigrftprqfgalgavtmplgeavragdnl vtieaqhrhriycgadaefdlwtevdlsqsgvalpaaaigteptsfiaal taqaesgrpveirtptppdeatlrtlaqalgrplpdealplalskpwsae tgptyaritllpsdadrvsirrggdgavvlvlehppegspnaslvadllg atptlpppt1pqippgrvvtladmgvdtiltdnryfnrdidfqlpddwll lasqkaqigidygfagglpegalllvkvngttvrmlpldrdaapvkprld irfparllhpgpnrlsfesvipgnppdqpcpasagdlmqvlsstdlevpp sprmqmadmardlaqvtpasvhpatpdglartlpfmaafrevpdaapvdl tvaglhdiatvplneegltprllaltllpstvsrlverpatpagppanal aplgaapgegvmpplvesnwsdraqtfvqatlqpviqtvrrmlrpgdgnl aewlatrkgtamllapepgklwvilgpeaeparvaealamaprspggprg qvavlgsdgrwsswskpgllpelrepvsldnvr<u>svvgnvasarpplllgg mlglawisaaiavgfvlrtrrkglk</u>

SEQ ID NO: 4
Residues 684-725 of Rhodobacter sphaeroides BcsB
(SEQ ID NO: 3)
<u>svvgnvasarpplllggmlglawisaaiavgfvlrtrrkglk</u>

SEQ ID NO: 5
a hybrid BcsB molecule comprising a 24 amino acid
leader sequence (underlined) of E. coli replacing
the 20 amino acid leader sequence of the N-
terminus of Rhodobacter sphaeroides BcsB (SEQ ID
NO: 3), resulting in a protein of 729 amino
acid residues.
<u>mkyllptaaaqllllaaqpamamqq</u>dapmivieglteeepqaspdavaea vpaaevapwiiplrplaetaqvgplfrlqgqqaraafrlflpteavggtl tlaqrssidilpessqiivrmndqeigrftprqfgalgavtmplgeavra gdnlvtieaqhrhriycgadaefdlwtevdlsqsgvalpaaaigteptsf iaaltaqaesgrpveirtptppdeatlrtlaqalgrplpdealplalskp wsaetgptyaritllpsdadrvsirrggdgavvlvlehppegspnaslva dllgatptlppptlpqippgrvvtladmgvdtiltdnryfnrdidfqlpd dwlllasqkaqigidygfagglpegalllvkvngttvrmlpldrdaapvk prldirfparllhpgpnrlsfesvipgnppdqpcpasagdlmqvlsstdl evppsprmqmadmardlaqvtpasvhpatpdglartlpfmaafrevpdaa pvdltvaglhdiatvplneegltprllaltllpstvsrlverpatpagpp analaplgaapgegvmpplvesnwsdraqtfvqatlqpviqtvrrmlrpg dgnlaewlatrkgtamllapepgklwvilgpeaeparvaealamaprspg gprgqvavlgsdgrwsswskpgllpelrepvsldnvrsvvgnvasarppl llggmlglawisaaiavgfvlrtrrkglk Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Example 1

FIG. 1A-1C (also referred to as Example 1, FIG. 1): BcsA and BcsB are necessary for cellulose synthesis. (FIG. 1A) Inverted membrane vesicles containing either BcsA, BcsB, or both subunits were incubated for 60 min at 37° C. in the presence and absence of c-di-GMP and 0.25 μCi UDP-[³H]-Glc. The synthesized polymer was purified by descending paper chromatography and quantified by scintillation counting. The amount of product obtained is shown relative to the product formed from IMVs containing BcsA and BcsB. Control reactions were performed with IMVs derived from cells containing an empty pET28a vector or in the absence of c-di-GMP or the presence of 20 mM EDTA. Results are shown in light and dark gray for components from Ec and Rs, respectively. (FIG. 1B) immuno-blotting of IMVs containing BcsA and BcsB. BcsA and BcsB were expressed with C-terminal poly-histidine- and FLAG-tags, respectively, and the equivalent amounts of IMVs used for activity assays were analyzed under non-reducing conditions by western blotting. Full length BcsA migrates close to the 80 kDa molecular weight marker while BcsB runs close to 100 kDa. The full-length proteins are indicated by arrowheads. (FIG. 1C) Western analysis of oxidized and reduced BcsB. IMVs containing Rs BcsB were solubilized in 2% SDS and incubated with 20 mM DTT prior to SDS-PAGE.

(FIG. 2A) PLs containing 1 µM of purified Rs BcsA-B complex were incubated at 37° C. for the indicated time in the presence and absence of c-di-GMP and the synthesized polymer was quantified as described in FIGS. 1A-1C. The polymer is degraded by endo-β-1,4- but not by endo-β-1,3 glucanase. Inset: Coomassie stained SDS-PAGE of reconstituted BcsA-B. (FIG. 2B) Characterization of the BcsA-B in vitro product by linkage analysis (see experimental details in SI Materials and Methods). Shown is a typical gas chromatogram corresponding to the separated permethylated alditolacetates. The derivative corresponding to terminal glucose residues (non-reducing ends; t-Glc) was quantified from multiple chromatograms obtained from different dilutions of the alditolacetates and represents no more than 0.3-0.5% of the total alditolacetates. The only other peak in the chromatogram arising from a sugar residue corresponds to 1,4-linked glucosyl residues (1,4-Glc) and represents 99.5-99.7% of the total derivatives. See FIG. 8 for verification of the alditolacetates identity by electron-impact mass spectrometry.

(FIG. 3A) Cellulose synthesis reactions were performed in the presence of IU PK and LDH, 0.5 mM NADH and 1 mM PEP. The LDH-catalyzed oxidation of NADH to $NAD^+$ was monitored spectrophotometrically at 340 nm. Control reactions in the absence of UDP-Glc, c-di-GMP, PEP or BcsA-B do not lead to oxidation of NADH. Addition of 1 mM UDP to the reaction rapidly depletes NADH by circumventing cellulose synthesis. (FIG. 3B and FIG. 3C) Titration of UDP-Glc and c-di-GMP. Apparent reaction rates at a constant c-di-GMP concentration of 30 µM and increasing UDP-Glc concentrations (FIG. 3B) or increasing concentrations of c-di-GMP at a constant UDP-Glc concentration of 5 mM (FIG. 3C). The data were fit to monophasic Michaelis-Menten kinetics. $K_m$ and $K_A$ are the apparent affinities for the substrate UDP-Glc and the activator c-di-GMP, respectively. (FIG. 3D) Titration of UDP-Glc from 0 to 7.5 mM at the indicated c-di-GMP concentrations. All reactions were performed at room temperature with 0.5 µM ND-reconstituted BcsA-B in a total volume of 20 µl.

(FIG. 4A) Enzyme-coupled cellulose synthesis assays were performed as described in FIG. 3 in the absence or presence of 0.1 mg/ml E. coli BcsZ. Control reactions in the absence of c-di-GMP do not lead to a significant depletion of NADH. Inset: Radioactive sedimentation assay performed with ND-reconstituted BcsA-B synthesizing cellulose in the absence or presence of BcsZ. (FIG. 4B) Inhibition of cellulose synthesis by UDP. Cellulose synthesis sedimentation assays were performed with 1 µM PL-reconstituted BcsA-B in the presence of increasing concentrations of the indicated nucleotides and 0.5 mM UDP-Glc for 60 min at 37° C. The obtained product is quantified relative to the polymer formed in the absence of any nucleoside diphosphate. (FIG. 4C) UDP is a competitive inhibitor of cellulose synthase. Cellulose synthesis sedimentation assays performed (as in FIG. 4B) in the presence of 0.7 mM UDP and increasing concentrations of UDP-Glc. The products are quantified relative to the polymer formed in the absence of UDP and the presence of 5 mM UDP-Glc.

(FIG. 5A) Enzyme-coupled cellulose synthase assays performed with 0.5 µM PLs-reconstituted BcsA-B in the presence of 5 mM of the indicated substrates. The apparent activities are expressed relative to the activity in the presence of UDP-Glc. (FIG. 5B) Inhibition of cellulose synthesis by alternative substrates. Activity assays were performed for 90 min at 37° C. in the presence of 1 mM UDP-Glc and increasing concentrations of UDP-Xyl, -Gal, or -NAG. The apparent rates are shown relative to the activity in the presence of 1 mM UDP-Glc only. (FIG. 5C) As in (FIG. 5B) but shown are the linear decreases in absorbance at 340 nm for samples incubated with 1 mM UDP-Glc and the indicated concentrations of UDP-Xyl. (FIG. 5D) BcsA-B is catalytically active in a detergent-solubilized state. As in a membrane-reconstituted state, cellulose synthesis is activated by c-di-GMP and the HMW product is degraded by endo β-1,4 glucanase (β-1,4).

(FIG. 6A) The multi-domain BcsB protein forms, from the N- to the C-terminus, two repeats of a carbohydrate-binding domain (CBD) linked to a flavodoxin-like domain (FD). N-terminal truncation mutants were designed to progressively truncate BesS. The TM and cytosolic domains of BcsA are shown as a surface in dark and light gray, respectively, and the translocating glucan is shown as red spheres. Horizontal bars indicate the putative membrane-water boundaries. (FIG. 6B) Cellulose synthase activity of the truncated BcsA-B complexes. IMVs containing wild-type BesA and the indicated BesB constructs were tested for cellulose synthase activity by quantifying the accumulation of radioactively labeled cellulose. IMVs were incubated with and without c-di-GMP for 60 min at 37° C. IMVs containing BcsA alone do not form cellulose. The purified BcsA-B-S684 complex retains activity after reconstitution into PLs (S684-r). (FIG. 6C) Western analysis of the analyzed IMVs and PLs. BcsA carries a C-terminal poly-histidine tag and all BcsB constructs were expressed with a C-terminal FLAG tag. The equivalent amounts of IMVs used for activity assays were used to quantify the BcsA and BcsB expression levels. Vesicles containing WT and the BcsA-B-S684-r complex were analyzed on separate gels. Red arrowheads highlight the positions of the BcsB-constructs.

FIG. 8A-8D (also referred to as Example 1, Supplementary FIG. 2): ELMS fragmentation spectra of the permethylated alditolacetates obtained from the product synthesized in vitro by the BcsA-B complex. The identity of the 1,5-di- O-acetyl, 2,3,4,6-tetra-O-methyl-D-glucitol and 1,4,5-tri-O-acetyl, 2,3,6-tri-O-methyl-D-glucitol corresponding to the t-Glc and 1,4-Glc residues, respectively, was verified after fragmentation by electron-impact mass spectrometry (EI-MS). EI-MS analysis performed on the other minor peaks visible on the chromatogram (e.g. before retention times of 13, 14, 17 and 19 min) (FIG. 2B) did not correspond to any sugar derivative. The fragmentation spectra obtained are characteristic of 1,4,5-tri-O-acetyl, 2,3,6-tri-O-methyl-D-glucitol (FIG. 8A) (GC retention time of 21.3 min; FIG. 2B) and 1,5-di-O-acetyl, 2,3,4,6-tetra-O-methyl-D-glucitol (FIG. 8B) (GC retention time of 10.8 min; FIG. 2B) and correspond to 1,4-Glc and t-Glc residues, respectively.

(FIG. 9A) Cellulose synthesis reactions were performed in the presence of 20 mM of the indicated cations or in the absence of any additional divalent cations with and without addition of 20 mM EDTA. The activities are shown relative to the activity in the presence of magnesium. (FIG. 9B) The BcsA-B complex exhibits a maximum catalytic activity at neutral pH. Activity assays were performed in phosphate buffer adjusted at the indicated pH, revealing a pH optimum at pH 7.5. All activity assays were performed for 45 min at 37° C. with 1 µM PLs-reconstituted. Rs BcsA-B and by quantifying the accumulation of $^3$H-labeled water insoluble cellulose as described.

Example 2

Figure 13A:
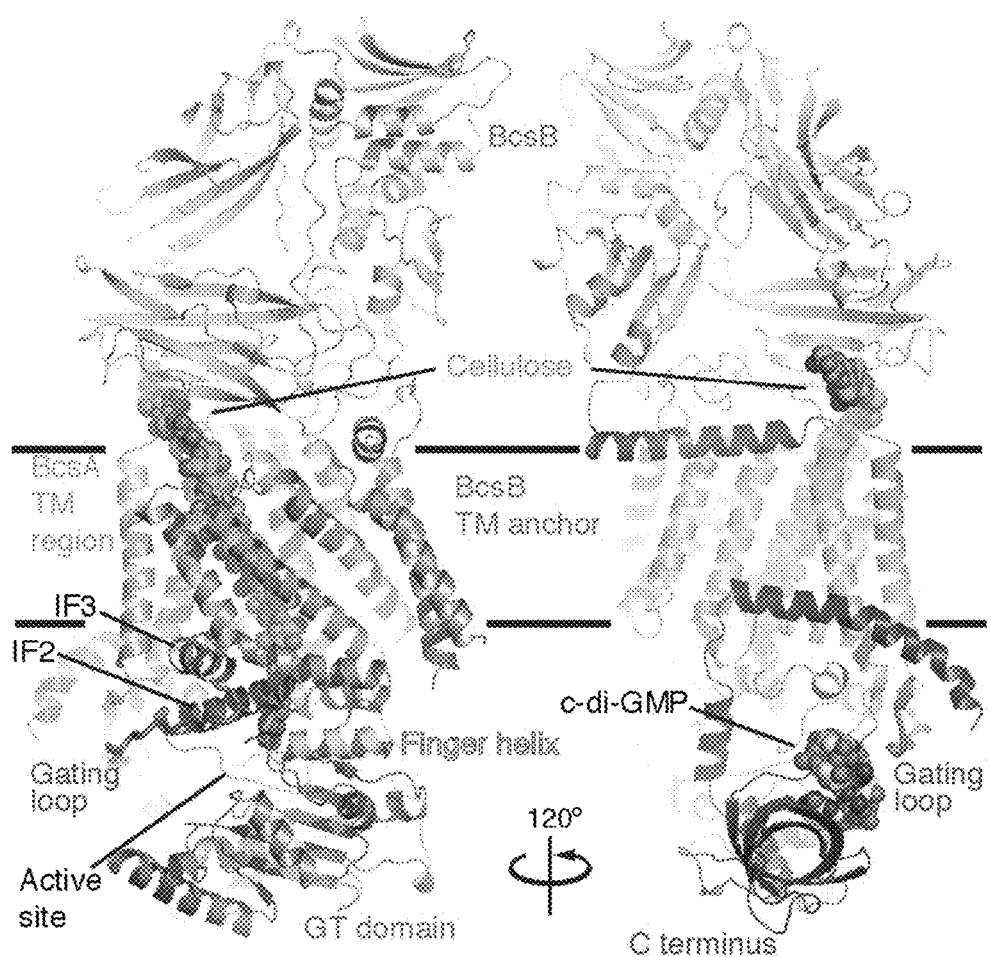
Figure 13B:
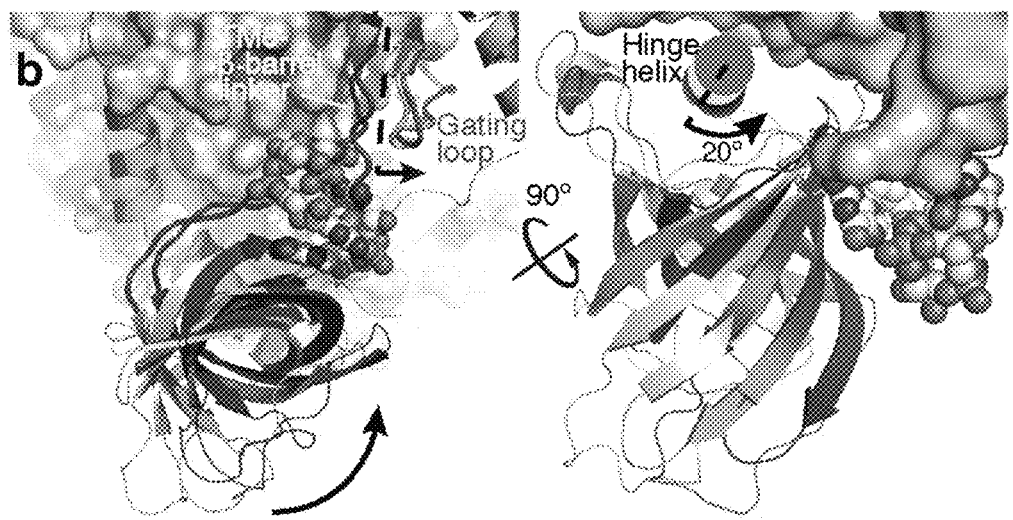
Figure 13C:
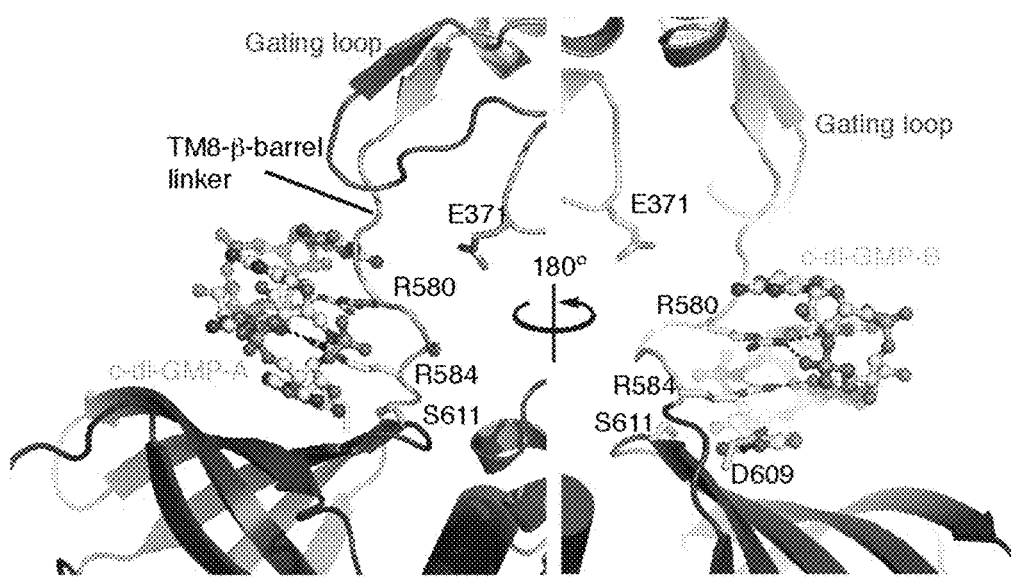

FIG. 13A-13C (also referred to as Example 2, FIG. 1): Structure of the c-di-GMP-activated BcsA-B complex. (FIG. 13A) Cartoon representation of the BcsA-B structure in the presence of a c-di-GMP homo-dimer. BcsA is colored brown, green, and red for its GT domain, TM region, and C terminus, respectively. The 6-stranded β-barrel within BcsA's C terminus forms a c-di-GMP binding PilZ domain. BcsB is shown in blue. The c-di-GMP dimer and translocating cellulose polymer are shown in spheres. BcsA's finger helix and gating loop are colored yellow and steel blue, respectively. IF: Amphipathic interface helices that surround the cytosolic entrance to BcsA's TM channel. Horizontal bars indicate the putative membrane boundaries. (FIG. 13B) Comparison of BcsA's PilZ positions in the presence and absence of c-di-GMP. BcsA is shown as a pale gray surface, and BcsA's C terminus is shown as a red cartoon. The position of the β-barrel in the c-di-GMP-free state (pdb 4HG6) is shown as a gray cartoon and c-di-GMP is shown as spheres. (FIG. 13C) Interactions of the "RxxxR" and "DxSxxG" motifs with the c-di-GMP dimer. Residues of each motif are shown as yellow sticks and c-di-GMP is shown in sticks and spheres.

Figure 14A:
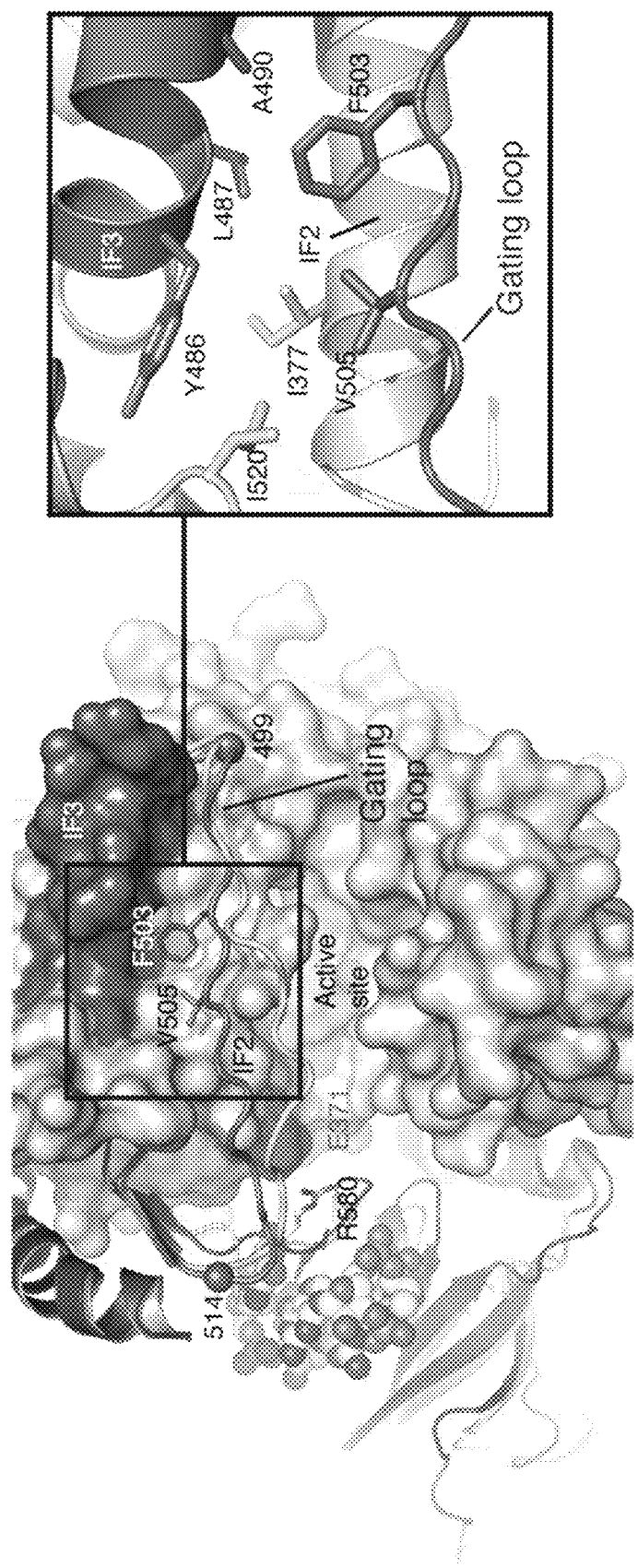
Figure 14B:
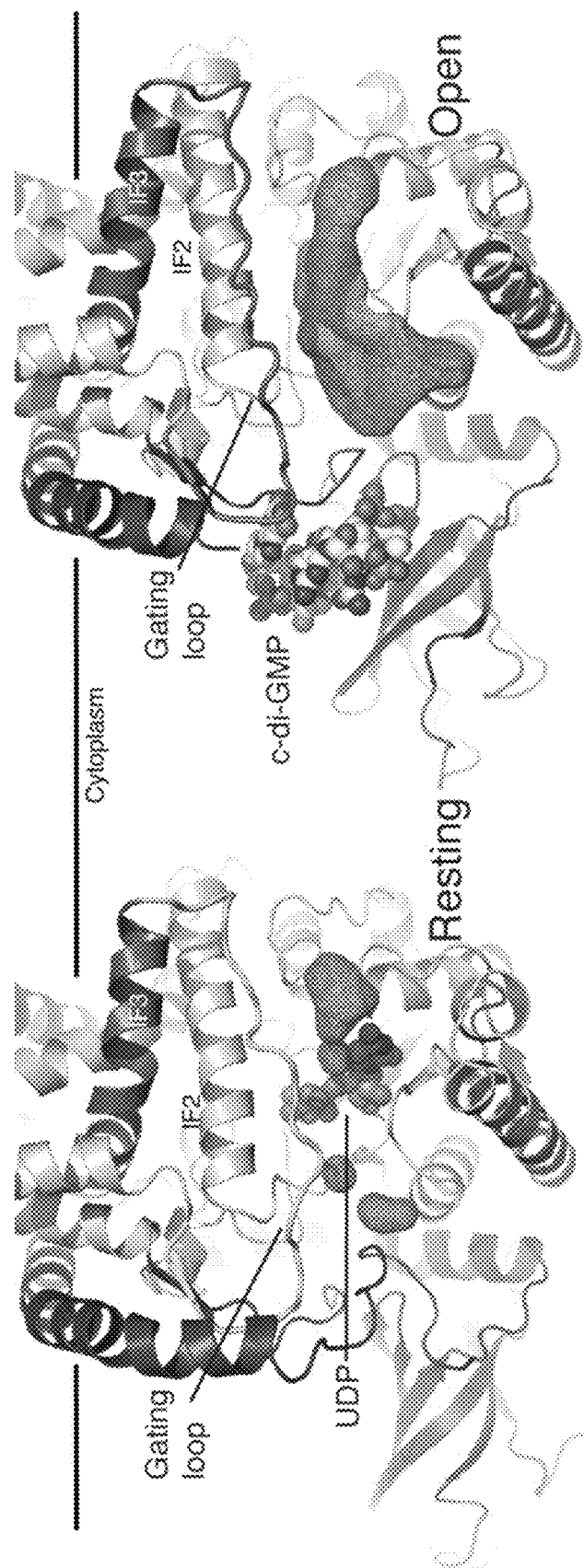

FIG. 14A-14B (also referred to as Example 2, FIG. 2): Conformational changes of BcsA's gating loop. (FIG. 14A) Gating loop positions in the absence and the presence of c-di-GMP (shown in cyan and steel blue, respectively). Phe503 and Val505 of the "FxVTxK" motif are shown as sticks and the gating loop's pivots, Arg499 and Glu514, are shown as spheres. The C terminus is colored as in FIG. 1. Inset: residues involved in stabilizing the gating loop in the "open" position are shown as sticks. (FIG. 14B) Accessible volume at the active site entrance (dark blue mesh) in the absence (left) and the presence (right) of c-di-GMP, calculated with a 3.5 Å probe sphere. UDP in the resting (pdb 4HG6) and c-di-GMP in the open BcsA-B structure are shown as spheres.

Figure 15:
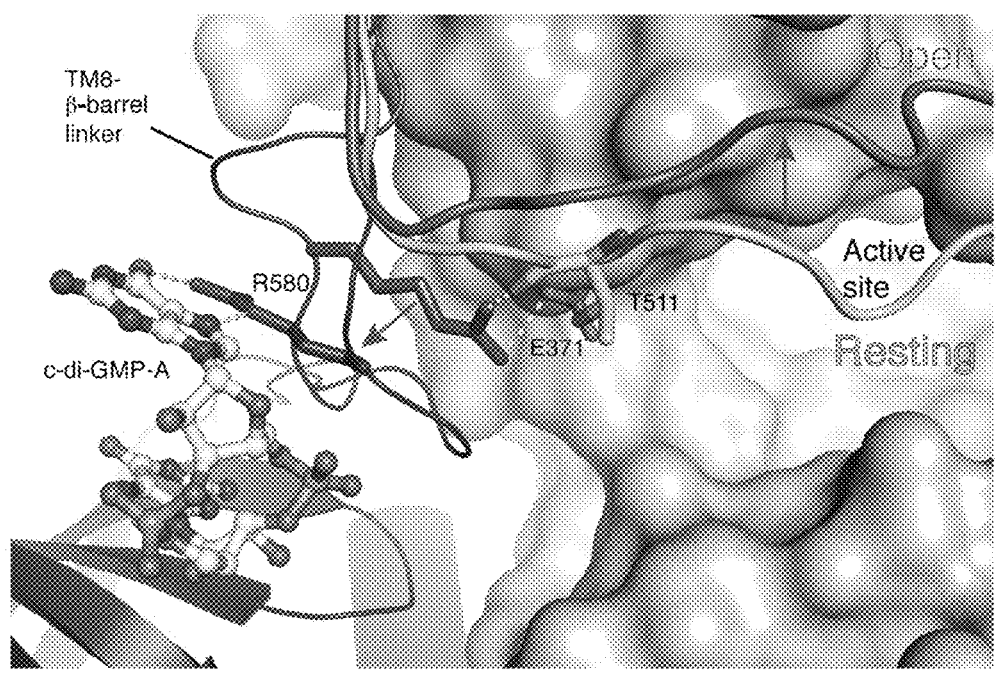

FIG. 15 (also referred to as Example 2, FIG. 3): Stabilization of the gating loop by Arg580. A comparison of the Arg580 position in the absence and presence of c-di-GMP. Arg580 is shown as dark gray and red in the absence and presence of c-di-GMP, respectively. The gating loop is shown in cyan and steel blue representing the "resting" and "open" states, respectively. Glu371 is shown in sticks, and putative interactions are indicated. BcsA's PilZ domain is colored red and the TM8-β-barrel linker in the resting state is shown as a dark gray cartoon.

Figure 4A:
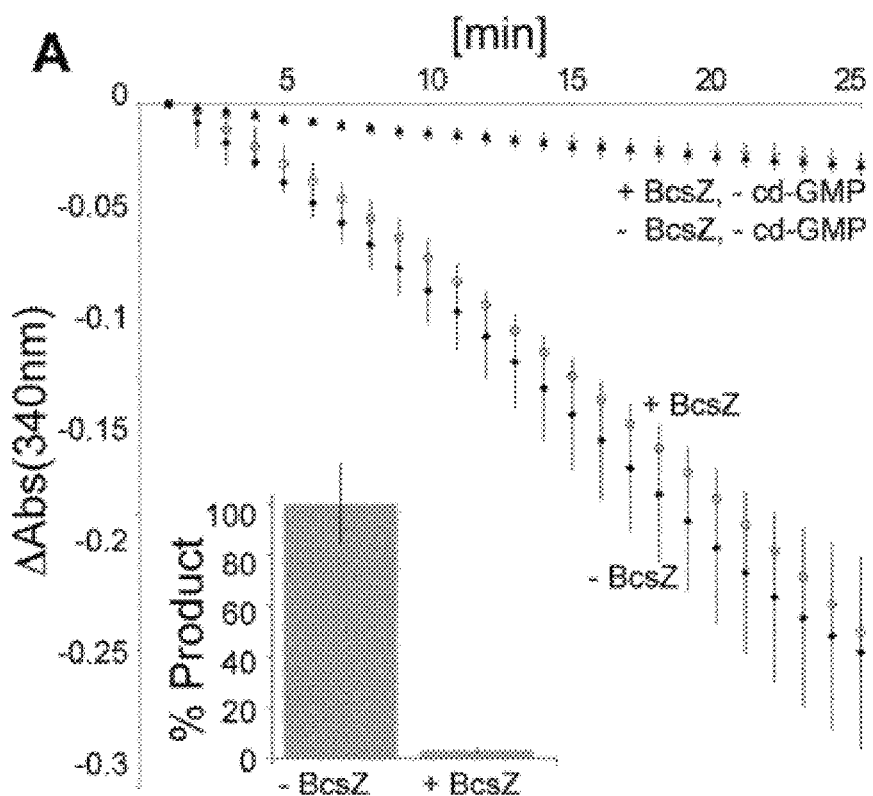
FIG. 4A-4C (also referred to as Example 1, FIG. 4): Product inhibition of cellulose synthase.
Figure 16A:
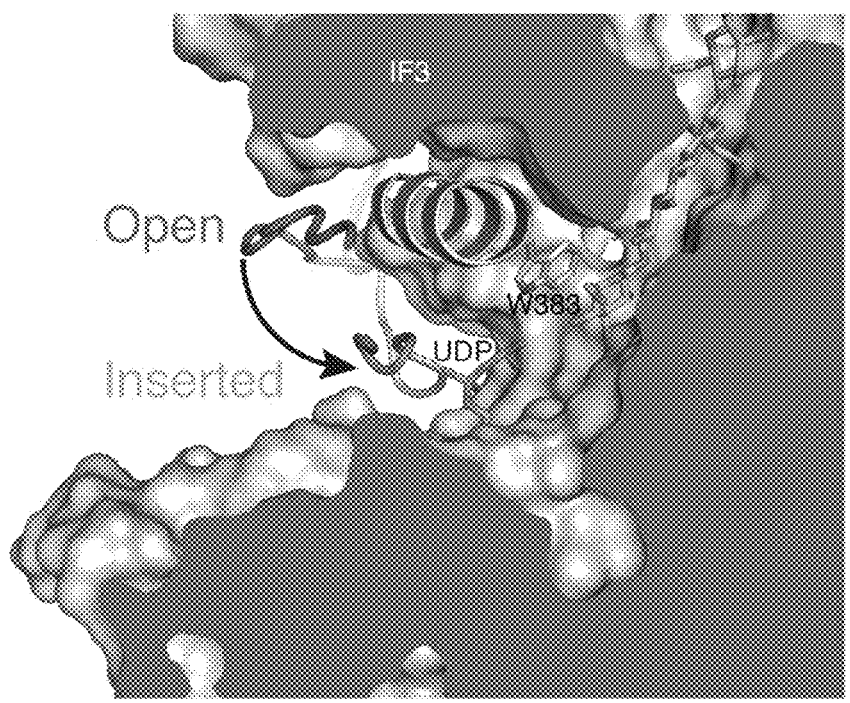
Figure 16B:
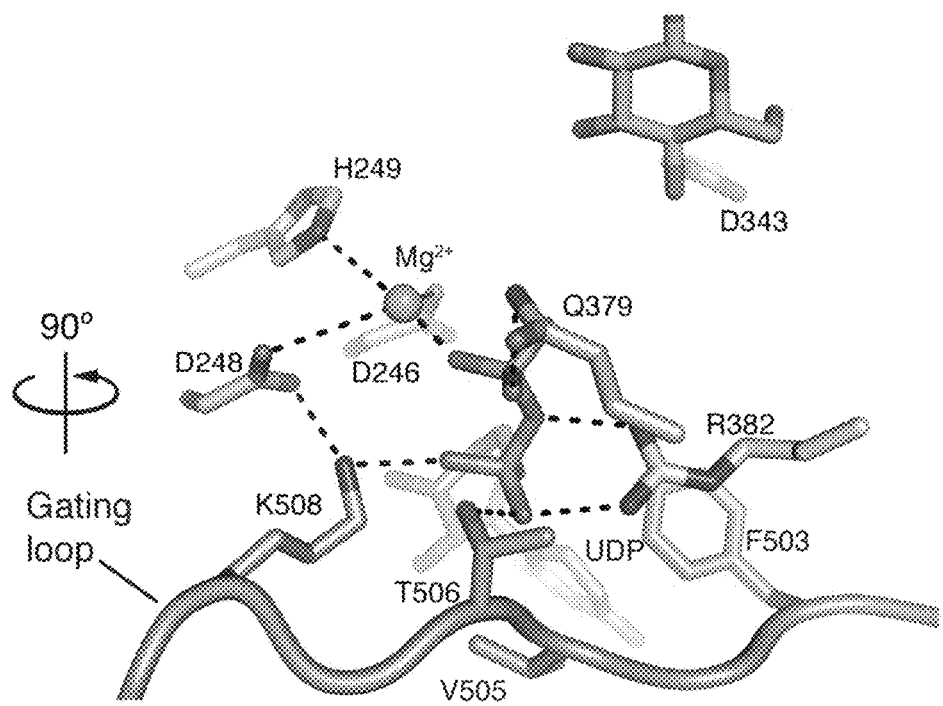

FIG. 16A-16B (also referred to as Example 2, FIG. 4): Insertion of the gating loop into the catalytic pocket. (FIG. 16A) A comparison of the gating loop positions of c-di-GMP-bound BcsA-B in the absence and presence of UDP (shown in steel blue and green, respectively). The inserted gating loop is colored green, IF2 is shown as a gray cartoon helix, and UDP as well as the translocating cellulose polymer are shown as sticks. Trp383 of the "QxxRW" motif at the entrance to the TM channel is shown as gray sticks. (FIG. 16B) Coordination of UDP at the active site by the gating loop's "FxVTxK" motif. The gating loop is colored green, representing the "inserted" state. UDP, the conserved residues of the gating loop as well as Gln379 and Arg382 of the "QxxRW" motif are shown as sticks. The terminal glucose of the cellulose polymer and the putative catalytic base (Asp343) are shown as cyan and gray sticks, respectively.

Figure 17A:
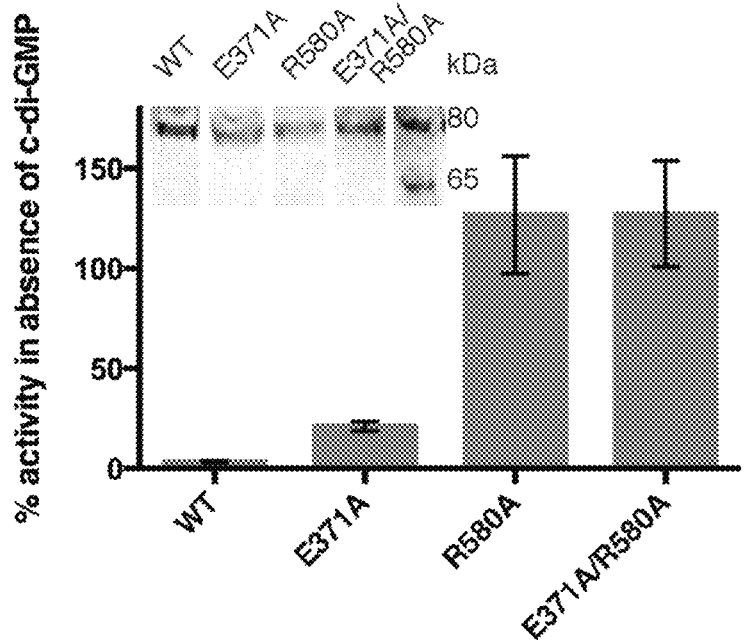
Figure 17B:
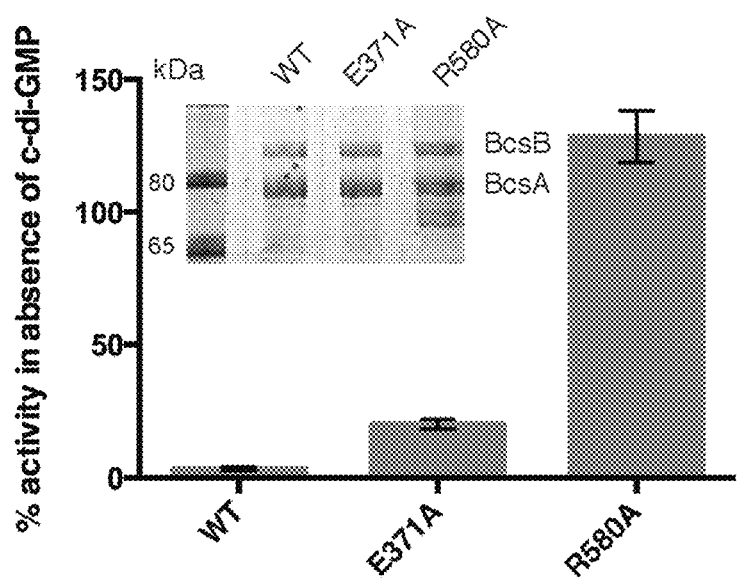
Figure 17C:
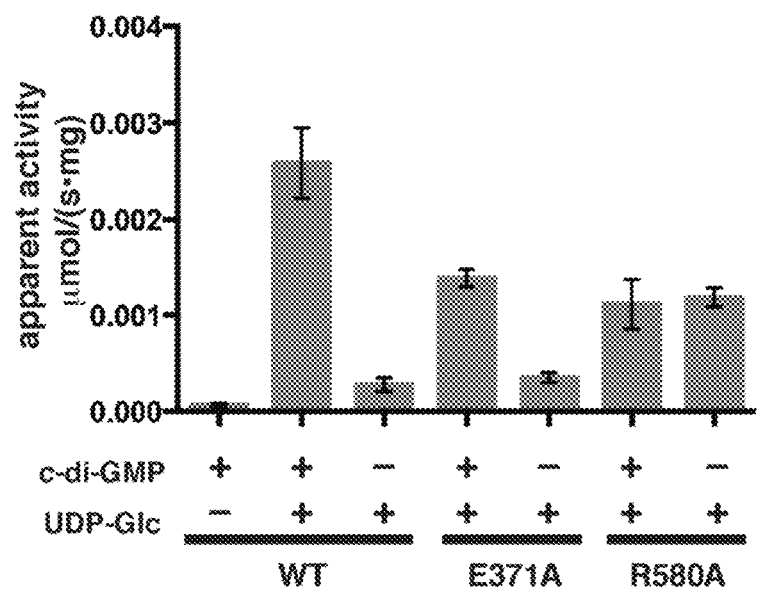
Figure 17D:
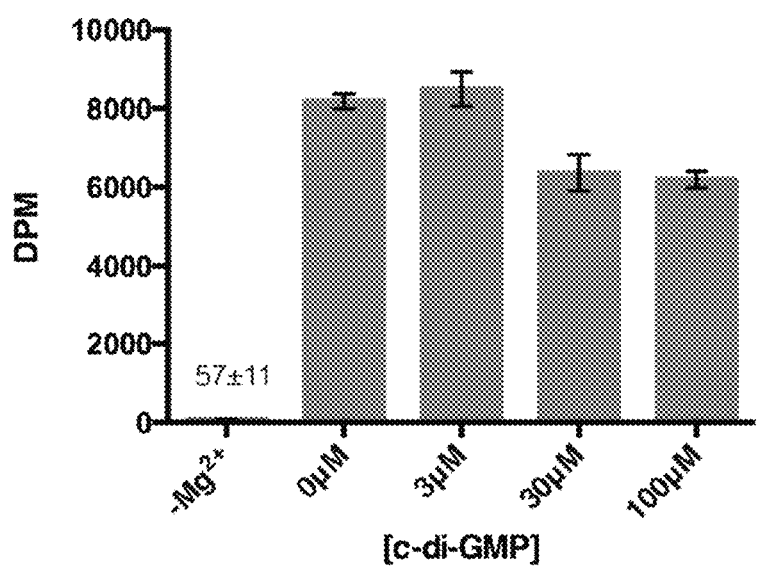
Figure 18C:
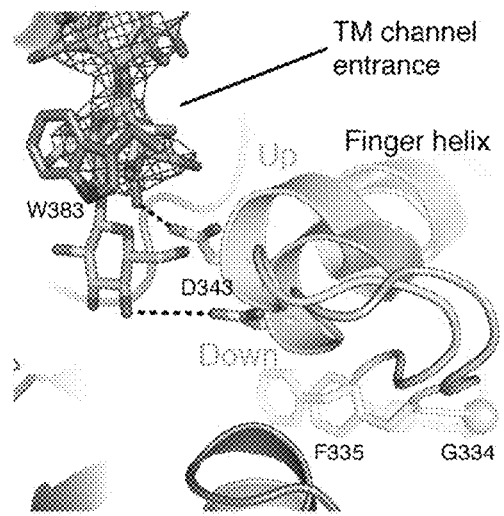
Figure 18C:
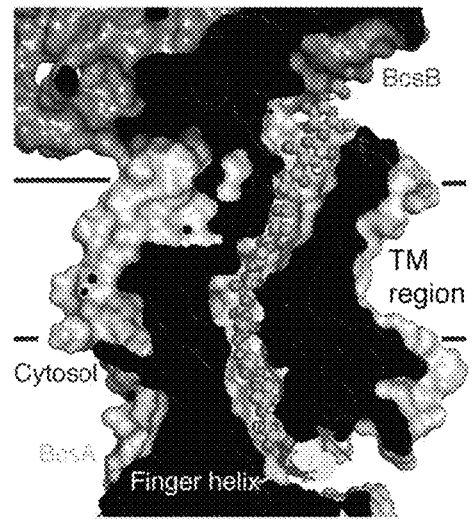
Figure 18C:
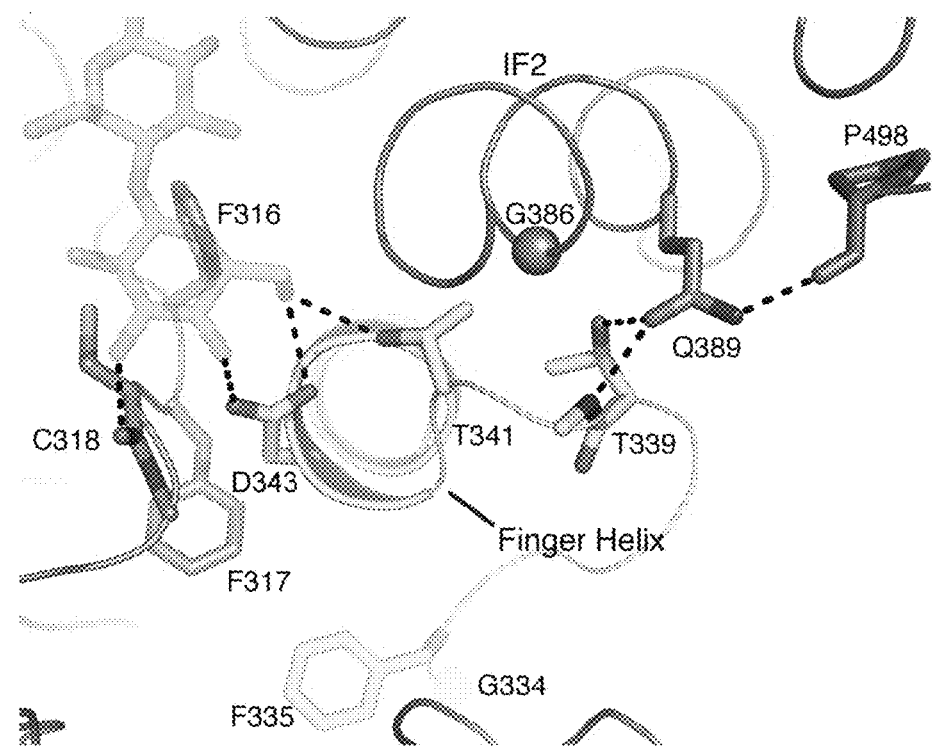
Figure 18D:
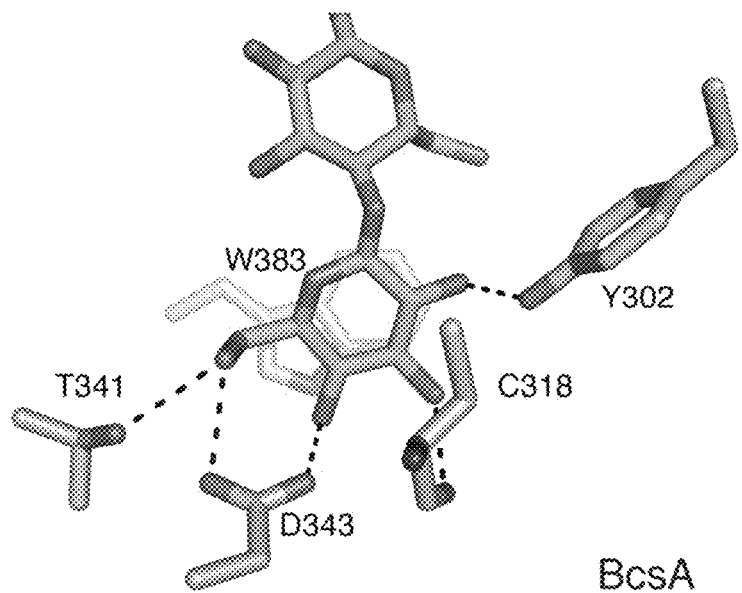
Figure 18E:
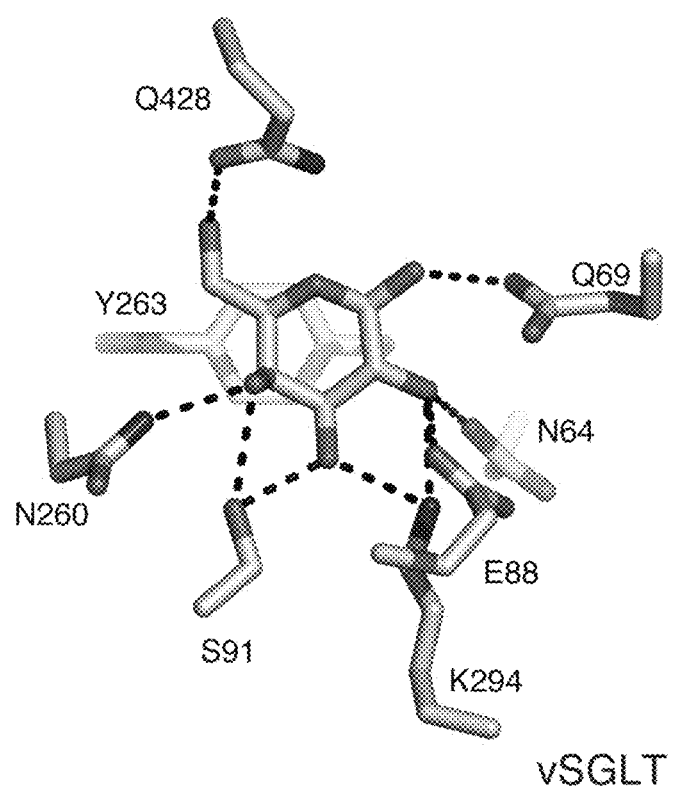

FIG. 17A-17D (also referred to as Example 2, FIG. 5): Comparison of BcsA-catalyzed in vitro cellulose synthesis in the absence and the presence of c-di-GMP. (FIG. 17A and FIG. 17B) Inverted membrane vesicles and proteoliposomes (PL), respectively, containing BcsA-B with the indicated mutations in BcsA were used for cellulose synthesis assays. (WT: wild type). The activity in the absence of c-di-GMP is quantified relative to the activity in the presence of 30 μM c-di-GMP. Insets: Western analysis of IMVs against the C-terminal poly-histidine tag on BcsA (FIG. 17A) and Coomassie-stained SDS-PAGE of the purified BcsA-B complexes (FIG. 17B). (FIG. 17C) Catalytic rates of the indicated PL-reconstituted BcsA-B mutants in the presence and absence of 30 μM c-di-GMP as measured by quantifying the formation of UDP. (FIG. 17D) Activity of the PL-reconstituted BcsA R580A mutant at increasing c-di-GMP concentrations. No activity is observed in the presence of 30 μM c-di-GMP when magnesium is depleted with 25 mM EDTA (—$Mg^{2+}$). DPM: Disintegrations per minute. (All data represent the means±SD for 3 technical replicates).

FIG. 18A-18E (also referred to as Example 2, FIG. 6): Movement of the finger helix, cellulose translocation, and the acceptor position. (FIG. 18A) Comparison of the positions of BcsA's finger helix and translocating glucan in the resting (colored gray, pdb 4HG6) and c-di-GMP-bound states. An unbiased SigmaA-weighted mFo-DFc difference electron density of the translocating cellulose polymer in the UDP-free, c-di-GMP-bound state is contoured at 3.5σ and shown as a magenta mesh. The positions of the glucan as observed in the resting state and the c-di-GMP-bound structure are shown as gray and cyan sticks, respectively. BcsA's finger helix and the preceding small loop are colored yellow. (FIG. 18B) Cut-away view of BcsA's TM channel with the position of the finger helix in the c-di-GMP-bound and resting states shown as yellow and gray solid cylinders, respectively. The translocating glucan is shown as cyan and red spheres and Asp343 is shown as sticks. Membrane boundaries are indicated by horizontal black lines. (FIG. 18C) Conserved residues involved in stabilizing the finger helix in the "up" position are shown as sticks. (FIG. 18D) Residues coordinating the polymer's terminal glucose are shown as sticks. (FIG. 18E) Stabilization of a single galactose molecule by the sodium-dependent sugar transporter vSGLT. Residues coordinating galactose are shown as sticks (pdb 3DH4).

Figure 19:
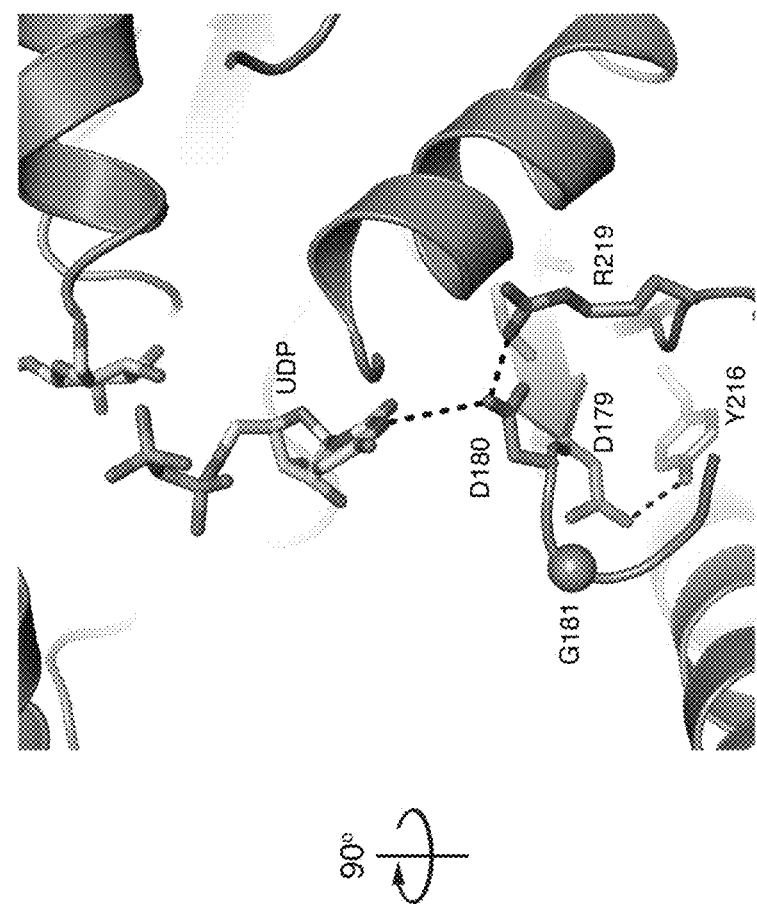
Figure 19:
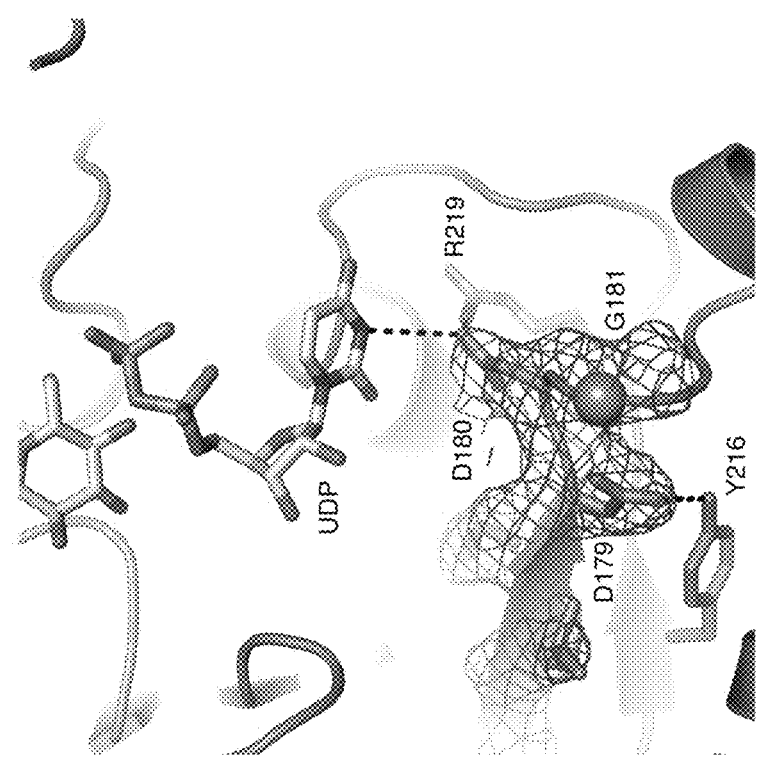

FIG. 19 (also referred to as Example 2, Supplementary FIG. 1): Correction of a register shift in BcsA. A register shift in BcsA (residues 171 to 190) has been corrected in the new structure. The new 2.65 Å electron density map allows the unambiguous assignment of the register in this β-strand. The corrected register positions Asp179 of the conserved "DDG" motif in hydrogen bonding distance to the conserved Tyr216 and Asp180 in hydrogen bonding distance to the UDP uracil moiety and the conserved Arg219. A SigmaA-weighted 2mFo-DFc electron density contoured at 1σ is shown as a blue mesh. UDP and the translocating glucan as observed in pdb 4HG6 are shown as gray sticks.

Figure 20A:
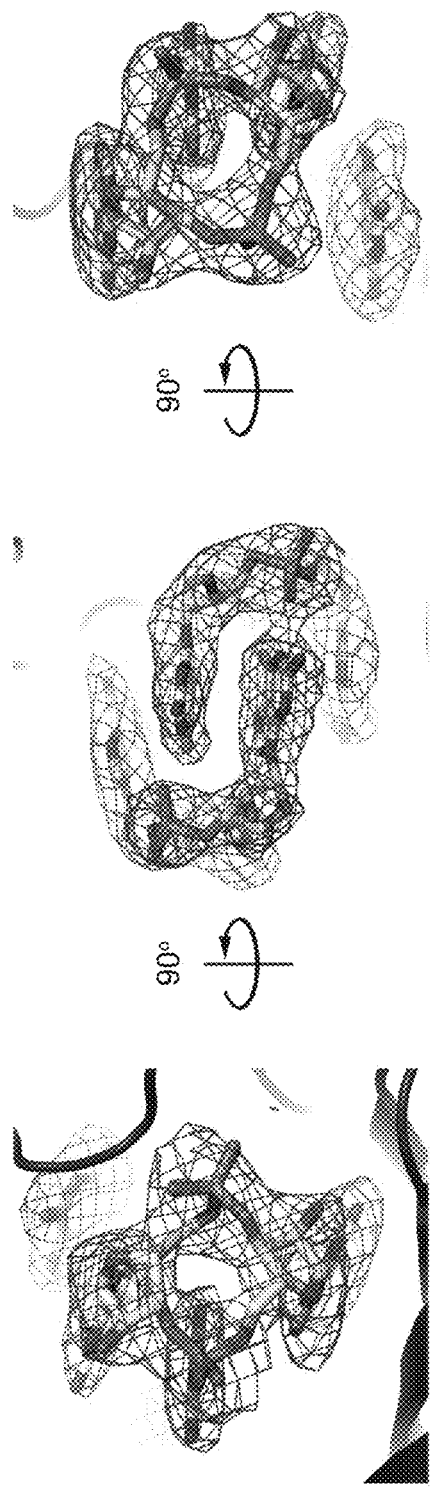
Figure 20B:
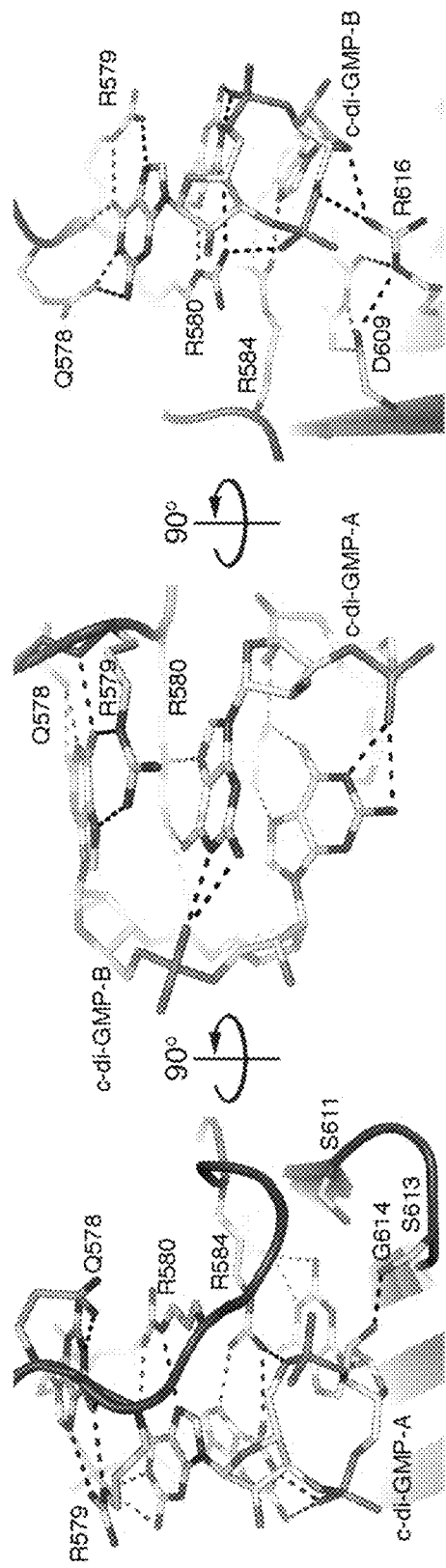
Figure 21C:
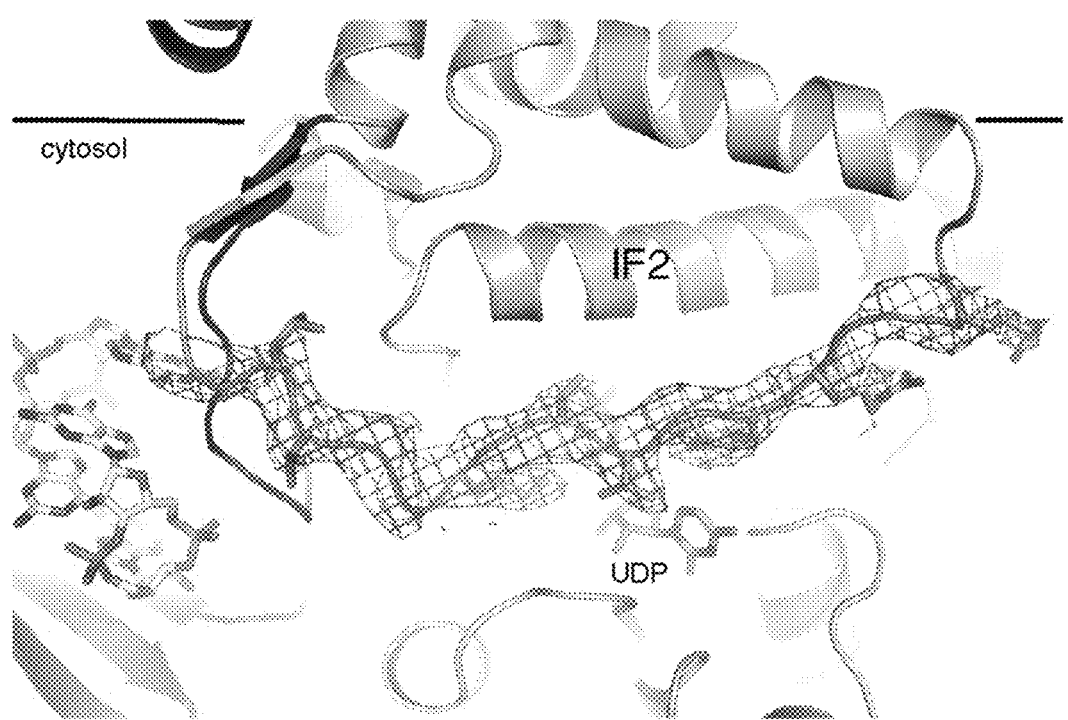
Figure 21D:
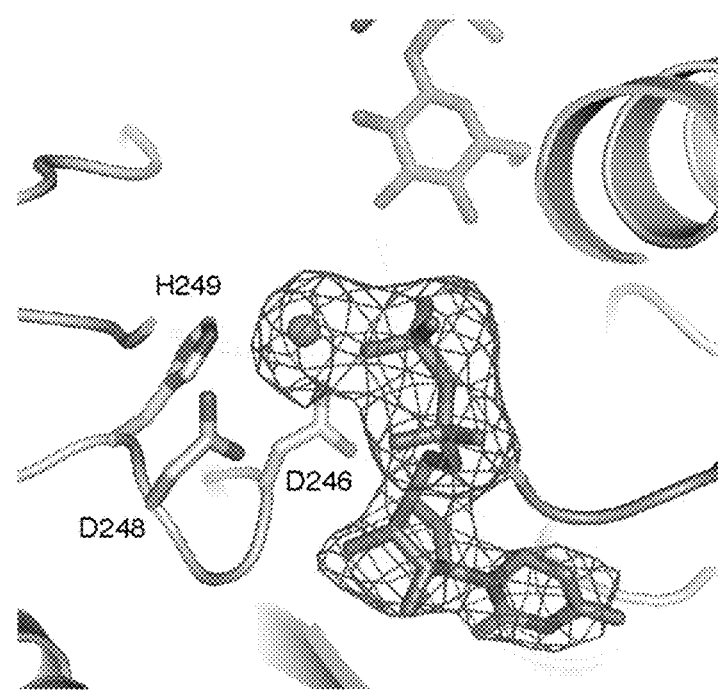
Figure 21E:
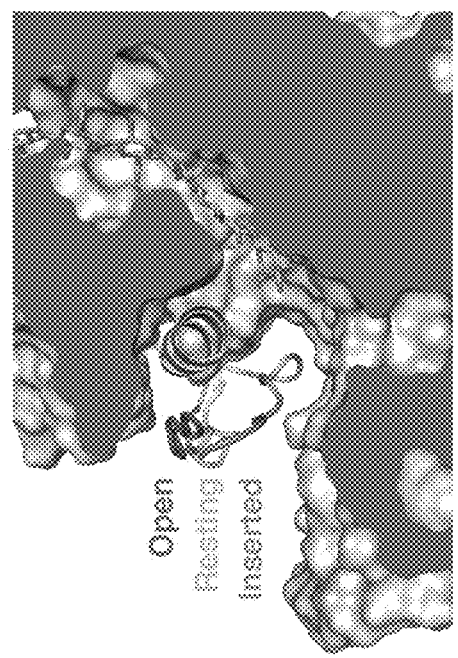
Figure 21E:
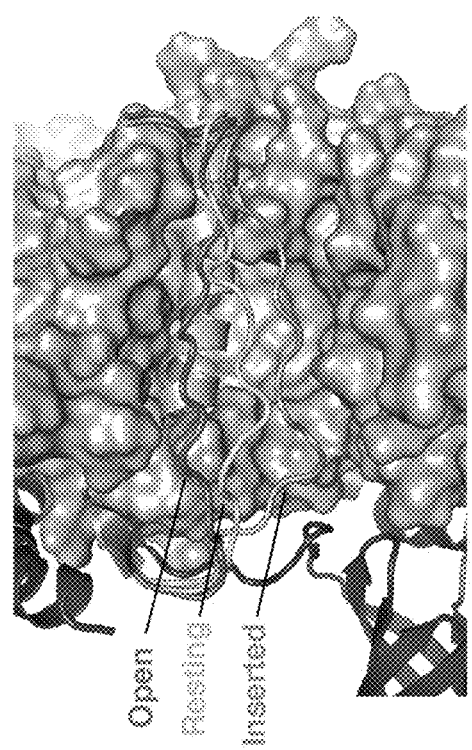

FIG. 20A-20B (also referred to as Example 2, Supplementary FIG. 2): Cyclic-di-GMP binding to BcsA. (FIG. 20A) An intercalated homodimer of c-di-GMP binds to BcsA's PilZ domain. An unbiased SigmaA-weighted mFo-DFc difference electron density for c-di-GMP contoured at 4σ is shown as a magenta mesh. The density was calculated after refining the protein structure and before placing any ligands. The c-di-GMP dimer is shown in sticks colored light blue or pale brown for the carbon atoms, respectively. (FIG. 20B) BcsA's PilZ domain tightly coordinates a c-di-GMP dimer, c-di-GMP-A and -B. One guanylate group of c-di-GMP-A (GA1) packs its guanine group into a pocket on the β-barrel surface formed by the conserved Gly614 and Gly670 where it is further stabilized by side chain interactions with Asp609 of the "DxSxxG" motif as well as Ser613 and Arg616. The guanine interacts with Asp609 via its cyclic N1 atom and exocyclic amine group and its carbonyl oxygen contacts the guanidinium group of Arg616. Ser611 of the "DxSxxG" motif does not directly contact GA1, however, it is likely that its interaction is mediated by an unresolved water molecule. The 2' hydroxyl of the GA1 ribose interacts with the hydroxyl group of Ser613. Arg584 of the TM8-β-barrel linker stacks on top of the GA1 guanine and forms a salt bridge with the phosphate group belonging to the second guanylate of c-di-GMP-A (GA2). The side chain of the invariant Arg580 of the TM8-β-barrel linker is co-planar with the guanine of GA2 and forms hydrogen bonds via its guanidinium group with the GA2's guanine N7 and carbonyl oxygen. Similar to the stacking interactions observed for GA1, the preceding Arg579 stacks on top of the GA2 guanine group. The ring N1 and exocyclic amine group of GA2 interact with the phosphate moiety of the second c-di-GMP molecule (c-di-GMP-B). C-di-GMP-B makes fewer interactions with BcsA and is primarily stabilized by c-di-GMP-A and residues belonging to the TM8-β-barrel linker. Its first guanylate closest to the β-barrel surface (GB1) forms π-π stacking interactions with the guanine of GA2 and hydrogen bonds via its ring N7 and carbonyl oxygen with Arg584, the same residue that stacks on top of the GA1 guanine. As observed for the guanine group of GA2, its ring N1 and exocyclic amine contact the phosphate group of the other c-di-GMP molecule, thereby stabilizing the intercalated c-di-GMP dimer. The second guanylate of c-di-GMP-B (GB2) interacts via its ring carbonyl oxygen with the backbone nitrogen as well as the Nε of the co-planar Arg579 and via the guanine's N1 and exocyclic amine with the invariant Gln578 of the TM8-β-barrel linker. In addition, its phosphate group forms a salt bridge with Arg580 that is co-planar with the guanine of GA2.

FIG. 21A-21E (also referred to as Example 2, Supplementary FIG. 3): Conformational changes of BcsA's gating loop. (FIG. 21A) Sequence conservation of the gating loop. The "FxVTxK" motif is conserved in pro- and eukaryotic cellulose synthases. (FIG. 21B) Unbiased SigmaA-weighted 2mFo-DFc electron density for the gating loop in the "up" position shown as a magenta mesh and contoured at 1σ. The density was calculated before modeling the gating loop. The position of the loop's backbone is well resolved (colored cyan). The side chains of Phe503 and Val505 pack into a hydrophobic pocket on IF2 and are well resolved in the original density map. (FIG. 21C and FIG. 21D) Unbiased SigmaA-weighted mFo-DFc difference electron density for the gating loop in the "down" position and UDP, shown as a magenta mesh. The density was calculated before modeling the gating loop and placing UDP/Mg and is contoured at 2.5σ and 3σ for the gating loop and UDP, respectively. The position of the entire gating loop backbone is well resolved and so are the side chains of the conserved Phe503, Val505, Thr506 and Lys508. Additional electron density between the UDP β-phosphate and BcsA's "DxD'" motif is consistent with a bound magnesium ion (shown as a green sphere). UDP is shown in sticks colored violet for the carbon atoms and the gating loop is colored green. (FIG. 21E) Front and side view comparing the three gating loop positions observed in the resting and c-di-GMP bound states. BcsA is shown as a gray surface with the PilZ domain shown as a red cartoon. The three gating loop positions are shown as cartoons and indicated with their respective colors.

Figure 22A:
Figure 22B:
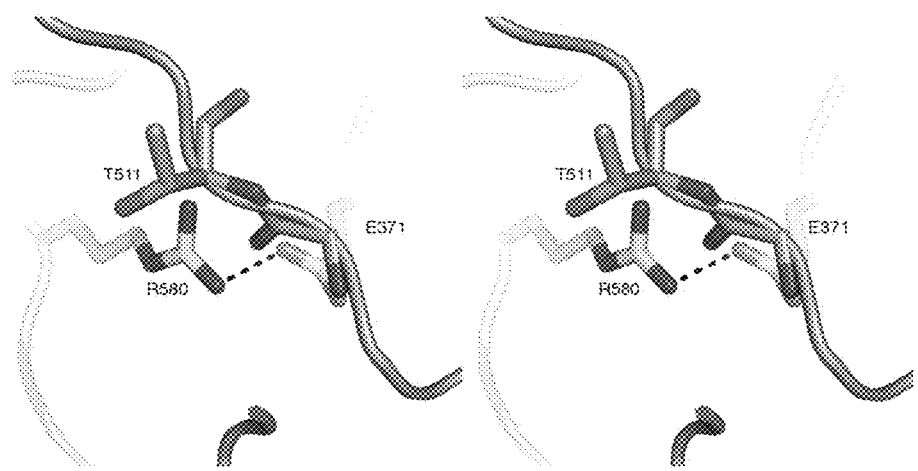

FIG. 22A-22B (also referred to as Example 2, Supplementary FIG. 4): A conserved salt bridge stabilizes the resting position of BcsA's gating loop. (FIG. 22A) Sequence alignment of pro- and eukaryotic cellulose synthases. In the absence of c-di-GMP, the N-terminal Arg of the PilZ domain's "RxxxR" motif forms a salt bridge with a conserved Glu within the GT domain (framed red). Some outliers, such as BcsA from *R. leguminosarum*, contain an Ala at this position, expected to decrease the dependence on c-di-GMP for cellulose biosynthesis. The *C. difficile* sequence might be shifted in this region and the Asp residue next to the aligned Thr might confer a similar functionality. For eukaryotic cellulose synthases, Ile is the most prevalent residue at the corresponding position. The secondary structure of the aligned sequences is shown as a cartoon based on the *R. sphaeroides* BcsA structure. Pro- and eukaryotic sequences are separated by a dashed line. (FIG. 22B) The Glu371-Arg580 salt bridge blocks gating loop insertion in the absence of c-di-GMP. Stereoview of a superposition of pdb 4HG6 and the c-di-GMP/UDP bound structure. Arg580 and Glu371 from 4HG6 are shown as yellow sticks. The inserted state of the gating loop from the c-di-GMP/UDP bound structure is shown in green. A clash between Glu371-Arg580 and the C-terminal end of the gating loop would prevent loop insertion in the absence of c-di-GMP.

Figure 23A:
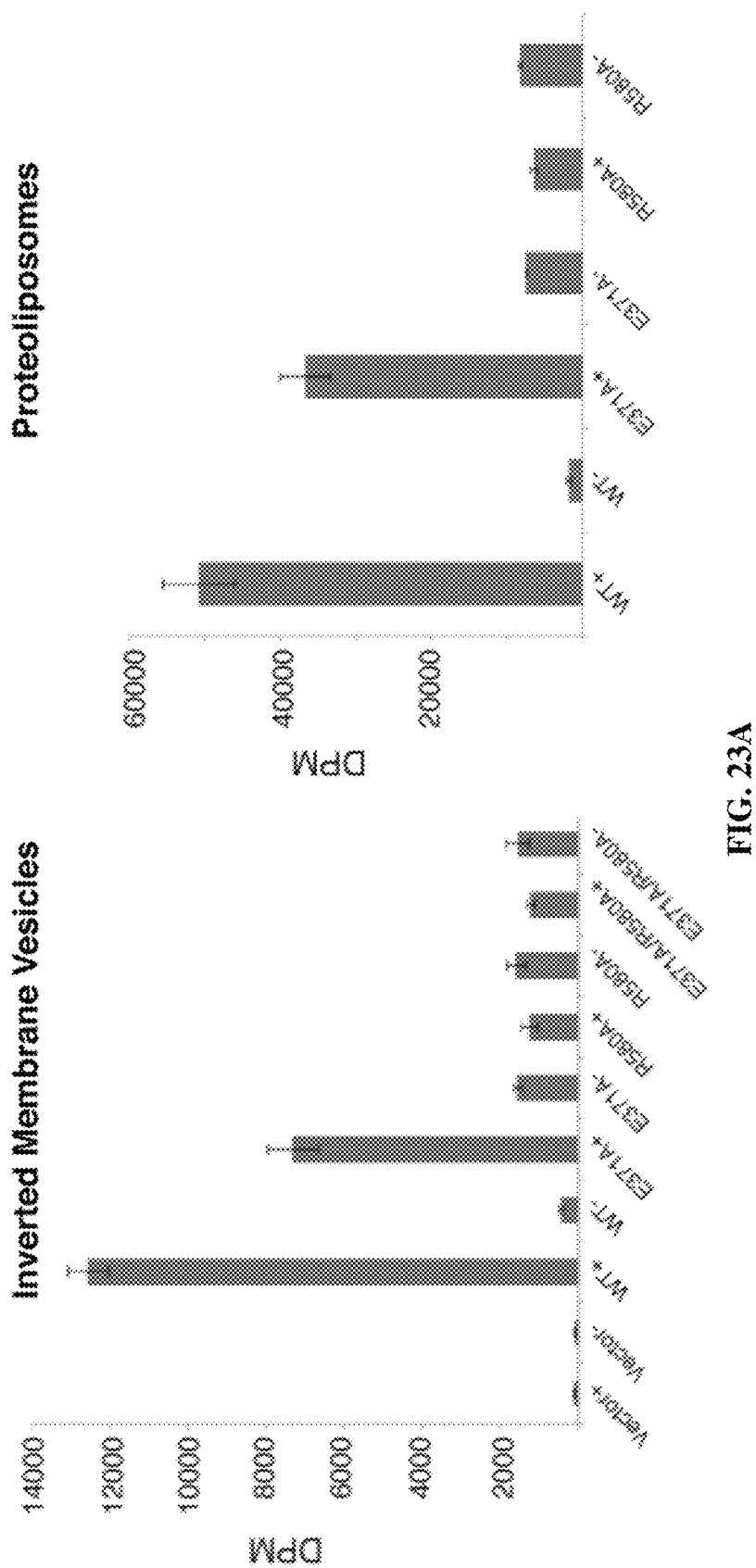
Figure 23B:
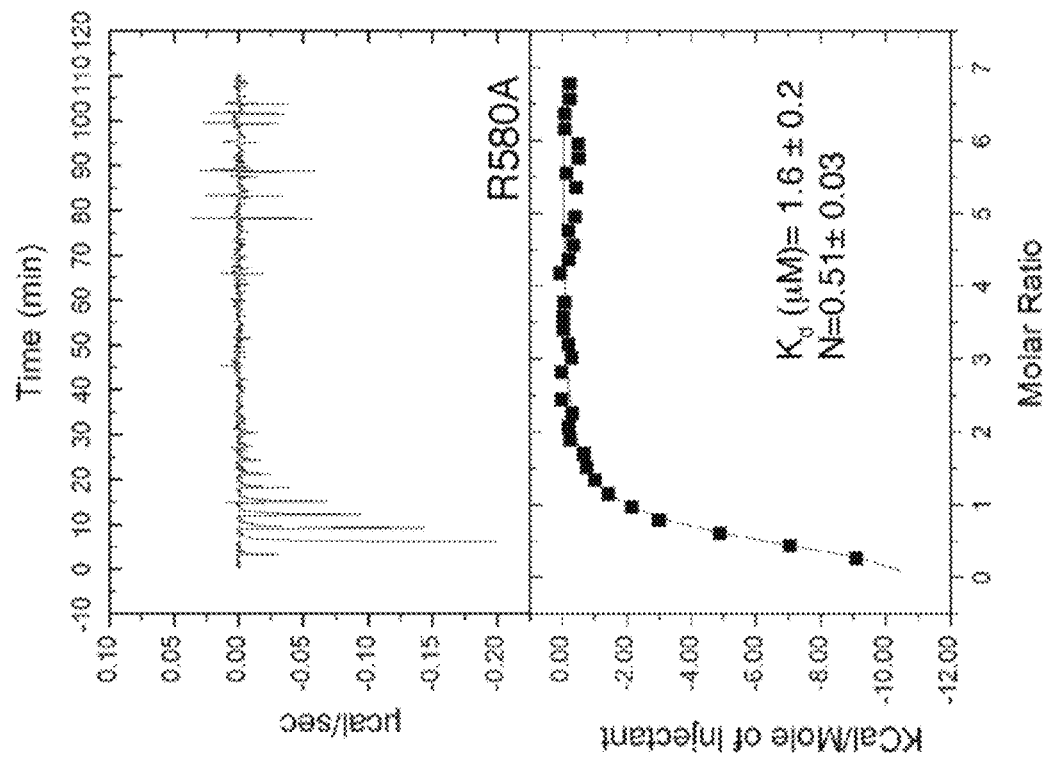
Figure 23B:
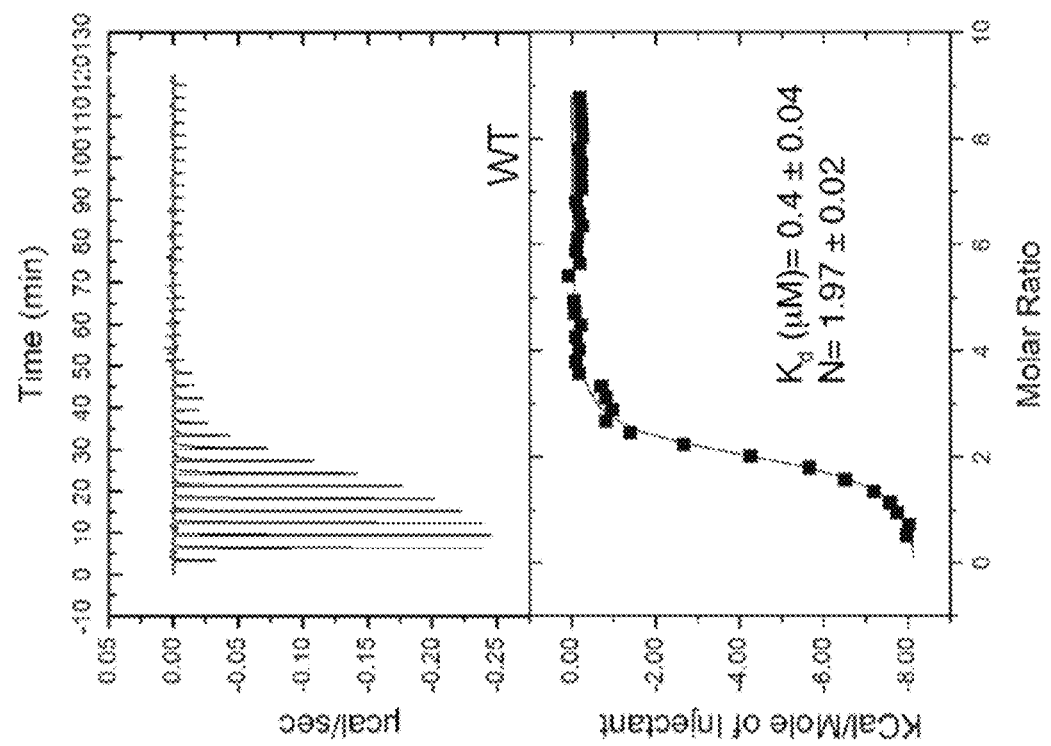

FIG. 23A-23B (also referred to as Example 2, Supplementary FIG. 5): Cellulose synthesis activity of BcsA mutants and c-di-GMP binding. (FIG. 23A) Cellulose synthesis assays were performed in inverted membrane vesicles and proteoliposomes as described in the Experimental Procedures. The amount of $^3$H-glucose-labeled cellulose produced by each mutant is quantified and graphed. 1 µl of IMV's were used for each mutant. For PL assays, the protein concentrations were matched based on UV absorbance and SDS-PAGE followed by Coomassie staining. The apparent lower activity of the R580A mutant may be due to differences in the relative orientation of the enzyme in the PLs or its overall stability. +/−: Experiments performed in the presence and absence of 30 µM c-di-GMP. All data represent the means±SD for 3 technical replicates. (FIG. 23B) Binding of c-di-GMP to the BcsA-R580A mutant. The ability of the R580A mutant to bind c-di-GMP was assessed using ITC. Left panel, titrating c-di-GMP into wild type (WT) BcsA-B in 1 mM LFCE14 results in an exothermic curve with a $K_d$ of 0.4 µM and a c-di-GMP to BcsA-B stoichiometry of ~2:1 as expected based on the crystal structure. Right panel, BcsA-R580A under the same conditions exhibits a $K_d$ of 1.6 µM and a stoichiometry of ~0.5. The observation that only ½-¼ of the BcsA-R580A population (depending on whether the mutant binds a c-di-GMP monomer or dimer) interacts with c-di-GMP suggests that a fraction of it is structurally compromised, consistent with the results obtained from functional assays (FIG. 23A).

Figure 24C:
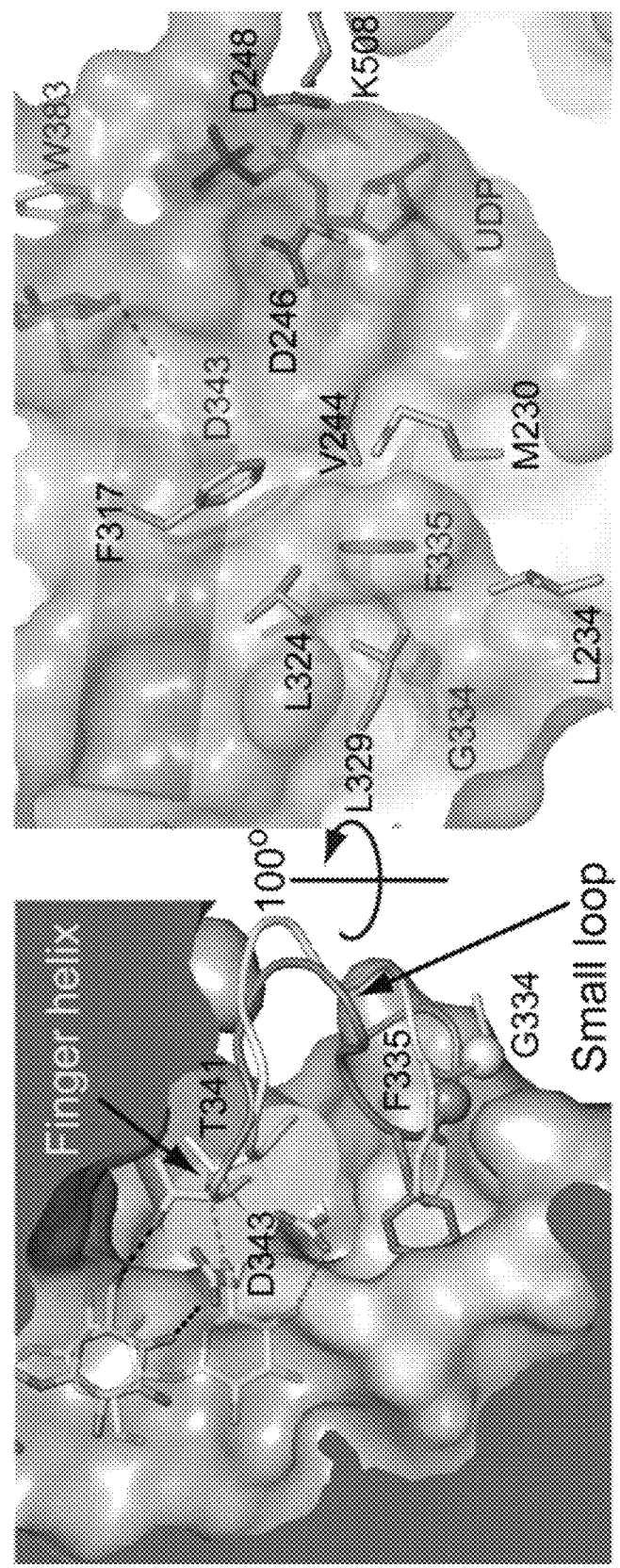

FIG. 24A-24C (also referred to as Example 2, Supplementary FIG. 6): The movement of BcsA's finger helix is supported by a small loop. (FIG. 24A) Sequence alignment of pro- and eukaryotic cellulose synthases. The small loop contains a conserved Gly residue that is followed by a hydrophobic residue, usually Phe or Trp (framed red). The finger helix carries the invariant "TED" motif at its N terminus and contains a conserved His residue (framed red) followed by a Gly-Trp/Tyr motif that stabilizes the helix at its C terminus. (FIG. 24B) The C terminus of BcsA's finger helix (shown as a yellow cartoon) is stabilized by His351, which interacts with the invariant Ser357 and Tyr410. Leu348 packs against Met390 of IF2 and Tyr410 of IF3. Arg353 and Trp355 cap the helix at its C-terminal end. (FIG. 24C) Comparison of BcsA's finger helix and small loop in the presence and absence of c-di-GMP. The translocating glucan is shown before and after finger helix movement as gray and cyan sticks, respectively. In the presence of c-di-GMP, Phe335 of the small loop packs into a hydrophobic pocket (shown as a pale orange surface) underneath the finger helix. The preceding conserved Gly334 is shown as a sphere. The position of the finger helix and small loop in the resting state (pdb 4HG6) is shown as a gray cartoon. The right panel shows the same surface boundary as on the left but viewed from the opposite side.

Figure 7:
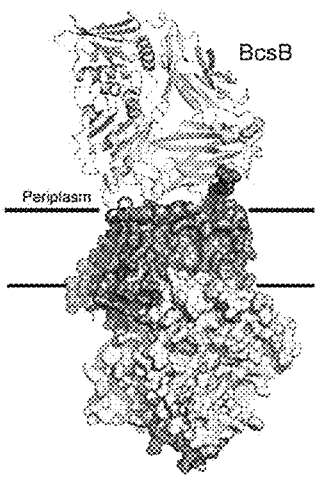
FIG. 7 (also referred to as Example 1, Supplementary FIG. 1): Sequence alignment of BcsB. BcsB sequences from *Salmonella typhimurium* (St), *Escherichia coli* (Ec), *Pseudomonas putida* (Pp), *Gluconacetobacter xylinus* (Ax), *Klebsiella pneumoniae* (Kp) and *Rhodobacter sphaeroides* (Rs) are compared. The alignment is colored according to the individual BcsB domains: CBD-1: blue, FD-1: orange, CBD-2: cyan, FD-2: sand, TM-anchor and preceding interface helix: dark blue. Conserved cysteines forming a disulfide bridge are framed black and are shown as yellow spheres in the right panel. Right panel: Structure of the Rs BcsA-B complex. BcsA is shown as a surface in shades of gray; BcsB is shown as cartoon colored according to the sequence alignment (left panel).
Figure 8A:
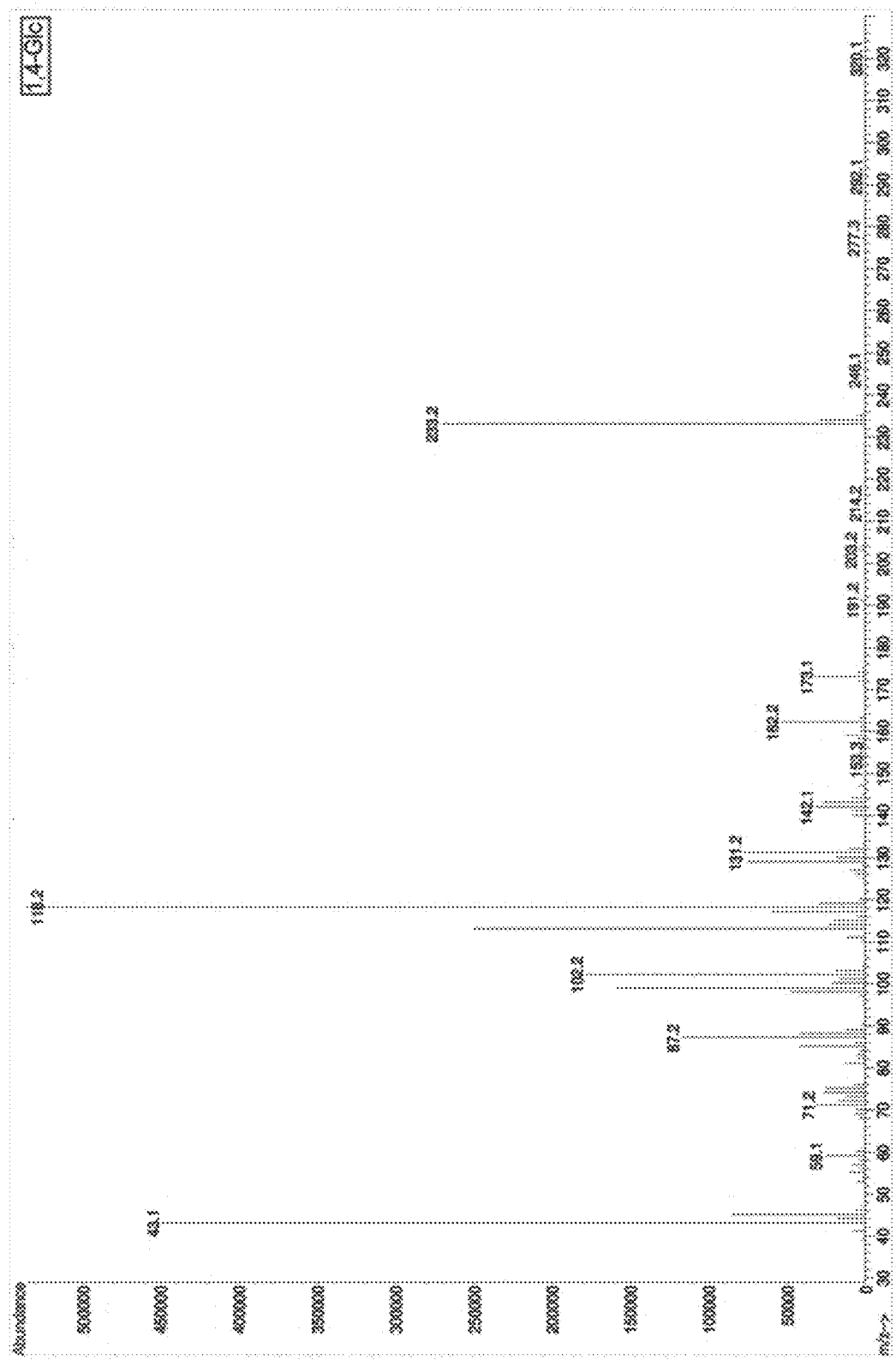
Figure 8B:
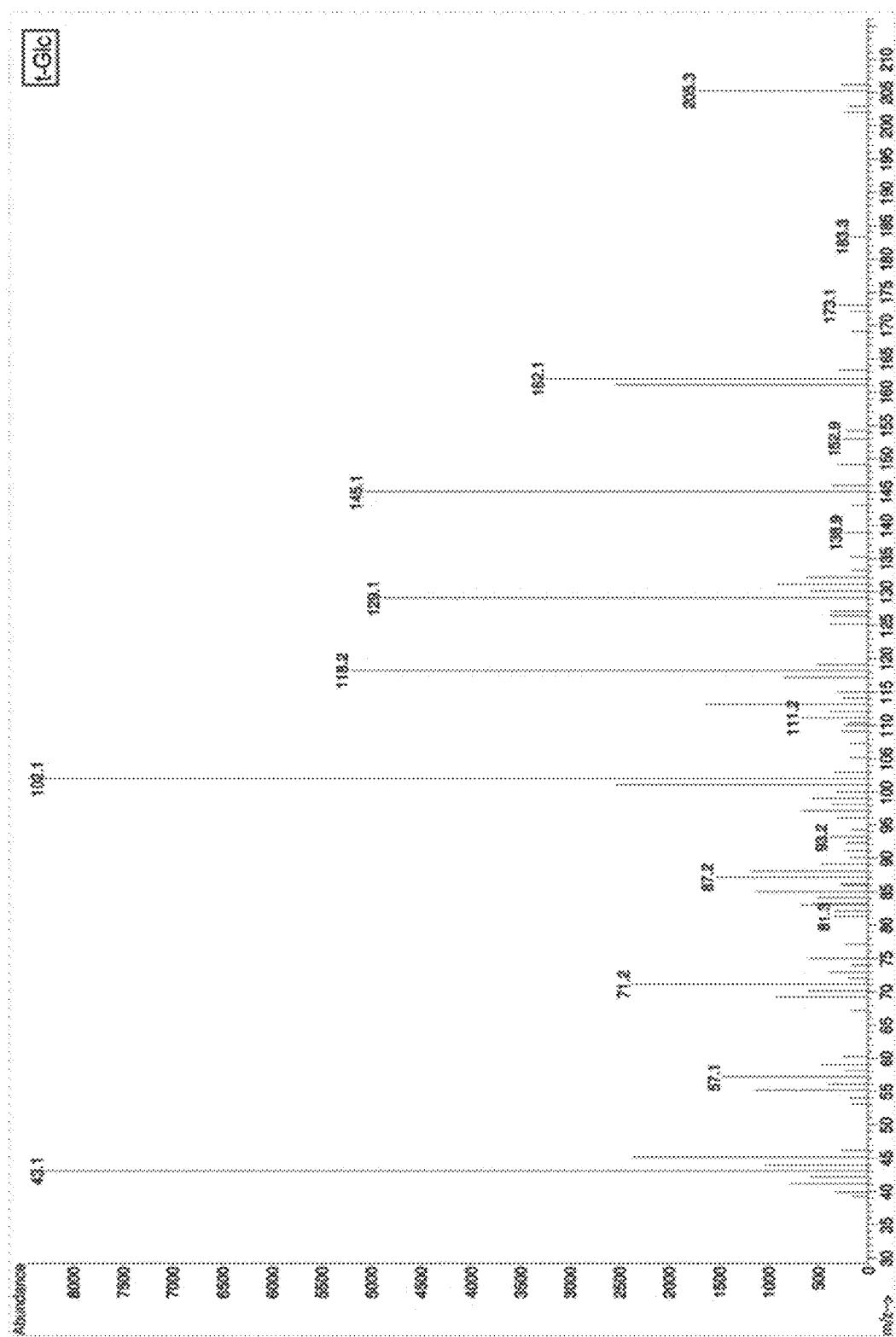
Figure 9A:
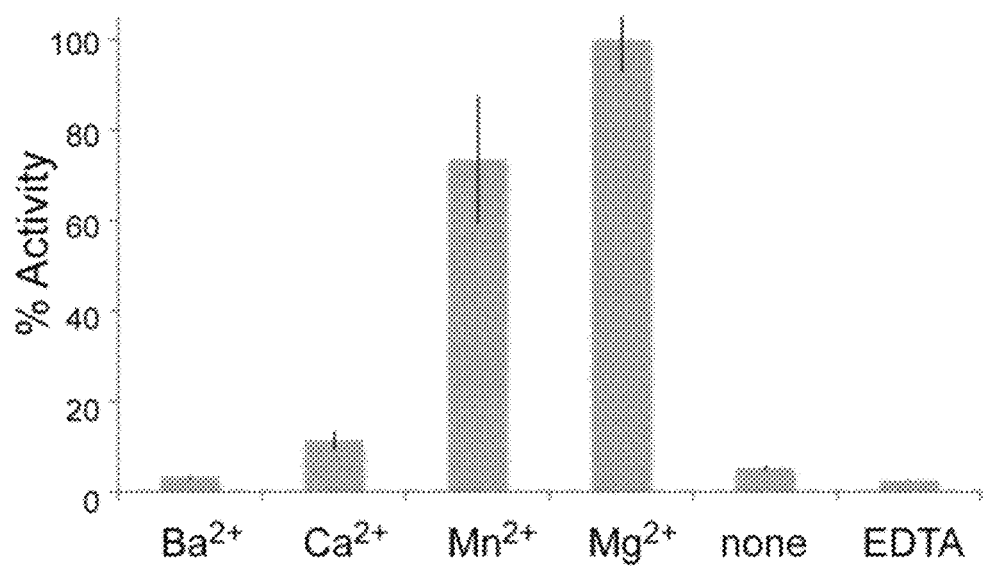
FIG. 9A-9B (also referred to as Example 1, Supplementary FIG. 3): Cation selectivity and pH optimum of cellulose synthase.
Figure 9B:
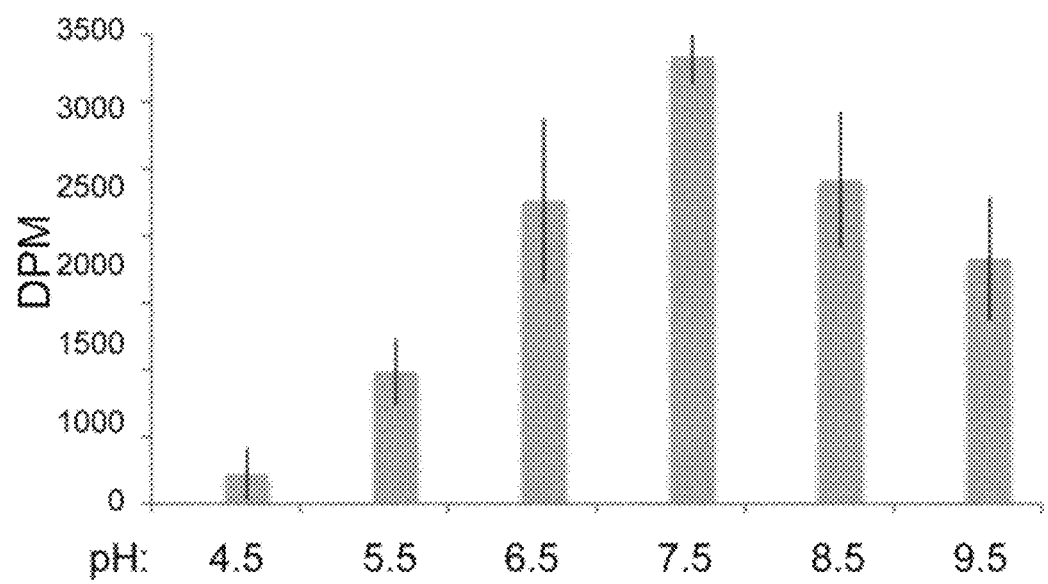
Figure 10A:
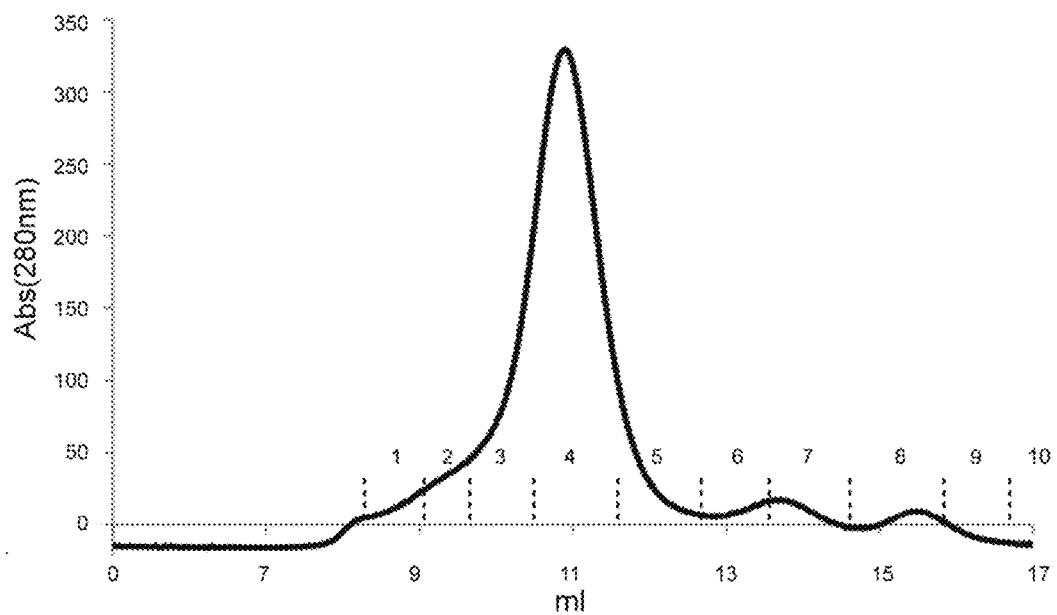
FIG. 10A-10B (also referred to as Example 1, Supplementary FIG. 4): Reconstitution of BcsA-B into lipid nanodiscs. 30 µM of the purified BcsA-B complex was incubated with 120 µM purified apo-A1 protein MSP in the presence of 1 mg/ml detergent-solubilized E. coli total lipid extract. After detergent removal by addition of SM-2 BioBeads, the NDs were purified by gel filtration chromatography over an analytical 5200 Superdex size-exclusion chromatography column (FIG. 10A top panel) in 20 mM Tris pH 7.5, 100 mM NaCl, 5 mM cellobiose and 10% glycerol. The eluted fractions were analyzed by SDS-PAGE and Coomassie staining (FIG. 10B; bottom panel), pooled and concentrated to 5 µM.
Figure 10B:
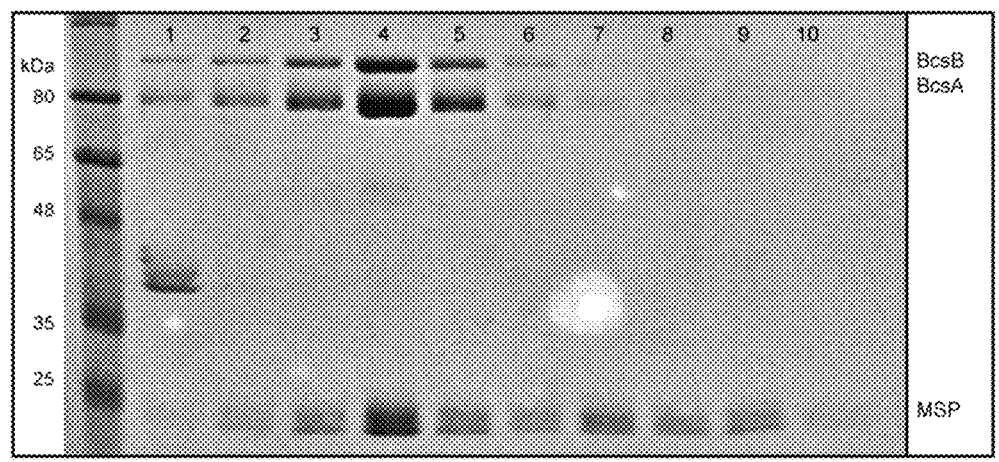
Figure 11:
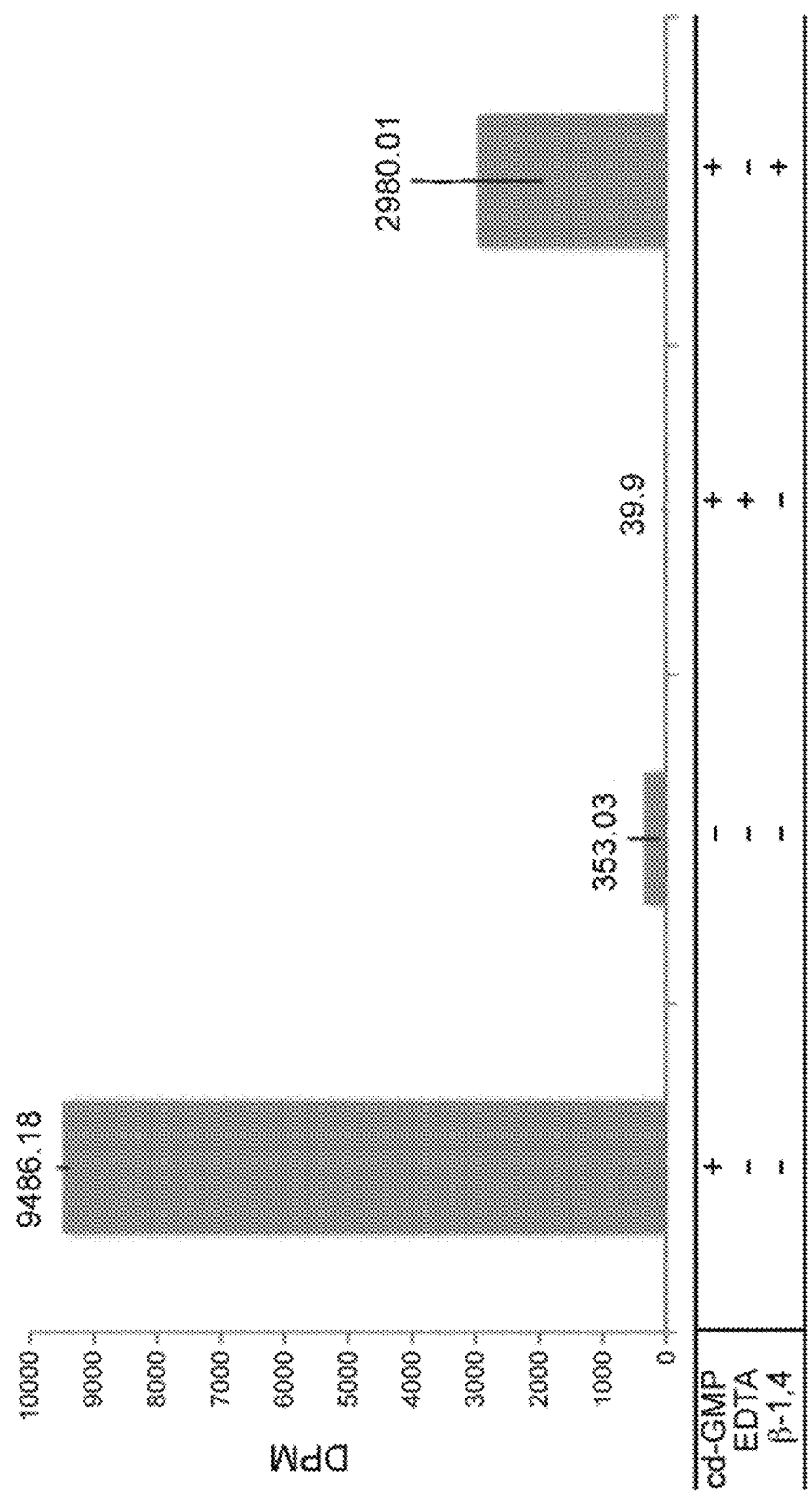
FIG. 11 (also referred to as Example 1, Supplementary FIG. 5): Nanodiscs provide a native-like environment for BcsA-B. Nanodiscs containing the purified BcsA-B complex were incubated at 0.5 µM for 60 min at 37° C. with 5 mM UDP-Glc and 0.03 mM c-di-GMP as described for the PL-reconstituted complex. No product is formed in the presence of 20 mM EDTA. After synthesis, the polymer can be digested with 0.1 mg/ml β-1,4 cellulase from *Aspergillus niger* (β-1,4). The synthesized, $^3$H-labeled polymer was quantified as described in Materials and Methods.
Figure 12:
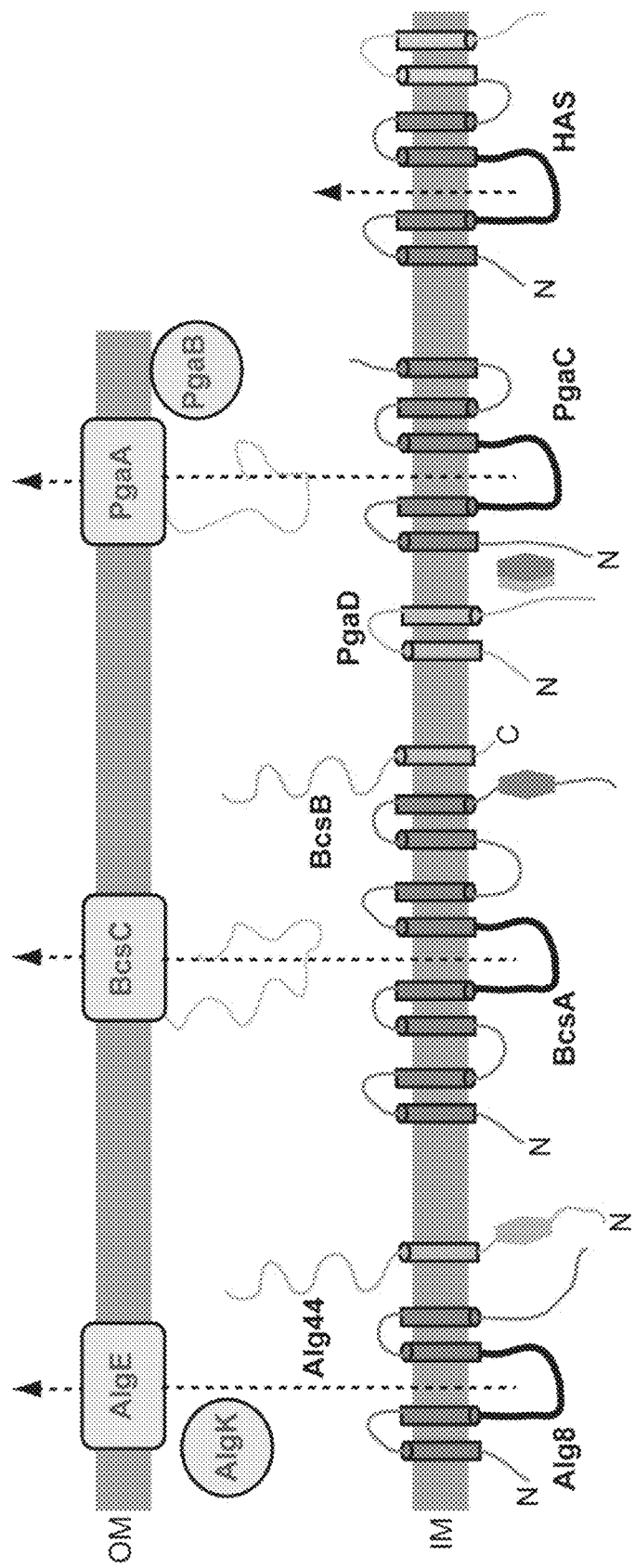
FIG. 12 (also referred to as Example 1, Supplementary FIG. 6): Comparison of bacterial exopolysaccharide synthases. The biosynthesis of bacterial alginate, cellulose and poly-β-1,6 N-acetylglucosamine is activated by c-di-GMP, whereas hyaluronan (HA) formation is independent of c-di-GMP. c-di-GMP-binding domains (green and khaki hexagons) can either be a part of the catalytic subunits (shown in green) or are localized in associating subunits that interact with the synthases, as shown for BcsA and BcsB and Alg44 and Alg8, respectively. PgaC and -D bind c-di-GMP at their interface and do not contain PilZ domains. The GT domains are shown in black and the periplasmic and outer-membrane components required for activity in vivo are shown in gray. Predicted TM segments are shown as cylinders. Hyaluronan synthase (HAS) is predicted to contain four to six TM helices (shown in dark and light green) and is sufficient for HA synthesis and membrane translocation. IM, OM: Inner- and outer membrane.
Figure 25:
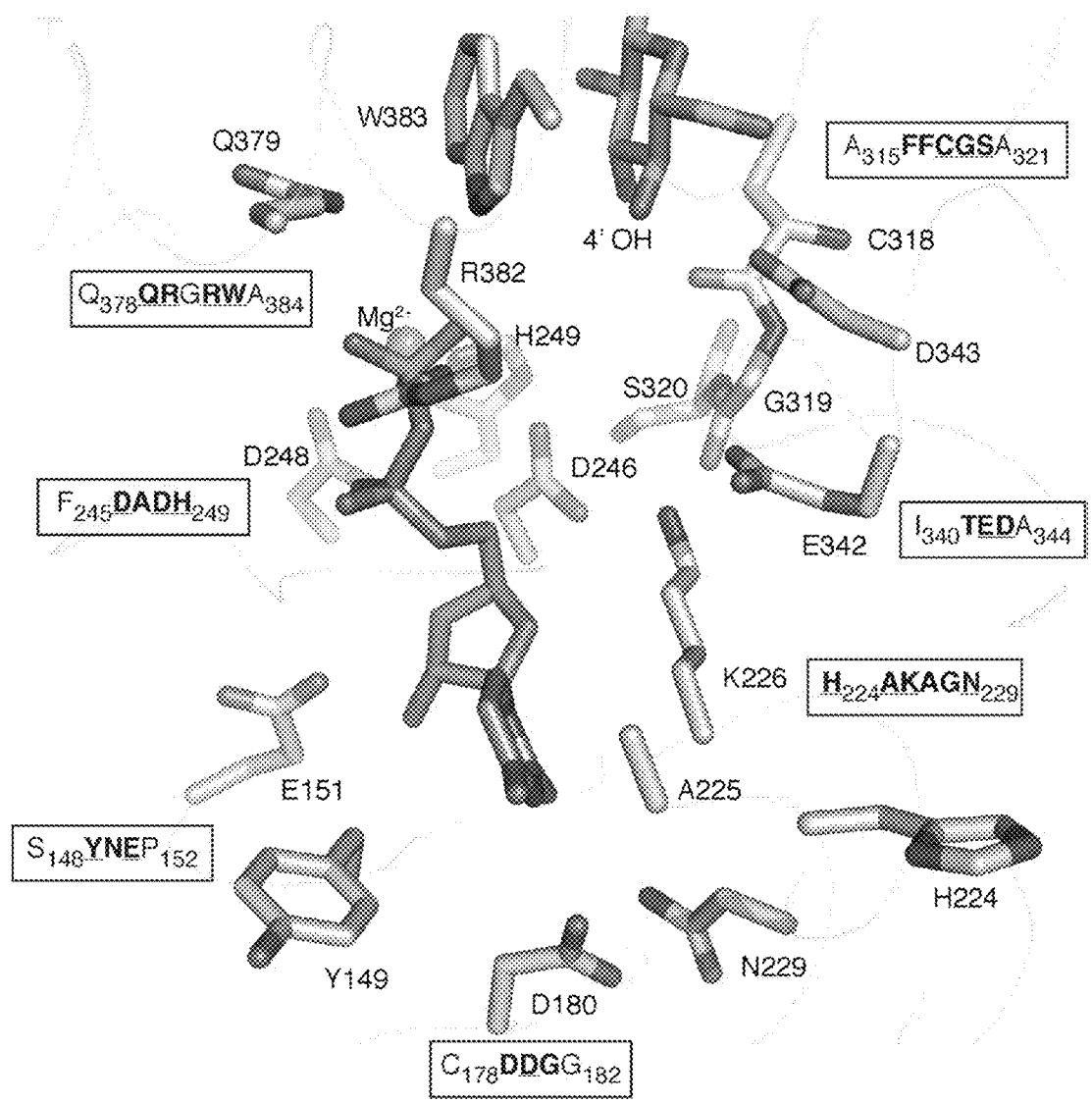

FIG. 25 (also referred to as Example 2, Supplementary FIG. 7): Active site signature motifs involved in donor and acceptor coordination. Conserved residues are shown in sticks. The acceptor glucose is stabilized by interactions with Trp383 belonging to the "QxxRW" motif as well as the backbone carbonyl of Cys318 of the "FFCGS" motif. Residues in BcsA's gating loop that also contact UDP (FIG. 5B) have been omitted for clarity.

DETAILED DESCRIPTION

Abbreviations and Acronyms

BcsA—bacterial cellulose synthase A
BcsA-B—complex of BcsA and BcsB
BcsB—bacterial cellulose synthase B
CBD—carbohydrate-binding domain
c-di-GMP-cyclic-di-GMP (also referred to as cyclic diguanylate and cyclic dimeric guanosine monophosphate)
CesA—cellulose synthase A
LFCE14—LysoFosCholine Ether 14
GMP—guanosine monophosphate
GT—glycosyltransferase
HMW—high molecular weight
IMV—inverted membrane vesicle
LDH—lactate dehydrogenase
ND—nanodisc
PelB—pectate lyase B
PEP—phosphoenolpyruvate
PK—pyruvate kinase
PL—proteoliposome
TM—transmembrane
UDP—uridine diphosphate
UDP-Glc—UDP-glucose

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

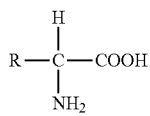

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

As used herein, the term "biologically active fragments" or "bioactive fragment" of the polypeptides encompasses natural or synthetic portions of the full-length protein that are capable of specific binding to their natural ligand or of performing the function of the protein.

As used herein, the term "biologically active fragments" or "bioactive fragment" of the polypeptides encompasses natural or synthetic portions of the full-length protein that are capable of specific binding to their natural ligand or of performing the function of the protein.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene, which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region, which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand, which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, a "derivative" of a compound, when referring to a chemical compound, is one that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains. As used herein, the term "effector domain" refers to a domain capable of directly interacting with an effector molecule, chemical, or structure in the cytoplasm which is capable of regulating a biochemical pathway.

The term "downstream" when used in reference to a direction along a nucleotide sequence means the 5' to 3' direction. Similarly, the term "upstream" means the 3' to 5' direction.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

By "equivalent fragment" as used herein when referring to two homologous proteins from different species is meant a fragment comprising the domain or amino acid being described or compared relative to the first protein, such as a Bcs protein of *Rhodobacter sphaeroides* compared to that of a Bcs protein in another bacterial species.

As used herein, an "essentially pure" preparation of a particular protein or peptide is a preparation wherein at least about 95%, and preferably at least about 99%, by weight, of the protein or peptide in the preparation is the particular protein or peptide.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein the term "expression" when used in reference to a gene or protein, without further modification, is intended to encompass transcription of a gene and/or translation of the transcript into a protein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein, an "instructional material" includes a publication, a recording, a diagram, or any other medium of expression which can be used to communicate the usefulness of the peptide of the invention in the kit. The instructional material of the kit of the invention may, for example, be affixed to a container which contains the identified compound(s) invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc., and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

A "mutation" as used herein can be natural or synthetic.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "peptide" typically refers to short polypeptides.

The term "per application" as used herein refers to administration of a compositions, drug, or compound to a subject.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

By "purified bacterial components" is meant proteins purified from bacteria or purified proteins made using bacterial protein sequences.

By "synthesis in vitro" is meant cellulose synthesis that is not occurring in a cell, although it does not exclude synthesis where cellular components are added or the use of cells that either do not have their own endogenous cellulose synthetic machinery or cells that no longer have such machinery.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates. The terms "protein pathway" and "protein regulatory pathway" are used interchangeably herein.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

The term "regulate" refers to either stimulating or inhibiting a function or activity of interest.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially similar nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 96%, 97%, 98%, 99% or more. Substantial similarity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "transfection" is used interchangeably with the terms "gene transfer", "transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

The term "transgene" is used interchangeably with "inserted gene," or "expressed gene" and, where appropriate, "gene". "Transgene" refers to a polynucleotide that, when introduced into a cell, is capable of being transcribed under appropriate conditions so as to confer a beneficial property to the cell such as, for example, expression of a therapeutically useful protein. It is an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, a "transgenic cell" is any cell that comprises a nucleic acid sequence that has been introduced into the cell in a manner that allows expression of a gene encoded by the introduced nucleic acid sequence. In a bacteria, the cell can be termed a transformed cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

EMBODIMENTS

Fragments of SEQ ID NO:1 (BcsA; 788 a.a. residues) include, for example, fragments comprising residues 1-787, 1-786, 1-785, etc. down to about residues 1-15. Fragments further include those of about residue positions 2-788, 20-788, 40-788, 100-788, 200-788, 250-788, 300-788, 350-788, 400-788, 450-788, 500-788, 550-788, 600-788, 650-788, 700-788, and 750-788. They also include fragments having a size of about 10 amino acids in length, 15, 20, 25, 35, 50, 75, 100, 125, 150, 175, 200, 250, 275, 300, 350, 400, 450, 500, 550, 600, 650, 700, 750, etc., up to about 787 amino acid residues in length. One of ordinary skill in the art will know which fragment to use or test based on the desired activity.

Fragments of SEQ ID NO:3 (Rhodobacter sphaeroides BcsB; 725 a.a. residues) include, for example, fragments comprising residues 1-724, 1-723, 1-722, etc. down to about residues 1-15 of BcsB. However, the main activity resides in the C-terminus, so preferable fragments will include those comprising about residues 500-725, 550-725, 600-725, 650-725, 675-725 and 684-725 (SEQ ID NO:4) of BcsB. Fragments further include those of about residue positions 2-725, 20-725, 40-725, 100-725, 200-725, 250-725, 300-725, 350-725, 400-725, 450-725, 500-725, 550-725, 600-725, 650-725, 700-725, and 750-725 residues in length. They also include fragments having a size of about 10 amino acids in length, or 15, 20, 25, 35, 50, 75, 100, 125, 150, 175, 200, 250, 275, 300, 350, 400, 450, 500, 550, 600, 650, 700, etc., up to about 724 amino acid residues in length. One of ordinary skill in the art will know which fragment to use or test based on the desired activity. Additionally, the invention encompasses the use of BscB from other bacteria, as well as hybrid BcsB proteins comprising sequences from more than one bacteria. For example, SEQ ID NO:5 is a Rhodobacter sphaeroides and E. coli hybrid of 729 amino acid residues. Useful fragments of SEQ ID NO:5 include, for example, fragments comprising residues 1-728, 1-727, 1-726, etc. down to about residues 1-15 of BcsB SEQ ID NO:5. However, the main activity resides in the C-terminus, so preferable fragments will include those comprising about residues 500-729, 550-729, 600-729, 650-729, 675-729 and 684-729 of BcsB SEQ ID NO:5. Fragments further include those of about residue positions 2-729, 20-729, 40-729, 100-729, 200-729, 250-729, 300-729, 350-729, 400-729, 450-729, 500-729, 550-729, 600-729, 650-729, 700-729, and 750-729 residues in length. They also include fragments having a size of about 10 amino acids in length, or 15, 20, 25, 35, 50, 75, 100, 125, 150, 175, 200, 250, 275, 300, 350, 400, 450, 500, 550, 600, 650, 700, etc., up to about 724 amino acid residues in length. One of ordinary skill in the art will appreciate that BcsB proteins from other species can be used as well and that the size of fragments with the desired activity can be easily determined.

Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

Although the present invention provides "in vitro" synthesis of cellulose using purified bacterial synthases, the present invention further includes the use of additional materials and use of the synthesis compositions and methods in not just a cell-free environment, but with cells as well. As disclosed herein, cellular components such as inverted membranes can be used. One of ordinary skill in the art will appreciate that a support can also be used, as demonstrated by the use of nanodiscs herein. The present invention encompasses the use of other supports and attachment substrates as well. These can include chromatography materials where various components can be mixed or for example can be passed by the attached components in an elution/flow process or a large chamber or device where materials can be combined, stirred, etc., as well as used for separation or elution methods. Regarding the use of additional cellular components or cells, the invention encompasses more than just the membrane mimetics disclosed herein. In one aspect, a membrane mimetic is not needed if a cell is used or other substrate or support is used. In one aspect, the support is a solid support.

The present invention further encompasses the use of host cells for making cellulose wherein cells are selected that do not have endogenous cellulose synthetic genes or which have been altered to not express them. The cells can be transformed with a vector or plasmid comprising nucleic acid sequences encoding BcsA and BcsB proteins, or biologically active fragments or homologs thereof. The genes can include promoters for regulating how BcsA and BcsB are expressed. The transformed cells comprising BcsA and BcsB can be used to synthesize cellulose according to practices used for other cells to produce various products that can then be isolated and purified from the growth medium, etc.

One of ordinary skill in the art will appreciate that BcsA and BcsB genes and proteins from other cells can be used in the practice of the invention. For example, cellulose synthase genes from essentially all bacterial sources that have them can be used. The genes are all fairly conserved, hence the mutagenesis of the invention should also work (mutating the R580 to Ala) in the other genes and proteins from other bacteria comprising such genes. In the present invention, the position of the mutation generating a constitutively active enzyme (R580 in *Rhodobacter* to Ala) corresponds to residue 580 only in *Rhodobacter*. In other homologues the residue number will be different, however the consensus motif will be the same (referred to as a "RxxxR" motif; see Examples) as the R580 in *Rhodobacter* and would be the first R. In other words, the sequence motif is the same in all BcsAs, however the residue number will be different.

The present invention further encompasses methods to scale up the synthesis and production of cellulose. In one embodiment, the expression host (see *E. coli* in the Examples) can be grown in a fermenter to high cell densities. In one aspect, this should also increase the cellulose yield. Additionally, other bacteria could be used, such as cyanobacteria. In addition, the expression levels of the BcsA-B complex could be improved by codon optimizing the DNA sequences for expression in *E. coli* (or whatever other host chosen), optimizing the protein induction method (IPTG versus auto-induction media, as in the present application) and optimizing the induction time and incubation temperature. Additionally, the leader/signal sequence of the BcsB protein can be modified for the particular host.

Also included are peptides and polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

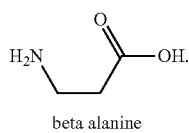

beta alanine

Sequences are provided herein which use the symbol "βA", but in the Sequence Listing submitted herewith "βA" is provided as "Xaa" and reference in the text of the Sequence Listing indicates that Xaa is beta alanine.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.
Amino Acid Substitutions In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

In another embodiment disclosed herein, peptide longevity is enhanced by the addition of adducts such as sucrose or polyethylene glycol, production of peptide-IgG chimeras, or the peptides can be cyclized via cysteine-cysteine linkages, which is a modification known to enhance the biological activities of a variety of peptides.

In one aspect a polyethylene glycol adduct is (2-aminoethyl)-O'—(N-diglycolyl-2-aminoethyl)-hexaethyleneglycol. In another aspect of the invention, a polyethylene glycol adduct is in the form of GK[(2-aminoethyl)-O'—(N-diglycolyl-2-aminoethyl)-hexaethyleneglycol]GG. The dipeptide GK increases peptide solubility. The dipeptide GG is present as a spacer between the solid support and peptide chain to improve the ease of peptide synthesis.

The present disclosure also contemplates any of the peptides derivatized with functional groups and/or linked to other molecules to facilitate their delivery to specific sites of action, to potentiate their activity, or complexed covalently or non-covalently to other pharmaceuticals, bioactive agents, or other molecules. Such derivatizations must be accomplished so as to not significantly interfere with the properties of the peptides. Carriers and derivatizations must also be designed or chosen so as not to exert toxic or undesirable activities on animals or humans treated with these formulations. Functional groups which may be covalently linked to the peptides may include, but not be limited to, amines, alcohols, or ethers. Functional groups to be covalently linked to the peptides to increase their in vivo half-lives may include, but not be limited to, polyethylene glycols, small carbohydrates such as sucrose, or peptides and proteins. The peptides may also be synthesized by recombinant DNA techniques with expression vectors for use in biological systems, such as bacteria, yeast, insect, or mammalian cells.

A composition of the invention may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The invention further includes isolated nucleic acids comprising sequences encoding proteins or peptides of the invention.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The invention further provides a kit comprising one or more peptides or expression vectors of the invention, an applicator, an instructional material for the use thereof.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans can be easily determined by a person skilled in the art.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

Example 1: BcsA and BcsB Form the Catalytically Active Core of Bacterial Cellulose Synthase Sufficient for In Vitro Cellulose Synthesis Results BcsB is Required for Catalytic Activity of BcsA Gram-negative bacteria transport cellulose across the inner and outer bacterial membranes. Most likely this is achieved by associating the catalytic BcsA-B complex in the inner membrane with the pore-forming outer membrane BcsC subunit. To identify the complex components required for cellulose synthesis and translocation across the inner bacterial membrane, we expressed BcsA and BcsB from *Escherichia coli* (Ec) K12 and *Rhodobacter sphaeroides*

(Rs) in *E. coli* C43 (28), prepared inverted membrane vesicles (IMVs), and analyzed them for cellulose synthesis activity. To this end, the membrane vesicles were incubated at 37° C. with the substrate UDP-Glc, the activator c-di-GMP, as well as 3H-labeled UDP-Glc as a radiotracer. The reaction was terminated upon addition of 2% SDS and the water-insoluble, HMW polymer was sedimented by centrifugation. Subsequently, the obtained product was further purified by descending paper chromatography (1) and quantified by scintillation counting. FIG. 1 shows that only IMVs containing BcsA and BcsB produce a HMW polymer. IMVs containing only BcsA or BcsB are catalytically inactive. Combining IMVs containing BcsA or BcsB does not restore catalytic activity, suggesting that both subunits have to be in the same membrane to form a functional complex (FIGS. 1A and B). Polymer synthesis strictly depends on the presence of c-di-GMP as well as Mg2+, as expected for bacterial cellulose synthesis.

BcsB carries an N-terminal secretion signal sequence and, depending on the species, has a predicted molecular weight of 75 to 83 kDa after signal peptide cleavage. Under non-reducing conditions, BcsB migrates at approximately 100 kDa on an SDS-PAGE. Upon reduction, however, BcsB's electrophoretic mobility significantly increases, suggesting that the protein forms an intramolecular disulfide bond (FIG. 1C). Indeed, most BcsBs contain only two invariant Cys residues (FIG. S1), one in each CBD, which are in close proximity to one another at the CBD interface (2).

Purified BcsA-B Synthesizes High-Molecular-Weight Cellulose

Figure 2A:
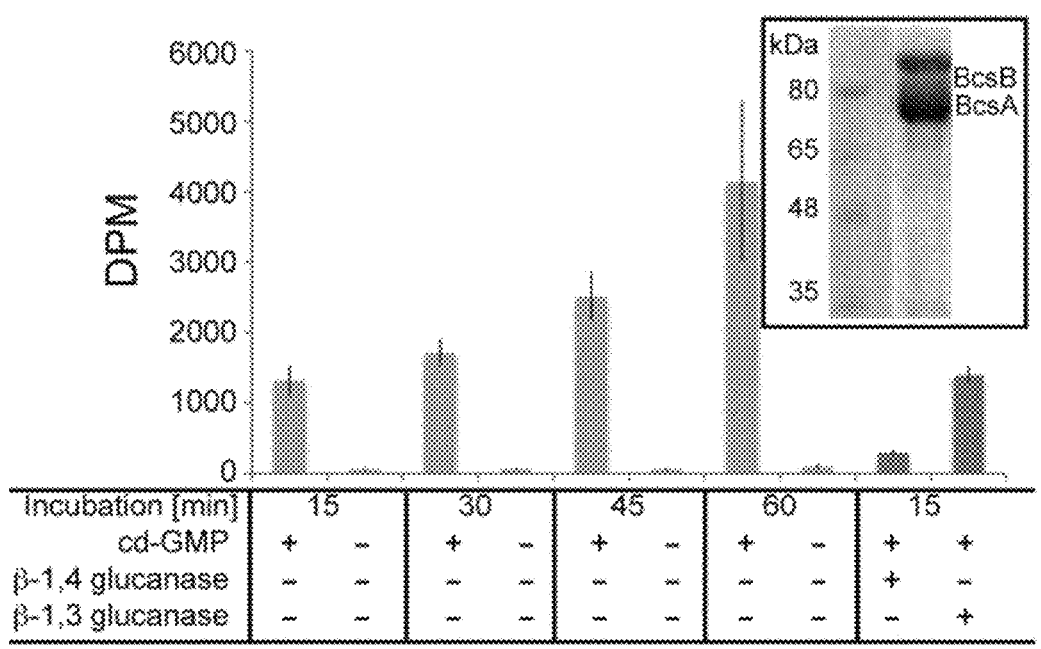
FIG. 2A-2B (also referred to as Example 1, FIG. 2): Activity of purified and reconstituted BcsA-B and linkage analysis of the corresponding product synthesized in vitro.

The Rs BcsA-B complex was purified to homogeneity in the detergent LysoFosCholine Ether 14 (LFCE14) via metal affinity and gel filtration chromatography and was reconstituted into PLs formed from *E. coli* total lipid extract. In PLs, the cellulose synthase activity displays a similar dependence on activation by c-di-GMP as in IMVs, suggesting that the complex retained its native-like activity during purification (FIG. 2A).

Figure 2B:
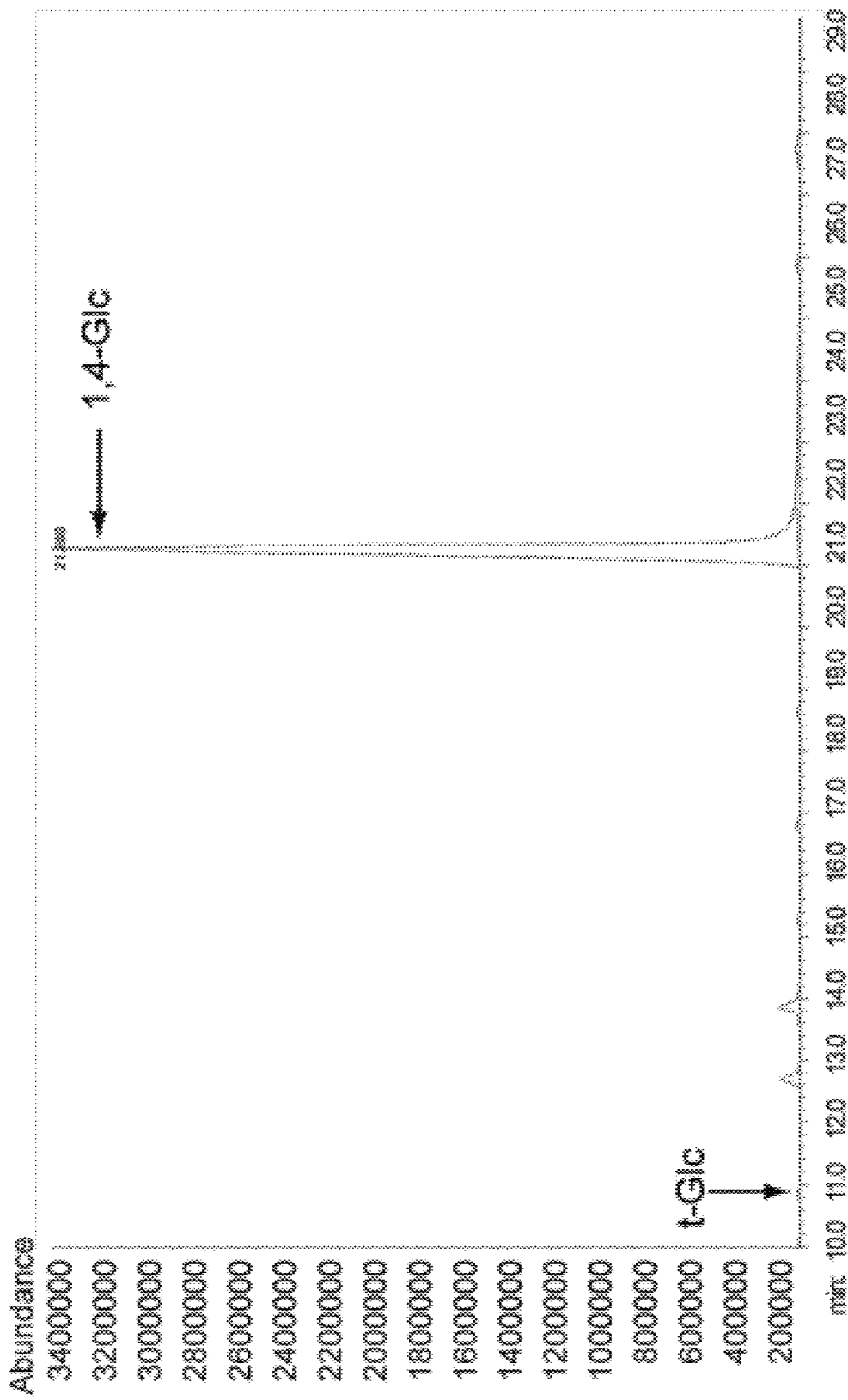

To further confirm that the synthesized polymer represents a β-1,4-linked glucan, we tested whether a β-1,4 or β-1,3 specific endo glucanase degrades the water-insoluble polymer. As expected for cellulose, β-1,3 glucanase does not degrade the synthesized polymer while β-1,4 glucanase does (FIG. 2A). In addition, permethylation glycosyl linkage analysis of the glucan obtained from a 60-min synthesis reaction reveals that the in vitro synthesized polymer consists exclusively of 1,4-linked glucosyl residues (FIGS. 2B and S2). The alditolacetates corresponding to the residues at the non-reducing ends of the chains represent no more than 0.3-0.5% of the total derivatives obtained from the in vitro product (FIG. 2B). Altogether, these data confirm the cellulosic nature of the polysaccharide formed by the BcsA-B complex and indicate that the chains formed in vitro exhibit a degree of polymerization of at least 200, most likely within the range 200-300.

Most inverting GT require an essential divalent cation for catalysis. The cation is coordinated by a conserved Asp-X-Asp motif at the active site to stabilize the nucleoside diphosphate leaving group during glycosyl transfer (2, 29). To determine cation preference, cellulose synthesis reactions were performed in the presence of Ba2+, Mn2+, Mg2+, and Ca2+. Only Mn2+ and Mg2+ enabled approximately equal activity levels (FIG. S3A), consistent with earlier observations on other processive GT (30, 31). To facilitate glycosyl transfer, the acceptor 4' hydroxyl group of the growing polysaccharide becomes deprotonated during the SN2 nucleophilic substitution reaction (32). Based on the crystal structure of Rs BcsA-B, the general base catalyzing deprotonation (Asp343) is part of an invariant Thr-Glu-Asp motif within hydrogen bond distance to the non-reducing end of the polymer (2). Asp343 lies at the back of a deep substrate-binding groove between the donor and acceptor coordination sites. Cellulose synthesis assays performed in a pH range from 4.5 to 9.5 show that BcsA-B exhibits optimal activity at neutral pH (FIG. S3B), yet significant activity remains even at an alkaline pH of 9.5. This pH profile is consistent with a buried carboxylate as a catalytic base (33).

Kinetic Characterization and Activation of Cellulose Synthesis by c-di-GMP

The GT reaction catalyzed by BcsA transfers the donor glucose from the donor substrate UDP-Glc to the non-reducing end of the acceptor glucan as also observed for plant and other bacterial CesAs (25, 26, 34). Thus, the second product of the cellulose synthase reaction is UDP. To confirm that BcsA indeed forms UDP as a reaction product (and not, for example, UMP plus inorganic phosphate) and to obtain kinetic insights into cellulose synthesis, we coupled cellulose synthesis to the activities of pyruvate kinase (PK) and lactate dehydrogenase, thus monitoring polymer formation in real time by following the oxidation of reduced nicotinamide adenine dinucleotide (NADH) spectrophotometrically (1, 35). Because PK recognizes UDP but not UMP as substrate (36), the successful coupling of cellulose synthesis with its activity implies the formation of UDP. To ensure that all BcsA-B complexes are accessible to the substrates and can contribute to the observed reaction, the complex was reconstituted into lipid nanodiscs (ND) (FIG. S4), which are edge-stabilized, planar lipid bilayer discs approximately 10 nm in diameter (37). At this size, each ND most likely contains a single BcsA-B complex (38).

Figure 3A:
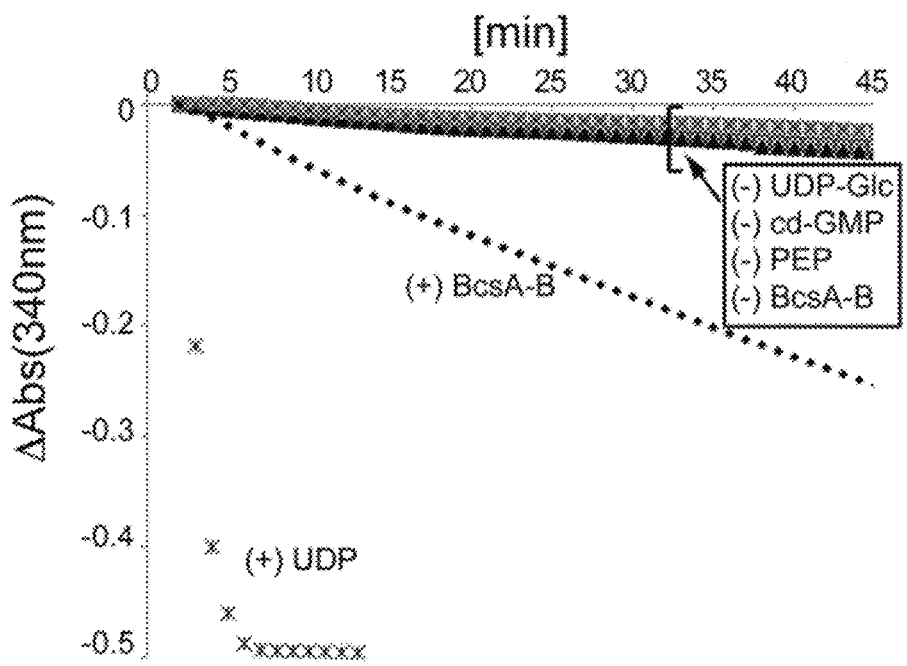
FIG. 3A-3D (also referred to as Example 1, FIG. 3): Kinetic analysis of cellulose synthesis and stimulation by cyclic-di-GMP.

As in PLs, the activity of BcsA-B in ND strongly depends upon activation by c-di-GMP and the polymer is readily degraded by β-1,4 glucanase, suggesting that ND provide a native-like environment (FIG. S5). As shown in FIG. 3A, the c-di-GMP-activated BcsA-B complex generates UDP at a constant rate for up to 45 min, indicating that the enzyme is not inhibited by the accumulating or aggregating cellulose. No UDP is formed in the absence of c-di-GMP, UDP-Glc or BcsA-B.

Figure 3B:
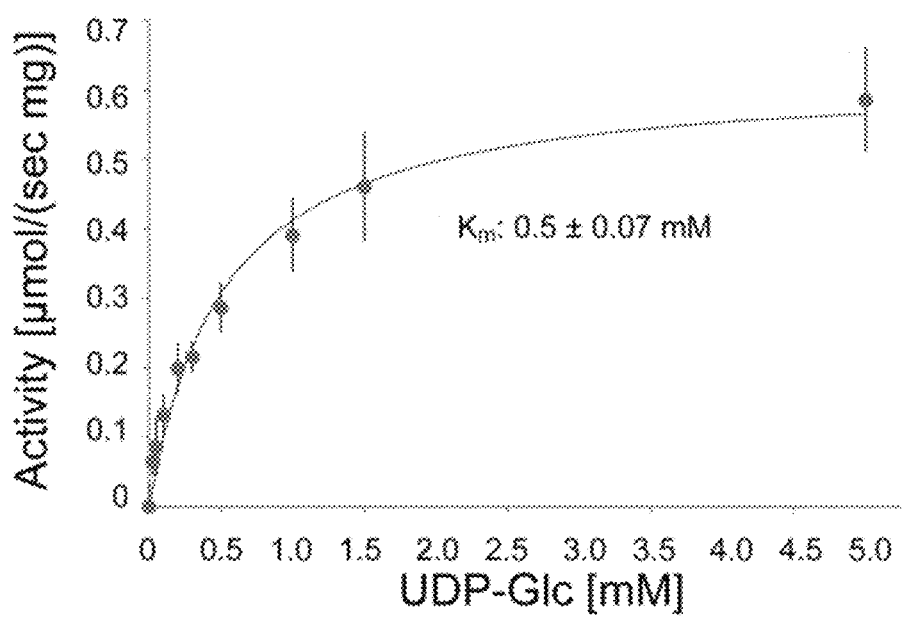
Figure 3C:
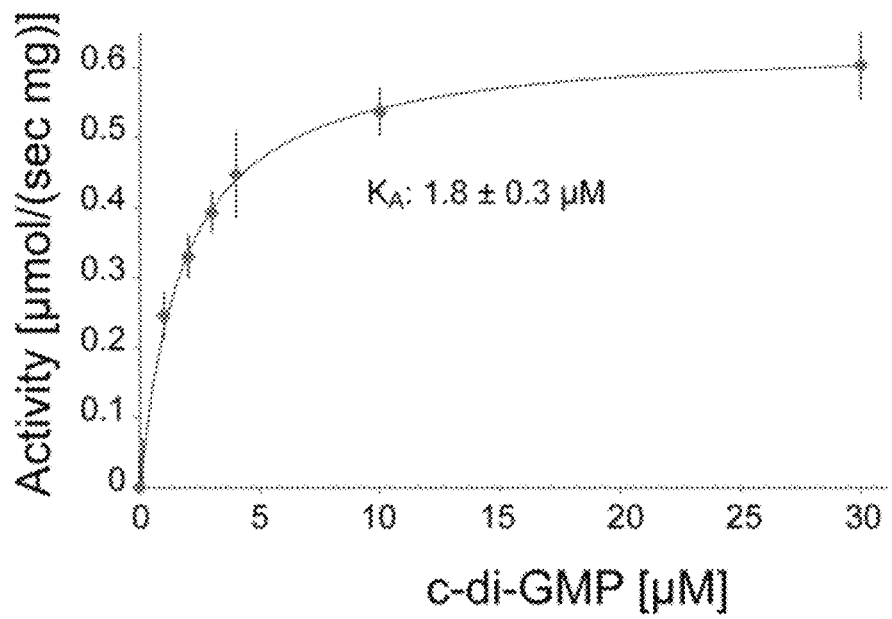
Figure 3D:
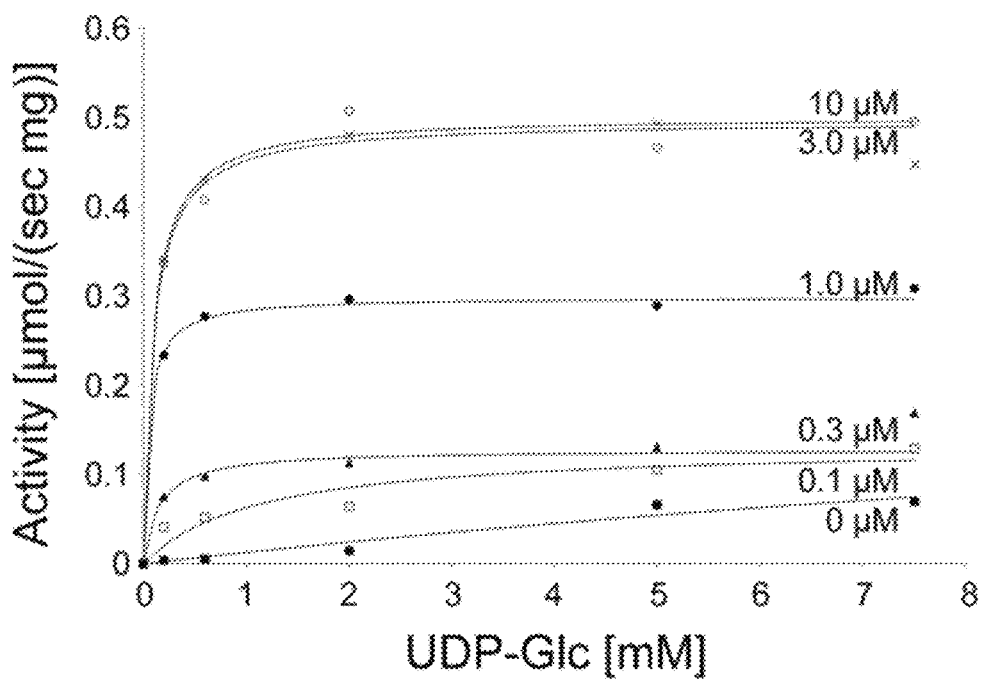

The robust activity of BcsA-B in ND allows analyzing its activity at either varying UDP-Glc or varying c-di-GMP concentrations (FIGS. 3B and C). Under both conditions, the enzyme obeys monophasic Michaelis-Menten kinetics with apparent affinities of 0.5 mM and 1.8 μM for UDP-Glc and c-di-GMP, consistent with the estimated physiological concentrations of 1-2 mM for UDP-Glc and 1-10 μM for c-di-GMP (39, 40). Although the concentration of active BcsA-B in ND is unknown, assuming that 100% of the enzyme is responsible for the observed activity suggests a minimal polymerization rate of approximately 90 UDP molecules per second and BcsA-B complex. This rate is about 10-fold higher than what has been observed in other model systems, perhaps due to the lack of higher-order organization of the synthesized glucan chains (25, 41, 42).

c-di-GMP strongly activates cellulose synthesis by an unknown mechanism (43). The tight association of BcsA's PilZ- and GT domains suggests that c-di-GMP controls the accessibility of the GT active site (2). Titrating UDP-Glc at different c-di-GMP concentrations shows that the maximum catalytic activity achieved depends on the overall c-di-GMP concentration, while the apparent affinity for UDP-Glc remains within 0.1 to 1.0 mM, comparable with the Km of 0.5 mM for UDP-Glc determined in the presence of 30 µM c-di-GMP (FIG. 3B).

Feedback Inhibition of BcsA-B

The reconstituted cellulose biosynthetic activity solely requires the presence of UDP-Glc and the activator c-di-GMP. The cellulose synthesis rate of microfibril-forming, oligomeric CesAs is influenced by the interaction of the individual glucans outside the cell, suggesting that cellulose microfibril formation is rate limiting (42, 44, 45). Thus, we further investigated whether the catalytic rate of BcsA-B is also influenced by the accumulating products, either HMW cellulose or UDP.

BcsZ is a periplasmic cellulose encoded in most bacterial cellulose synthase operons characterized to date (4). Although BcsZ exhibits low activity toward crystalline cellulose microfibrils (20), it efficiently degrades in vitro synthesized cellulose in situ.

Performing cellulose synthesis assays with ND-reconstituted BcsA-B in the presence of 0.1 mg/ml E. coli BcsZ prevents the accumulation of HMW cellulose (FIG. 4A), suggesting that BcsZ efficiently degrades the glucan as it emerges from the complex. Kinetically, however, BcsA-B's apparent reaction rate does not change in the presence of BcsZ, indicating that its activity is not affected by the accumulating polymer (FIG. 4A), perhaps because the emerging glucans lack higher-order organization. This is consistent with the higher apparent polymerization rate of BcsA-B compared to CesAs that form cellulose microfibrils (FIG. 3B) (25, 41, 42). The same results were obtained with PLs-reconstituted BcsA-B, arguing that the lack of product inhibition is not due to a different oligomeric state of the synthase in ND.

Figure 4B:
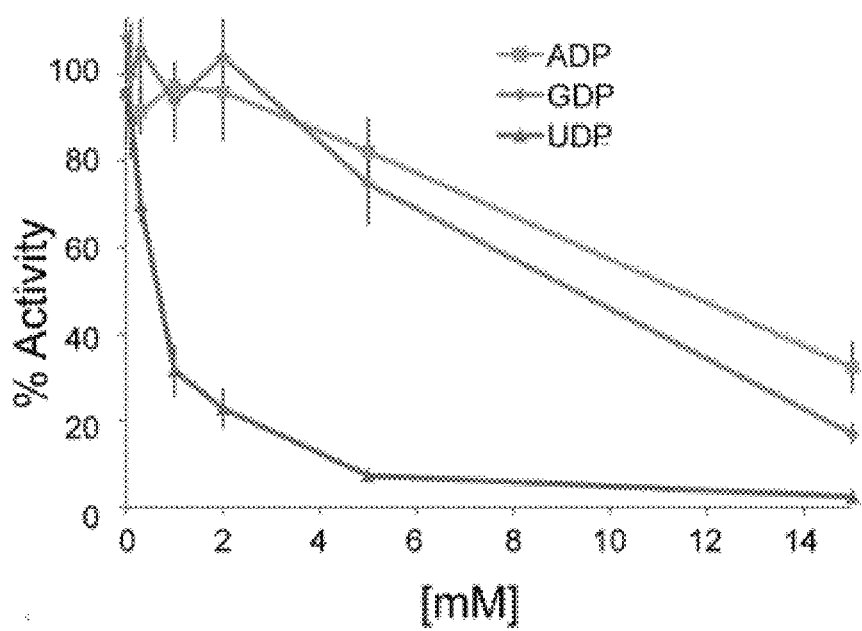
Figure 4C:
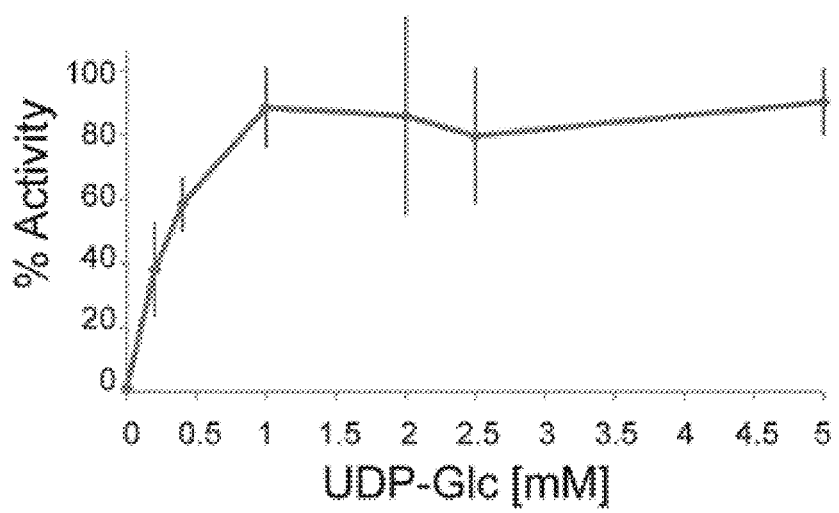

The glycosyl transfer reaction converts UDP-Glc to UDP, thereby releasing an important nucleotide whose physiological concentration is maintained in the low µM range (39). To analyze whether BcsA-B undergoes feedback inhibition by UDP, we first tested BcsA-B's activity in the presence of a constant 0.5 mM UDP-Glc concentration and increasing concentrations of UDP by the cellulose sedimentation assay. BcsA-B's activity is significantly inhibited by UDP, with only 50% of product formed in the presence of 0.7 mM UDP (FIG. 4B). In contrast, guanosine- and adenosine-diphosphates do not inhibit cellulose synthesis. However, inhibition by UDP is competitive as the enzyme reaches normal activity levels with increasing UDP-Glc to UDP ratios (FIG. 4C), suggesting a model by which UDP, at high concentration, competitively competes with UDP-Glc for binding to BcsA's active site. Under physiological conditions, however, it is unlikely that this inhibitory effect becomes rate limiting as the concentration of UDP-Glc exceeds that of UDP by about an order of magnitude (39).

Substrate Specificity of BcsA-B

Figure 5A:
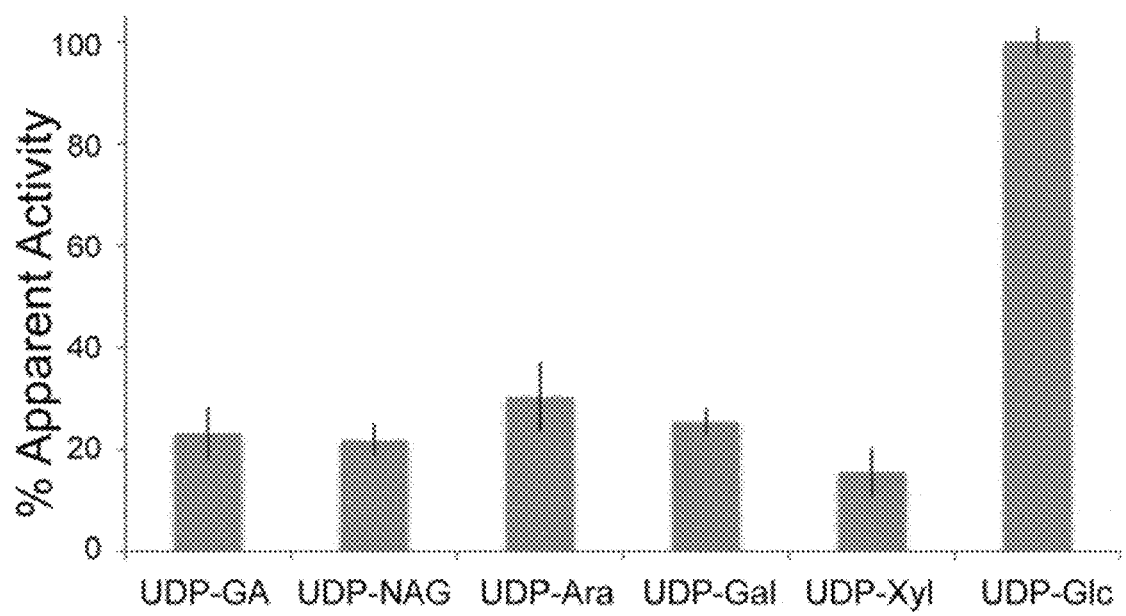
FIG. 5A-5D (also referred to as Example 1, FIG. 5): Substrate specificity of BcsA-B.

It is unknown how cellulose synthases select their substrate UDP-Glc. Several UDP-activated sugars are common precursors for many physiological processes in pro- and eukaryotes and substrate promiscuity is predicted to change the physico-chemical properties of the polymer formed or even terminate polymerization. In order to probe the substrate specificity of BcsA-B, we performed enzyme-coupled cellulose synthesis reactions in the presence of 5 mM UDP-galactose (Gal), -glucuronic acid (GA), -N-acetyl glucosamine (NAG), -arabinose (Ara) or -xylose (Xyl) as the only carbohydrate source. As shown in FIG. 5A, none of the alternative substrates enables a reaction rate similar to UDP-Glc, giving rise to about 20% residual activity compared to the non-stimulated state in the absence of c-di-GMP, perhaps due to slow incorporation or hydrolysis of the alternative UDP-sugars.

Figure 5B:
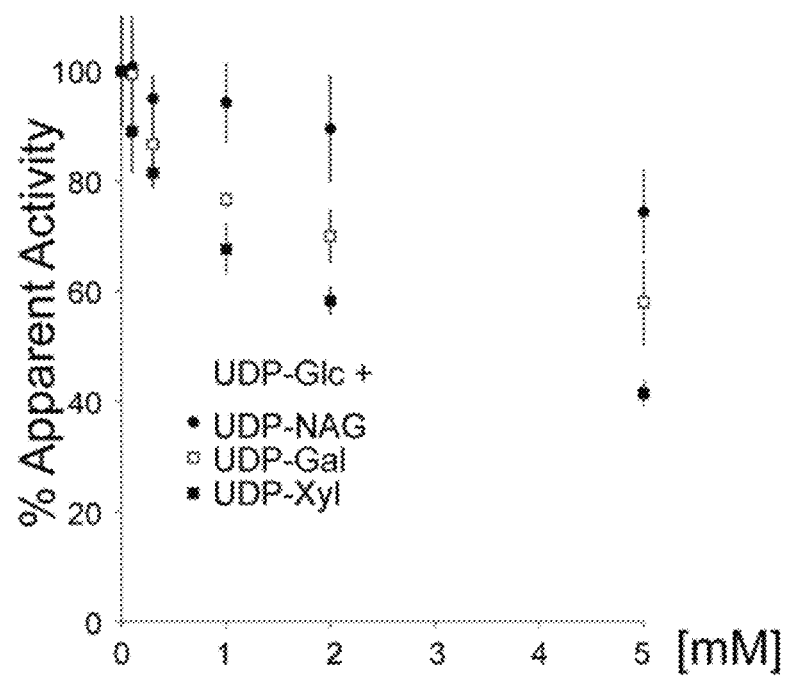
Figure 5C:
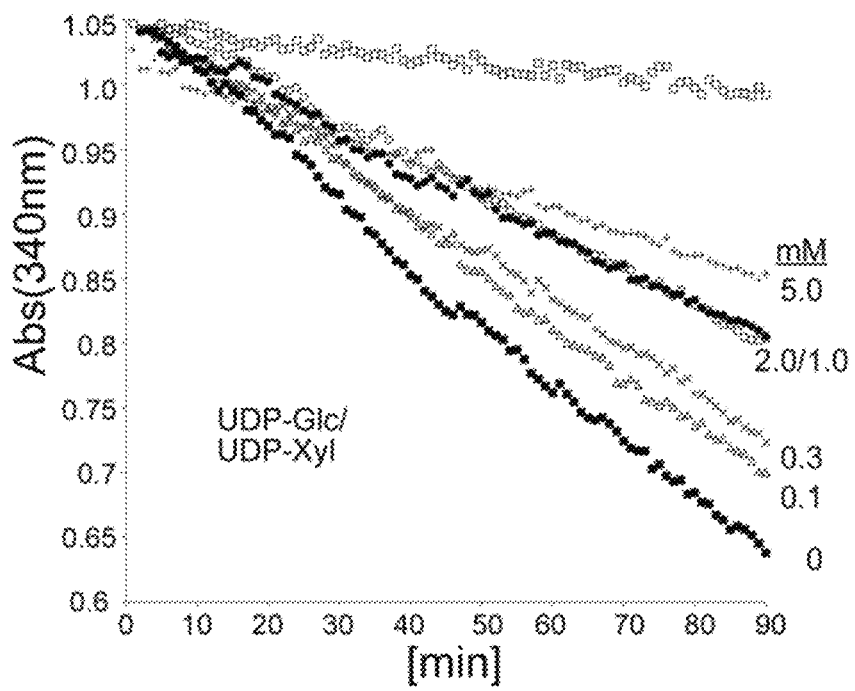

Cellulose syntheses in the presence of 1 mM UDP-Glc and increasing concentrations of UDP-Gal, -NAG, or -Xyl reveal a concentration-dependent inhibition of polymer synthesis, with UDP-Xyl as strongest inhibitor. At 5 mM concentration, UDP-NAG reduces the apparent reaction rate by only 20%, whereas UDP-Xyl reduces the activity by about 60%, suggesting a UDP- as well as a sugar-specific effect on inhibition (FIGS. 4B and C, FIG. 5B). Interestingly, the reactions proceed for at least 90 min at a constant rate, indicating that the alternative sugars are either not at all incorporated, or limited incorporation does not have a cumulative adverse effect on the overall reaction rate (FIG. 5C).

Figure 5D:
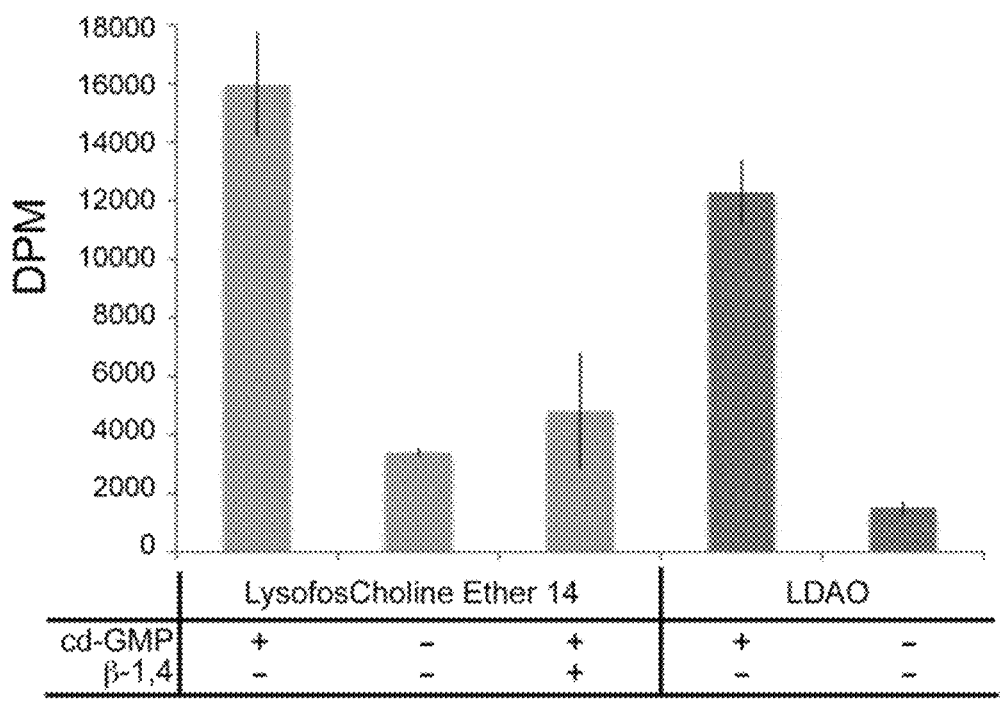

Several capsular exopolysaccharides are assembled from lipid-bound intermediates (46). Based on radiotracer labeling, a similar mechanism has been proposed for cellulose synthesis in Agrobacterium tumefaciens, by which cellulose would be assembled from short, lipid-linked oligosaccharides (47). To investigate whether BcsA-B's activity requires any components provided by the E. coli total lipid extract used for reconstitution, we performed cellulose synthesis reactions in a detergent-solubilized state, in the absence of any additional phospholipids. BcsA-B purified in the detergent lauryl N,N-dimethylamine oxide (LDAO) or LFCE14 robustly synthesizes cellulose in a c-di-GMP dependent manner, which is degraded by cellulase, consistent with the synthesis of an authentic β-1,4 glucan (FIG. 5D). We note that, in a detergent-solubilized state, the enzyme displays approximately 10 to 20% residual activity in the absence of c-di-GMP, perhaps due to an increased conformational flexibility of the "gating loop" controlling access to BcsA's active site (2). Although the presence of lipids arising from the E. coli expression system cannot be fully ruled out, these results strongly suggest that the involvement of lipid-linked oligosaccharides in the elongation reaction is unlikely. This is further supported by the large distance between the active site and the putative lipid-water interface (~25 Å) (2).

The Membrane-Associated Domain of BcsB is Essential for Cellulose Synthesis

Based on the architecture of the BcsA-B complex, the strict dependence of BcsA's catalytic activity on BcsB is surprising. While BcsB shares a large interface with BcsA, none of its domains are in close proximity to the active site (2). Likewise, BcsB only interacts with the translocating glucan on the periplasmic side of the membrane, thus it is unlikely that it participates in the translocation reaction. BcsB is a multi-domain protein containing a repeat of a CBD linked to a flavodoxin-like domain (FD) (2). The N-terminal CBD-1, which forms the membrane distal part, is located at the tip of the dome-shaped molecule, followed by FD-1. This organization is repeated with CBD-2 and FD-2 before BcsB forms a short amphipathic helix followed by its C-terminal TM anchor. The TM anchor packs into a deep groove formed by BcsA's TM helices 1, 2, and 3.

To identify the core region of BcsB required for catalytic activity of BcsA, we systematically truncated BcsB N-terminally starting either at Gly190 (after CBD-1), at Thr309

Figure 6A:
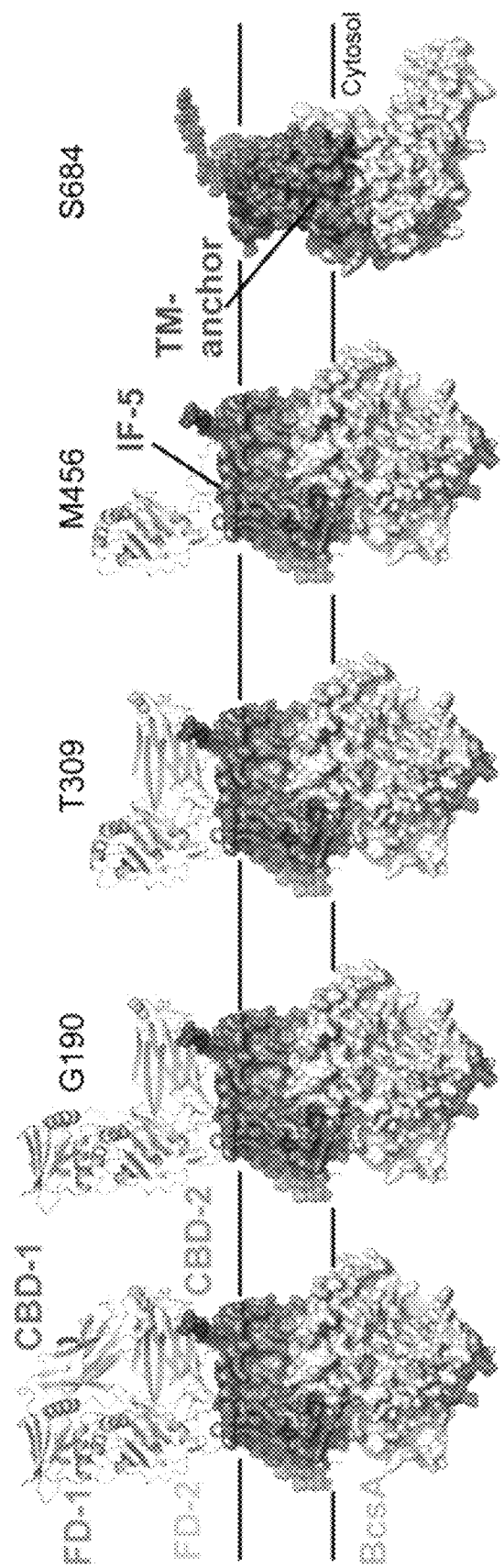
FIG. 6A-6C (also referred to as Example 1, FIG. 6): The membrane-associated domain of BesB is required for cellulose synthesis.
Figure 6B:
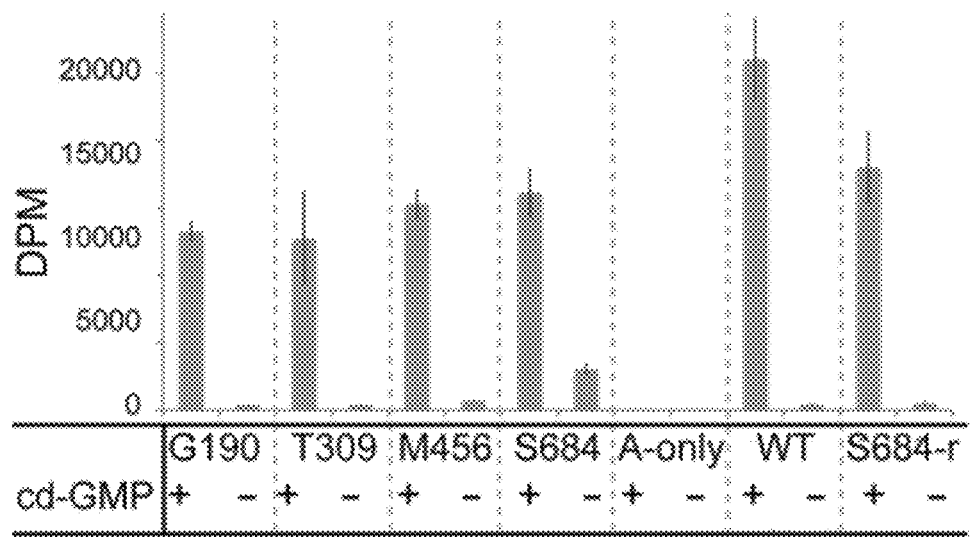

(after FD-1), at Met456 (after CBD-2) or at Ser684 (after FD-2) (FIG. 6A). The constructs were co-expressed with BcsA and the cellulose synthase activity of the truncated complexes was analyzed in IMVs. While IMVs containing only BcsA fail to produce any HMW polymer, essentially all BcsB truncations supported a comparable catalytic activity of BcsA, demonstrating that only the C-terminal membrane-associated region of BcsB is required for function (FIG. 6B).

To further confirm that the catalytic activity of the BcsA-B-S684 complex is indeed due to the interaction of BcsA with the BcsB fragment, we purified the truncated complex by Ni-affinity and gel filtration chromatography via the C-terminal poly-histidine tag on BcsA. As shown in FIGS. 6B and C, the FLAG-tagged BcsB-S684 fragment co-purifies with BcsA and the purified complex is catalytically active after reconstitution into PLs, demonstrating that residues 684 to 720 of BcsB suffice to mediate the interaction with and maintain the catalytic activity of the cellulose synthase.

Example 1—Discussion

The purified Rs BcsA-B complex allows, for the first time, characterizing cellulose synthesis in a purified state. In vitro, BcsA-B synthesizes HMW cellulose in the presence of UDP-Glc and the allosteric activator c-di-GMP, thus providing a model system for not only cellulose synthesis but also for c-di-GMP induced exopolysaccharide secretion, implicated in biofilm formation.

Upon activation by c-di-GMP, BcsA-B processively elongates the cellulose polymer, achieving a degree of polymerization in vitro in the range 200-300. This reaction proceeds at a similar rate in detergent-solubilized and membrane-reconstituted states, highly favoring a model by which BcsA catalyzes the stepwise transfer of UDP-activated glucose to the growing acceptor without the involvement of any lipid-linked reaction intermediates. Because glucan elongation is tightly coupled to its translocation through BcsA's TM pore (2) and robust cellulose synthesis occurs in vitro in the absence of electrochemical gradients, the GT reaction must suffice to energize cellulose translocation.

In accordance with other biofilm polysaccharides (11), BcsA-B most likely produces amorphous cellulose, consisting of randomly oriented glucan chains. No cellulose microfibrils were observed by electron microscopy analyses and the sensitivity of the synthesized cellulose towards cellulase digestion further indicates the loose organization of the individual glucan chains.

Cyclic-di-GMP activates cellulose synthesis allosterically and binds BcsA-B with high affinity. It is a potent inducer of biofilm formation, thus the mechanism by which it activates exopolysaccharide synthases is of particular importance. In contrast to other biofilm polysaccharide synthases, such as alginate- and poly-β-1,6 N-acetyl glucosamine (Pga) synthase, the c-di-GMP-binding PilZ domain of cellulose synthase is a part of the catalytic BcsA subunit (Example 1, FIG. S6). In alginate synthase, Alg44, resembling BcsB in its TM topology, contains an intracellular c-di-GMP-binding PilZ domain and associates with the catalytic Alg8 subunit (17). Pga synthases do not contain PilZ domains, but bind c-di-GMP at the interface between the catalytic PgaC and the associated PgaD subunits (Example 1, FIG. S6) (48).

Titration of UDP-Glc at increasing c-di-GMP concentrations shows that c-di-GMP does not alter BcsA's apparent affinity for UDP-Glc, yet it increases BcsA's apparent catalytic rate in vitro at least 10-fold. These observations are consistent with a model by which c-di-GMP binding exposes BcsA's active site, perhaps by removing a "lid" covering the opening of the GT domain (2), thereby directly allowing substrate binding to and product release from the active site. In the absence of c-di-GMP or under conditions where the concentration of c-di-GMP is rate limiting, only a fraction of the catalytic sites might be accessible, thus reducing the overall reaction rate.

In order to transport cellulose across the bacterial cell envelop the inner-membrane BcsA-B complex most likely interacts with BcsC in the outer membrane (Example 1, FIG. S6). A mechanism has to be in place that prevents BcsA from synthesizing cellulose into the periplasm before this interaction is established. While the periplasmic cellulase BcsZ may hydrolyze mislocalized polymers, the demonstrated dependence of BcsA's catalytic activity on the presence of BcsB provides an alternative control mechanism. In vivo, BcsB could associate with BcsC before interacting with and activating BcsA.

'With the exception of this study, no cellulose synthase activity has been recovered from purified components, neither from pro-nor eukaryotic sources (24, 25). While BcsA requires BcsB for catalytic activity, only its C-terminal TM anchor together with a preceding amphipathic helix is necessary for activity. Its interaction with BcsA likely stabilizes the TM region of BcsA, such that the synthase is catalytically active. A destabilized TM region of BcsA would not only affect the glucan channel, but would also alter the localization of the signature pentapeptide (Gln-X-X-Arg-Trp) (49) that stabilizes the acceptor glucan at the active site (2). Thus, it is conceivable that eukaryotic cellulose synthases also require additional components for activity, which might dissociate during purification, leading to preparations with drastically reduced cellulose synthase rates. The described biochemical analysis of bacterial cellulose synthesis offers an alternative route to identify potential CesA interaction partners similar to BcsB.

Example 1 Materials and Methods

The Rs BcsA and BcsB cellulose synthase subunits were expressed in E. coli C43 and purified as described (2). The purified complex was reconstituted into proteoliposomes after incubation with detergent-solubilized E. coli total lipid extract and detergent removal by stepwise addition of SM-2 BioBeads. Cellulose synthesis was initiated by addition of UDP-Glc and c-di-GMP in the presence of $MgCl_2$ and incubation at 37° C. The synthesized cellulose was quantified after incorporation of 3H-labeled glucose as radiotracer by scintillation counting. Enzyme-coupled cellulose synthesis assays were performed spectrophotometrically by coupling cellulose synthesis to the reactions of PK and lactate dehydrogenase. Full experimental details are provided in SI Materials and Methods.

Example 1—Supplemental Materials and Methods

Constructs

The bcsA and bcsB genes were cloned into the pETDuet expression vector as described (1). BcsA was expressed with a C-terminal dodeca-histidine tag to facilitate purification and the mature region of BcsB was fused to an N-terminal PelB signal sequence for correct targeting. All N-terminal truncation mutants of BcsB were cloned as C-terminally FLAG-tagged species into the pETDuet expression vector containing the wild-type bcsA gene using NcoI and HindIII restriction sites. The expression of the truncated complexes was as described for the wild type complex (1).

Protein Expression and Purification

All BcsA-B complexes were expressed in E. coli C43 (2) in auto-induction medium and were purified by metal affinity and size-exclusion chromatography as described (1). The protein was solubilized from the membrane fraction in Triton X-100 detergent, followed by detergent exchange into 1 mM LFCE14 or 5 mM LDAO during metal affinity chromatography. The purified complexes were concentrated to 50 µM final concentration using an extinction coefficient of (161,925 M-1 cm-1) and reconstituted into PLs or ND.

Preparation of Inverted Membrane Vesicles

The cell pellet obtained from a 2-L culture of E. coli C43 over-expressing the BcsA-B complex was resuspended in RB-buffer containing 20 mM sodium phosphate, pH 7.2, 100 mM NaCl and 10% glycerol and lysed in a bench-top microfluidizer. The whole cell extract was cleared from cell debris by centrifugation for 20 min at 12,500 rpm in a Beckman JA-20 rotor at 4° C. and the supernatant was floated on a 1.8 M sucrose cushion by centrifugation at 100,000×g for 120 min at 4° C. in a Beckman 45Ti rotor. The membrane vesicles were recovered from the top of the sucrose cushion, diluted 5-fold in RB-buffer and sedimented overnight at 100,000×g in a 45Ti rotor. The purified IMVs were resuspended in 1 ml RB-buffer, homogenized in a tissue grinder and stored in aliquots at −80° C.

Reconstitution into Proteoliposomes and Nanodiscs

The purified and concentrated BcsA-B complex was incubated at 5 µM final concentration with 5 mg/ml E. coli total lipid extract solubilized in 8 mM LFCE14 in AB-buffer containing 25 mM sodium phosphate pH 7.5, 0.3 M NaCl, 5 mM cellobiose and 10% glycerol. The detergent was removed by addition of SM-2 BioBeads (BioRad) until the turbidity of the solution indicated the formation of lipid vesicles. The obtained PLs were stored in aliquots at −80° C.

For reconstitution into ND, the apoA1 mutant MSP was expressed and purified as described (3) and incubated at 120 µM with 30 µM of purified BcsA-B and 1 mg/ml E. coli total lipid extract solubilized in 8 mM LFCE14. The detergent was removed by addition of BioBeads and the reconstituted NDs were purified over a S200 analytical gel filtration column in 20 mM Tris pH 7.5, 100 mM NaCl, 5 mM cellobiose and 10% glycerol. The purified NDs were concentrated to 5 µM assuming an additive extinction coefficient of 185,875 M-1 cm-1 for BcsA-B and MSP (4).

Sedimentation Assays

Standard cellulose synthase sedimentation assays were performed by incubating 1 µM of cellulose synthase complexes, either in PLs, ND or detergent micelles, in the presence of 30 µM c-di-GMP, 20 mM MgCl2, 5 mM UDP-Glc and 0.25 µCi UDP-[3H]-Glc in AB-buffer lacking glycerol and containing only 0.1 M NaCl. Following incubation at 37° C. for 45 min, the polymerization reaction was terminated by addition of 2% SDS and the water-insoluble polymer was pelleted by centrifugation at 15,000 rpm at room temperature (RT). The obtained pellet was resuspended in 20 µL 50 mM Tris pH 7.5, 0.1 M NaCl and spotted at the origin of a descending Whatman-2MM chromatography paper, which was developed in an aqueous solution of 60% ethanol. For enzymatic degradation, the pellet was resuspended in 20 µL 50 mM sodium acetate pH 4.5 and 100 mM NaCl and was digested with 0.1 mg/ml of endo-β-1,4- or endo-β-1,3 glucanase from Aspergillus niger (TCI) or Trichoderma sp. (Megazyme), respectively. Following paper chromatography, the high molecular weight polymer retained at the origin was quantified by scintillation counting.

To ensure a constant ratio of UDP-Glc to 3H-labeled UDP-Glc for the titration of UDP-Glc in the presence of 0.7 mM UDP (FIG. 4C), a 4-fold concentrated stock solution containing 20 mM UDP-Glc and 1.0 µCi UDP-[3H]-Glc was diluted to the final substrate concentration required for the individual experiments. Following synthesis, the reactions were treated as described above.

Enzyme Coupled Activity Assays

Pyruvate kinase (PK)—and lactate dehydrogenase (LDH)-coupled activity assays were performed by incubating 0.5 µM cellulose synthase with 1 U PK and 1 U LDH, 0.5 mM NADH, 1 mM phosphoenolpyruvate, and 30 mM MgCl2 in 20 mM Tris pH 7.5, 100 mM NaCl, 5 mM cellobiose and 10% glycerol in a total volume of 20 µL. The cellulose synthase complex was added last to the reaction mix after a pre-incubation for 10 min at RT. The decrease in absorbance at 340 nm was measured in a SpectraMax plate reader in Corning 384 well clear flat bottom assay plates. Control reactions in the absence of cellulose synthase were performed to determine the background NADH oxidation. Data were plotted and analyzed in Origin (5) and fitted to monophasic Michaelis-Menten kinetics as described (3).

Western-Blot Analysis

Proteins were separated by SDS-PAGE on a 12.5% polyacrylamide gel and transferred to nitrocellulose membranes at 100 V and constant current (350 mA) for 60 min at 4° C. in a BioRad Mini-Transfer Cell according to the manufacturer's specifications. The nitrocellulose membrane was blocked in 5% milk/TBS-Tween solution for 30 min and incubated overnight with an anti-penta-His (Qiagen) or anti-FLAG (Sigma) primary mouse antibody. The membranes were washed three times in 5% milk/TBS-Tween before incubating with an IRDye800-conjugated anti-mouse secondary antibody (Rockland) for 45 min at RT. After washing, the membranes were scanned on an Odyssey Infrared Imager (Licor).

Linkage Analysis

The freeze-dried in vitro product obtained from 20 µL of 1 µM PL-reconstituted BcsA-B was dispersed in 200 µL dry dimethylsulfoxide (DMSO). The mixture was incubated for 6 h at RT combining sonication (10 min intervals every hour) and agitation with a magnetic stirrer. Samples were maintained under argon atmosphere during the dispersion and methylation steps. Methylation reactions were performed using the NaOH/CH3I method (6) by repeating 5 times the methylation step on each sample, thereby avoiding any risk of undermethylation. Partially methylated polysaccharides were hydrolyzed in the presence of 2 M TFA at 121° C. for 2 h and further derivatized to permethylated alditolacetates (7). The latter were separated and analyzed by gas chromatography/electron-impact mass spectrometry (GC/EI-MS) on a SP-2380 capillary column (30 m×0.25 mm i.d.; Supelco) using a HP-6890 GC system and a HP-5973 electron-impact mass spectrometer as a detector (Agilent Technologies). The temperature program increased from 160° C. to 210° C. at a rate of 1° C. min-1 The mass spectra of the fragments obtained from the permethylated alditolacetates were compared with those of reference derivatives.

Data Analysis

All measurements were performed at least in triplicate and error bars represent deviations from the means.

The description of Example 1 has published since the provisional application was filed as Omadjela et al., 2013, Proc. Natl. Acad. Sci., 110:44:17856.

Example 1 Bibliography

1. Hubbard C, McNamara J T, Azumaya C, Patel M S, Zimmer J (2012) The hyaluronan synthase catalyzes the synthesis and membrane translocation of hyaluronan. J Mol Biol 418:21-31.
2. Morgan J L, Strumillo J, Zimmer J (2013) Crystallographic snapshot of cellulose synthesis and membrane translocation. Nature 493:181-186.
3. Nishiyama Y, Sugiyama J, Chanzy H, Langan P (2003) Crystal structure and hydrogen bonding system in cellulose I(alpha) from synchrotron X-ray and neutron fiber diffraction. J Am Chem Soc 125:14300-14306.
4. Romling U (2002) Molecular biology of cellulose production in bacteria. Res Microbiol 153:205-212.
5. Somerville C (2006) Cellulose synthesis in higher plants. Annu Rev Cell Dev Biol 22:53-78.
6. Grimson M J, Haigler C H, Blanton R L (1996) Cellulose microfibrils, cell motility, and plasma membrane protein organization change in parallel during culmination in Dictyostelium discoideum. J Cell Sci 109:3079-3087.
7. Cantarel B L, Coutinho P M, Rancurel C, Bernard T (2009) The Carbohydrate-Active EnZymes database (CAZy): an expert resource for Glycogenomics. Nucleic Acids Res 37:D233-8.
8. Sethaphong L, Haigler C H, Kubicki J D, Zimmer J, Bonetta D, DeBolt S, Yingling Y G (2013) Tertiary model of a plant cellulose synthase. Proc Natl Acad Sci USA 110:7512-7517.
9. Kimura S, Laosinchai W, Itoh T, Cui X, Linder C R, Brown R M J (1999) Immunogold labeling of rosette terminal cellulose-synthesizing complexes in the vascular plant vigna angularis. Plant Cell 11:2075-2086.
10. Jahn C E, Selimi D A, Barak J D, Charkowski A O (2011) The Dickeya dadantii biofilm matrix consists of cellulose nanofibres, and is an emergent property dependent upon the type III secretion system and the cellulose synthesis operon. Microbiol 157:2733-2744.
11. McCrate O A, Zhou X, Reichhardt C, Cegelski L (2013) Sum of the Parts: Composition and Architecture of the Bacterial Extracellular Matrix. J Mol Biol
12. Cotter P A, Stibitz S (2007) c-di-GMP-mediated regulation of virulence and biofilm formation. Curr Op Microbiol 10:17-23.
13. Ryjenkov D A, Simm R, Romling U, Gomelsky M (2006) The PilZ domain is a receptor for the second messenger c-di-GMP: the PilZ domain protein YcgR controls motility in enterobacteria. J Biol Chem 281:30310-30314.
14. Amikam D, Galperin M Y (2006) PilZ domain is part of the bacterial c-di-GMP binding protein. Bioinformatics 22:3-6.
15. Römling U, Galperin M Y, Gomelsky M (2013) Cyclic di-GMP: the First 25 Years of a Universal Bacterial Second Messenger. Microbiol Mol Biol Rev 77:1-52.
16. Keiski C L, Harwich M, Jain S, Neculai A M, Yip P, Robinson H, Whitney J C, Riley L, Burrows L L, Ohman D E et al. (2010) AlgK is a TPR-containing protein and the periplasmic component of a novel exopolysaccharide secretin. Structure 18:265-273.
17. Rehm B H A (2009) Alginate Production: Precursor Biosynthesis, Polymerization and Secretion. Microbiology Monographs 13:55-71.
18. Saxena I M, Kudlicka K, Okuda K, Brown R M (1994) Characterization of genes in the cellulose-synthesizing operon (acs operon) of Acetobacter xylinum: implications for cellulose crystallization. J Bacteriol 176:5735-5752.
19. Standal R, Iversen T G, Coucheron D H, Fjaervik E, Blatny J M, Valla S (1994) A new gene required for cellulose production and a gene encoding cellulolytic activity in Acetobacter xylinum are colocalized with the bcs operon. J Bacteriol 176:665-672.
20. Mazur O, Zimmer J (2011) Apo- and Cellopentaose-bound Structures of the Bacterial Cellulose Synthase Subunit BcsZ. J Biol Chem 286:17601-17606.
21. Mann E E, Wozniak D J (2012) Pseudomonas biofilm matrix composition and niche biology. FEMS Microbiol Rev 36:893-916.
22. Iguchi M, Yamanaka S, Budhiono A (2000) Bacterial cellulose; a masterpiece of nature's arts. J Mater Sci 35:261-270.
23. Guerriero G, Fugelstad J, Bulone V (2010) What do we really know about cellulose biosynthesis in higher plants? J Integr Plant Biol 52:161-175.
24. Aloni Y, Delmer D P, Benziman M (1982) Achievement of high rates of in vitro synthesis of 1,4-beta-D-glucan: activation by cooperative interaction of the Acetobacter xylinum enzyme system with GTP, polyethylene glycol, and a protein factor. Proc Natl Acad Sci USA 79:6448-6452.
25. Cifuentes C, Bulone V, Emons A M C (2010) Biosynthesis of callose and cellulose by detergent extracts of tobacco cell membranes and quantification of the polymers synthesized in vitro. J Int Plant Biol 52:221-233.
26. Lai-Kee-Him J, Chanzy H, Müller M, Putaux J-L, Imai T, Bulone V (2002) In vitro versus in vivo cellulose microfibrils from plant primary wall synthases: structural differences. J Biol Chem 277:36931-36939.
27. Pappas C T, Sram J, Moskvin O V, Ivanov P S, Mackenzie R C, Choudhary M, Land M L, Larimer W, Kaplan S, Gomelsky M (2004) Construction and validation of the Rhodobacter sphaeroides 2.4.1 DNA microarray: transcriptome flexibility at diverse growth modes. J Bacteriol 186:4748-4758.
28. Wagner S, Klepsch M M, Schlegel S, Appel A, Draheim R, Tarry M, Hogbom M, van Wijk K J, Slotboom D J, Persson J O et al. (2008) Tuning Escherichia coli for membrane protein overexpression. Proc Natl Acad Sci USA 105:14371-14376.
29. Charnock S J, Henrissat B, Davies G J (2001) Three-dimensional structures of UDP-sugar glycosyltransferases illuminate the biosynthesis of plant polysaccharides. Plant Physiol 125:527-531.
30. Ninomiya T, Sugiura N, Tawada A, Sugimoto K, Watanabe H, Kimata K (2002) Molecular cloning and characterization of chondroitin polymerase from Escherichia coli strain K4. J Biol Chem 277:21567-21575.

31. DeAngelis P L, Jing W, Graves M V, Burbank D E, Van Etten J L (1997) Hyaluronan synthase of chlorella virus PBCV-1. Science 278:1800-1803.
32. Lairson L L, Henrissat B, Davies G J, Withers S G (2008) Glycosyltransferases: structures, functions, and mechanisms. Annu Rev Biochem 77:521-555.
33. Wallace J A, Shen J K (2009) Predicting pKa values with continuous constant pH molecular dynamics. Methods Enzymol 466:455-475.
34. Koyama M, Helbert W, Imai T, Sugiyama J, Henrissat B (1997) Parallel-up structure evidences the molecular directionality during biosynthesis of bacterial cellulose. Proc Natl Acad Sci USA 94:9091-9095.
35. Brown C, Leijon F, Bulone V (2012) Radiometric and spectrophotometric in vitro assays of glycosyltransferases involved in plant cell wall carbohydrate biosynthesis. Nat Protoc 7:1634-1650.
36. Boehme C, Bieber F, Linnemann J, Breitling R, Lorkowski S, Reissmann S (2013) Chemical and enzymatic characterization of recombinant rabbit muscle pyruvate kinase. Biol Chem 394:695-701.
37. Denisov I G, Grinkova Y V, Lazarides A A, Sligar S G (2004) Directed self-assembly of monodisperse phospholipid bilayer nanodiscs with controlled size. J Am Chem Soc 126:3477-3487.
38. Park S H, Berkamp S, Cook G A, Chan M K, Viadiu H, Opella S J (2011) Nanodiscs versus macrodiscs for NMR of membrane proteins. Biochemistry 50:8983-8985.
39. Buckstein M H, He J, Rubin H (2008) Characterization of nucleotide pools as a function of physiological state in *Escherichia coli*. J Bacteriol 190:718-726.
40. Simm R, Morr M, Kader A, Nimtz M, Römling U (2004) GGDEF and EAL domains inversely regulate cyclic di-GMP levels and transition from sessility to motility. Mol Microbiol 53:1123-1134.
41. Benziman M, Haigler C H, Bown R M, White A R, Cooper K M (1980) Cellulose biogenesis: Polymerization and crystallization are coupled processes in *Acetobacter xylinum*. Proc Natl Acad Sci USA 11:6678-6682.
42. Paredez A R, Somerville C R, Ehrhardt D W (2006) Visualization of cellulose synthase demonstrates functional association with microtubules. Science 312:1491-1495.
43. Ross P, Weinhouse H, Aloni Y, Michaeli D, Weinberger-Ohana P, Mayer R, Braun S, de Vroom E, van der Marel G A, van Boom J H et al. (1987) Regulation of cellulose synthesis in *Acetobacter xylinum* by cyclic diguanylic acid. Nature 325:279-281.
44. Harris D M, Corbin K, Wang T, Gutierrez R, Bertolo A L, Petti C, Smilgies D-M, Estevez J M, Bonetta D, Urbanowicz B R et al. (2012) Cellulose microfibril crystallinity is reduced by mutating C-terminal transmembrane region residues CESA1A903V and CESA3T942I of cellulose synthase. Proc Natl Acad Sci USA 109:4098-4103.
45. Chen S, Ehrhardt D W, Somerville C R (2010) Mutations of cellulose synthase (CESA1) phosphorylation sites modulate anisotropic cell expansion and bidirectional mobility of cellulose synthase. Proc Natl Acad Sci USA 107:17188-17193.
46. Whitfield C (2006) Biosynthesis and assembly of capsular polysaccharides in *Escherichia coli*. Annu Rev Biochem 75:39-68.
47. Matthysse A G, Thomas D L, White A R (1995) Mechanism of cellulose synthesis in *Agrobacterium tumefaciens*. J Bacteriol 177:1076-1081.
48. Steiner S, Lori C, Boehm A, Jenal U (2013) Allosteric activation of exopolysaccharide synthesis through cyclic di-GMP-stimulated protein-protein interaction. EMBO J 32:354-368.
49. Pear J R, Kawagoe Y, Schreckengost W E, Delmer D P, Stalker D M (1996) Higher plants contain homologs of the bacterial celA genes encoding the catalytic subunit of cellulose synthase. Proc Natl Acad Sci USA 93:12637-12642.

Example 1 Supplementary Bibliography

1. Morgan J L, Strumillo J, Zimmer J (2013) Crystallographic snapshot of cellulose synthesis and membrane translocation. Nature 493:181-186.
2. Wagner S, Klepsch M M, Schlegel S, Appel A, Draheim R, Tarry M, Hogbom M, van Wijk K J, Slotboom D J, Persson J O et al. (2008) Tuning *Escherichia coli* for membrane protein overexpression. Proc Natl Acad Sci USA 105:14371-14376.
3. Hubbard C, McNamara J T, Azumaya C, Patel M S, Zimmer J (2012) The hyaluronan synthase catalyzes the synthesis and membrane translocation of hyaluronan. J Mol Biol 418:21-31.
4. Denisov I G, Grinkova Y V, Lazarides A A, Sligar S G (2004) Directed self-assembly of monodisperse phospholipid bilayer Nanodiscs with controlled size. J Am Chem Soc 126:3477-3487.
5. Origin OriginLab, Northampton, Mass.
6. Ciucanu I, Kerek F (1984) A simple and rapid method for the permethylation of carbohydrates. Carbohydr Res 131: 209-217.
7. Albersheim P, Nevins P D, English P D, Karr A (1967) A method for the analysis of sugars in plant cell wall polysaccharides by gas liquid chromatography. Carbohydr Res 5:340-345.

Example 2: Mechanism of Activation of Bacterial Cellulose Synthase by Cyclic-di-GMP Introduction Biofilms are sessile multi-cellular bacterial communities that are encased in a 3-dimensional meshwork of biopolymers, such as polysaccharides, proteinaceous filaments, and nucleic acids[1-3]. The biofilm matrix provides protection against mechanical stress[4,5] and controls the diffusion of signaling molecules, nutrients and toxic compounds. In fact, biofilm communities exhibit increased tolerance towards conventional anti-microbial treatments and sterilization techniques and are responsible for many chronic infections associated with cystic fibrosis and endocarditis[6,7] as well as nosocomial infections[8]. In many cases, biofilm formation occurs in response to an elevated cytosolic concentration of cyclic-di-GMP (c-di-GMP)[9], a bacterial signaling molecule recognized by a wide range of effector proteins, including transcription factors, flagellar components, riboswitches and exopolysaccharide synthases[1]. Therefore, targeting c-di-GMP-binding effectors has emerged as an attractive new route for the development of urgently needed novel anti-microbial therapeutics.

C-di-GMP activates the synthesis of bacterial cellulose[1,10], an extracellular polysaccharide often found in biofilms[11]. C-di-GMP monomers and dimers[12,13] are both recognized by effector proteins via PilZ domains, first identified as regulatory components of cell motility[14], which comprise an "RxxxR" motif in a flexible linker region followed by a β-sheet or β-barrel that contains a "DxSxxG" motif[15]. Both sequence motifs have been shown to interact with c-di-GMP in structures of isolated PilZ domains[16,17]. However, the mechanism by which c-di-GMP binding at PilZ domains modulates enzymatic functions is completely unknown to date. Extracellular polysaccharides of the biofilm matrix, such as cellulose, alginate and poly-N-acetylglucosamine (PNAG), are likely synthesized and secreted by a conserved mechanism[18-22]. Bacterial cellulose synthase polymerizes glucose molecules via β-1,4 glycosidic linkages in a multi-step process which requires the presence of a divalent cation, mostly magnesium[23]. First, upon stimulation by c-di-GMP, the enzyme binds its substrate UDP-Glc (donor) at an intracellular glycosyltransferase (GT) domain. Second, the donor glucose is transferred to the 4' hydroxyl group at the non-reducing end of the growing polysaccharide chain (acceptor), thereby extending the polymer and forming UDP as a second reaction product[23,24]. Third, following glycosyl transfer, the elongated polymer has to be translocated by one glucose unit into a transmembrane (TM) channel so that the newly added glucose unit occupies the acceptor site and UDP must be replaced with UDP-Glc for another round of catalysis.

The membrane-integrated bacterial cellulose synthase contains the inner membrane components BcsA and BcsB as well as the outer membrane protein BcsC[25,26]. BcsA, together with the periplasmic membrane-anchored BcsB subunit, forms a complex that is sufficient for cellulose synthesis and translocation[23,27]. BcsA is homologous to eukaryotic cellulose synthases[28] and contains eight TM helices and a cytosolic GT domain between TM helices four and five[27]. The enzyme is a processive family-2 GT[29] that elongates the non-reducing end of the growing polysaccharide chain. This reaction requires a general base, which is likely provided by the Asp residue of a "TED" motif found at the beginning of a short helix within the GT domain and in close proximity to the acceptor's 4' hydroxyl[27]. BcsA also forms a polysaccharide channel across the membrane, directly above the active site, thereby allowing the coupling of cellulose synthesis and translocation[27,30].

Bacterial cellulose and alginate synthases are activated by c-di-GMP via PilZ domains[15,31]. BcsA forms a PilZ domain within its C-terminal intracellular extension, which consists of a six-stranded β-barrel and a preceding linker region[15,27]. The β-barrel rests against the intracellular GT domain and is connected to BcsA's C-terminal TM helix (TM8) via a linker (TM8-β-barrel linker) harboring the "RxxxR" motif involved in c-di-GMP binding[15].

The TM8-β-barrel linker also interacts with BcsA's "gating loop", which runs across the opening of the GT domain towards the cytosol, thereby blocking access to the catalytic pocket in the non-stimulated or "resting" state of the enzyme[27]. It was speculated that substrate binding to the active site requires the repositioning of the gating loop, perhaps induced by c-di-GMP[27]. This model is supported by biochemical studies indicating that increasing c-di-GMP concentrations do not alter $K_M$, but instead increase the fraction of catalytically active enzymes[23].

In order to unravel the mechanism by which c-di-GMP activates bacterial cellulose synthase, we determined c-di-GMP-bound structures of the *Rhodobacter sphaeroides* BcsA-B complex at intermediate states during cellulose synthesis and translocation. The c-di-GMP-bound structures reveal the architecture of the activated BcsA-B complex and provide unique insights into the mechanism of c-di-GMP signaling. These include the identification of a conserved regulatory salt bridge that auto-inhibits BcsA in the absence of c-di-GMP and the UDP-dependent repositioning of a gating loop to either open the catalytic pocket or to coordinate the nucleotide at the active site. Furthermore, the structures reveal the movement of a "finger helix" of BcsA, which interacts with the acceptor end of the translocating cellulose polymer, towards the TM channel entrance, correlating with the translocation of the cellulose polymer into the channel by one glucose unit. Thus, our data provide the first insights into the mechanism by which c-di-GMP modulates enzymatic functions and represent novel snapshots of cellulose synthesis and membrane translocation.

Protein Purification

BcsA-B was purified as previously described[27] with the exception that gel filtration was carried out in 20 mM Tris pH 7.5, 100 mM NaCl, 5 mM $MgCl_2$, 5 mM cellobiose, 10% glycerol, 5 mM N,N-Dimethyl-N-dodecylamine N-oxide (LDAO), and 0.3 mM LysoFosCholine Ether 12 (LFCE12), (GF buffer). Peak fractions containing BcsA and BcsB were collected and concentrated to ~10 mg/ml and spun at 180,000 g for 15 min at 4° C. Bicelles were prepared by mixing 250 μl water with 100 mg of 1,2-dimyristoyl-sn-glycero-3-phosphocholine:1-palmitoyl-2-oleoyl-sn-glycero-3-phosphoethanolamine:3-[(3-cholamidopropyl)dimethylammonio]-1-propanesulfonate, (DMPC:POPE:CHAPS) at a molar ratio of ~2.34:0.05:1. The concentrated protein was mixed with the bicelles at a 4:1 (v:v) ratio and allowed to equilibrate on ice for at least 1 hour. 2 mM UDP and 1 mM c-di-GMP were added before incubating on ice overnight.

Crystallization

Crystals belonging to space group $P2_12_12_1$ were grown by sitting-drop vapor diffusion at 30° C. in 1.65-1.9 M sodium acetate and 100 mM sodium citrate, pH 3-3.5, (final pH≈5.6) at a 1:1 (v:v) ratio of protein/bicelle and well solution. Crystals appeared within 3 days and reached their final size within 14 days. For the UDP-free structure, cryo-protection and dilution of UDP were achieved by gradual addition of a solution containing 20 mM sodium citrate pH 3, 100 mM NaCl, 5 mM $MgCl_2$, 1.95 M sodium acetate, 20% glycerol, and 20% bicelles to the drop. For the UDP-bound structure, cryo-protection and soaking with UDP were achieved by gradual addition of a solution containing 20 mM sodium citrate pH 3.5, 50 mM $MgCl_2$, 1.95 M sodium acetate, 20% glycerol, 12% bicelles, and 10 mM UDP to the drop. Crystals were flash-cooled in liquid nitrogen for data collection.

Data Collection and Processing

Diffraction data were collected at 100K at a wavelength of 1.0 Å. Data in the absence of UDP were collected at the Advanced Photon Source SER-CAT beamline 22-ID and data in the presence of UDP were collected at GM/CA-CAT beamline 23-ID. The data were integrated using Mosflm[51] and scaled in Aimless as part of the CCP4 program suite[52].

Structure Determination

Initial phases for the UDP-free structure were determined by molecular replacement (MR) in Phaser[53] using ligand-free pdb 4HG6 with BcsA residues 499-512 (gating loop) and 574-758 (C terminus) truncated as a search model.

MR-phases for the UDP-bound structure were determined in MOLREP[54] using the UDP-free structure without the gating loop as search model.

The models were refined by rigid body and restrained refinement in Refmac5[52] as well as simulated annealing in Phenix[55]. Phases were improved using density modification in Parrot[56,57], and model building was performed in Coot[58]. Iterative rounds of model building, refinement, and density modification resulted in a map of sufficient quality to place the missing domains and ligands. In order to minimize model bias, simulated annealing composite omit maps, prime and switch maps, and kicked maps[55,59] were calculated and evaluated throughout the model building process. Additionally, TLS parameters determined from the TLSMD server[60] were utilized in later rounds of refinement. The model contains residues 13-740 of BcsA and residue 54-720 of BcsB. Residue 532-543 of BcsB are disordered as previously observed[27] and were omitted from the model. A 10 residue long unidentified peptide likely belonging to either the extended N terminus of BcsB or the C terminus of BcsA is sandwiched by BcsB's flavodoxin-like domain 2 and carbohydrate-binding domain 2[27] between crystallographic symmetry mates. This peptide was modeled as a polyalanine with chain identifier "D". The UDP-free model contains 5 partially ordered lipids, one modeled as 1,2-diacyl-sn-glycero-3-phosphoethanolamine and 4 modeled as 1,2-diacyl-sn-glycero-3-phosphocholine. Two of these lipids were also observed in the UDP-bound structure.

The UDP-free BcsA-B structure was refined to an $R/R_{free}$ of 19.9/23.0. 95.8% of residues lie in the favored regions of the Ramachandran plot with no outliers. The UDP-bound complex structure was refine to an $R/R_{free}$ of 20.6/23.8. 95.1% of residues lie in the favored region on a Ramachandran plot with 0.7% outliers. Figures were prepared in Pymol[61] and the solvent accessible surface analysis was performed in HOLLOW[62]. Crystallographic software support is provided by SBGrid[63].

Inverted Membrane Vesicle Preparation

Inverted membrane vesicles (IMVs) containing wild type BcsB and the indicated BcsA mutants were prepared as previously described[30]. Control IMVs were prepared from *E. coli* transformed with an empty pETDuet vector. In brief, the constructs were expressed as described[27] and the cells were resuspended in RB buffer containing 20 mM sodium phosphate pH 7.3, 100 mM NaCl, and 10% glycerol using 20 ml RB per cell pellet from a 1 L culture. The cells were lysed in a microfluidizer and spun at 12,000 g for 20 min to clear the cell debris. The supernatant was applied on the surface of a 1.8 M sucrose cushion and spun at 150,000 g for 2 hr at 4° C. IMVs were harvested, diluted 3-fold in RB, and spun at 150,000 g overnight. The pellet from a 3 L culture was resuspended in 1 ml RB, homogenized in a dounce, and stored in aliquots at −80° C.

Proteoliposome Preparation

Purified BcsA-B complex containing the indicated mutations were reconstituted into proteoliposomes (PLs) as previously described[23]. Briefly, BcsA-B was purified as described above with the exception that 1 mM LysoFos-Choline Ether 14 (LFCE14) was used instead of LDAO. The protein was concentrated to 5 µM, incubated with 4 mg/ml *E. coli* total lipid extract (diluted from a 20 mg/ml stock solution in 40 mM LDAO) and allowed to equilibrate on ice for at least 20 min. Bio-Beads (BioRad) were added, and the solution was rotated until it became turbid, indicating the formation of PLs. The samples were then aliquoted, snap-frozen in liquid nitrogen, and stored at −80° C. The final protein concentration for all mutants was determined by UV absorbance and SDS-PAGE followed by Coomassie staining.

In Vitro Cellulose Synthesis Assay

IMVs or PLs were added to a solution containing 20 mM sodium phosphate, 100 mM NaCl, 20 mM $MgCl_2$, 5 mM UDP-glucose, 12.5 µCi/ml UDP-[$^3$H]-glucose as well as 30 µM c-di-GMP unless indicated otherwise. The reaction was incubated at 37° C. for 45 min with shaking at 350 rpm. 2% SDS was added to terminate the reaction and dissolve the vesicles. The mixture was then spun at 21,000 g for at least 20 min to pellet the insoluble cellulose. The supernatant was carefully removed, and the pellet was resuspended in 50 mM Tris pH 7.5 and 100 mM NaCl and spotted on Whatman 3 mm grid paper. The product was purified in 60% ethanol by descending paper chromatography, with the insoluble cellulose remaining at the origin, and quantified by scintillation counting[30]. All measurements were performed at least in triplicate and error bars represent standard deviations.

Western Analysis

10 µL IMVs were analyzed by SDS-PAGE and transferred to a nitrocellulose membrane using a BioRad Mini-Transfer Cell according to the manufacturer's specifications. The nitrocellulose membrane was blocked in 5% milk/TBS-Tween solution for 30 min and incubated overnight with a mouse anti-penta-His (Qiagen) antibody. The membranes were washed three times in 5% milk/TBS-Tween before incubating with an IRDye800-conjugated anti-mouse secondary antibody (Rockland) for 45 min at RT. After washing, the membranes were scanned on an Odyssey Infrared Imager (Licor).

Enzyme-Coupled Activity Assay

Enzyme-coupled kinetic assays were carried out as previously described[23] with the exception that the protein was reconstituted into PLs instead of nanodiscs, the experiments were performed in 150 µl reaction volume in 96-well flat bottom Microplates (Greiner), and 3 mM UDP-Glc was used.

Isothermal Titration Calorimetry

The protein was purified in 1 mM LFCE14 as described above. Measurements were carried out at 25° C. in a MicroCal iTC200 system (GE Healthcare) with 250 µl of BcsA-B in the cell at 9.3 µM for WT and 11 µM for the BcsA-Arg580Ala complex and 400 µM c-di-GMP in the syringe. An initial 0.5 µl injection was followed by 39 1 µl injections spaced 180 s apart with stirring at 700 rpm. The data were fit using Origin 7.0 as provided by the manufacturer.

Results

Architecture of BcsA-B in Complex with c-di-GMP

We purified *Rhodobacter sphaeroides* BcsA-B from *E. coli*, crystallized it in complex with c-di-GMP by the bicelle crystallization method,[32,33] and solved the structure by molecular replacement at a resolution of 2.65 Å. Additionally, we obtained a c-di-GMP- and UDP-bound structure of BcsA-B by soaking crystals with UDP and refining at 3.2 Å resolution (Example 2, Table 1). Both structures contain a translocating cellulose polymer 17 glucose units in length that co-purifies with the BcsA-B complex.

Overall, the c-di-GMP-bound BcsA-B structure is consistent with the previously reported structure obtained from detergent-solubilized complexes (RMSD≈1 Å for all atoms)[27] (Example, FIG. 1). Two register shifts by one residue were identified in regions that were poorly ordered in the previously reported structure of BcsA (residues 171-190) and BcsB (residues 268-280). The corrected register in BcsA positions Asp179 of the "DDG" motif in hydrogen bonding distance with the conserved Tyr216 and Asp180 in hydrogen bonding distance with the uracil moiety of UDP and Arg219 (Example 2, Supplementary FIG. 1).

BcsA Binds a c-di-GMP Dimer on the β-Barrel Surface

BcsA's C-terminal PilZ domain binds an intercalated c-di-GMP dimer[12] (Example 2, FIG. 1 and Supplementary FIG. 2). The guanine groups of the c-di-GMP dimer stack parallel to the β-barrel surface and perpendicular to the TM8-β-barrel linker. One c-di-GMP molecule (c-di-GMP-A) interacts with the "DxSxxG" motif on the β-barrel surface, while the second (c-di-GMP-B) is stabilized by π-π stacking interactions with c-di-GMP-A as well as by residues within the TM8-β-barrel linker (Example 2, FIG. 1c).

All of the conserved PilZ domain residues mediate interactions with the c-di-GMP dimer (Example 2, Supplementary FIG. 2b) as also observed with isolated PilZ domains[16, 17]. Of note is the interaction of the "RxxxR" motif within the TM8-β-barrel linker with c-di-GMP (Example 2, FIG. 1c). The N-terminal Arg of this motif (Arg580) runs co-planar to the second guanylate of c-di-GMP-A and forms hydrogen bonds via its guanidinium group with the guanine's N7 and carbonyl oxygen. The C-terminal Arg (Arg584) of the "RxxxR" motif also interacts with c-di-GMP-A by stacking on top of the first and forming a salt bridge with the phosphate group of the second guanylate moiety, (Example 2, FIG. 1c and Supplementary FIG. 2b). In the absence of c-di-GMP, Arg580 is rotated by almost 180° towards BcsA's GT domain and forms a salt bridge with Glu371[27]. This interaction is broken upon c-di-GMP binding, leading to increased flexibility of BcsA's gating loop as described below.

The non-conserved Arg579, directly preceding the "RxxxR" motif, runs co-planar to the guanine group of c-di-GMP-B and stacks on top of c-di-GMP-A (Supplementary FIG. 2b). A basic residue in this position is likely necessary to stabilize the interaction with a c-di-GMP dimer, as demonstrated by mutagenesis studies on isolated PilZ domains[16,34].

Most structures of β-barrel-containing PilZ domains contain a short α-helix that follows the last strand of the β-barrel and lays flat across its opening[16,17]. In BcsA, this helix (termed hinge helix) is sandwiched at the interface between the β-barrel and the GT domain (Example 2, FIG. 1b). When the β-barrel interacts with c-di-GMP, it rotates by approximately 20° around the hinge helix towards the GT domain (Example 2, FIG. 1b). This rotation closes a groove between the β-barrel and the GT domain that accommodates a short stretch of BcsA's non-conserved extreme C terminus in the c-di-GMP-free state[27], leading to the disorder of BcsA's C-terminal residues past Arg740.

Conformational Changes of the Gating Loop

C-di-GMP-binding allows BcsA's conserved gating loop (residues 499 to 517) to adopt a new conformation, away from the active site cleft and near the water-lipid interface, (Example 2, FIG. 2a and Supplementary FIG. 3). In this "open" state, the gating loop is stabilized by hydrophobic interactions with BcsA's amphipathic interface helices (IF), which run parallel to the plane of the membrane at the cytosolic water-lipid boundary (Example 2, FIGS. 1 and 2a) and form the entrance to BcsA's TM channel[27]. Phe503 and Val1505 of the gating loop's "FxVTxK" motif (Supplementary FIG. 3a) pack into a conserved hydrophobic pocket formed by Ile377 from IF2, Tyr486, Leu487 and Ala490 of IF3 and Ile520 at the beginning of TM helix 7 (Example 2, FIG. 2a).

The transition of the gating loop from the previously observed resting to the open state is supported by c-di-GMP-induced conformational changes of the PilZ domain. In the absence of c-di-GMP, the gating loop rests in front of the GT domain entrance, thereby blocking the active site (Example 2, FIG. 2 and Supplementary FIG. 3). This "resting" state is stabilized by Arg580 of the "RxxxR" motif, which contacts the backbone carbonyl of Thr511 near the C-terminal end of the gating loop (Example 2, FIG. 3). Arg580 is positioned in close proximity to Thr511 because it also forms a salt bridge with Glu371 of the GT domain, right next to the gating loop's Thr511 (Example 2, FIG. 3). The gating loop further interacts with the PilZ domain via its C-terminal end, which forms a two-stranded β-sheet with the c-di-GMP-binding TM8-β-barrel linker (Example 2, FIGS. 1 and 2). Accordingly, in the presence of c-di-GMP, the TM8-β-barrel linker together with the interacting gating loop rotates by about 2 Å towards the water-lipid interface (Example 2, FIG. 1b) and, importantly, Arg580 rotates by 180° away from the GT domain to coordinate c-di-GMP, thereby breaking its interaction with the gating loop and Glu371 (Example 2, FIG. 3). This transition releases the gating loop, allowing it to pivot around Arg499 and Glu514 and to swing from its resting state towards the membrane interface. The movement of the gating loop, particularly of residues 504-510, creates a large window at the GT domain entrance approximately 22.5 by 12.5 Å wide, which is sufficient to allow UDP-Glc to enter and UDP to exit the active site (Example 2, FIG. 2b).

In order to mimic a substrate-bound state of BcsA, we soaked crystals with UDP, a product and competitive inhibitor of BcsA[23]. In the presence of UDP the gating loop is found in another conformation, inserted deep into the substrate-binding pocket (Example 2, FIG. 4a and Supplementary FIGS. 3c and d). The loop swings by approximately 15 Å towards the active site, thereby closing the large window formed in its open conformation (Example 2, FIG. 4a and Supplementary FIG. 3e). In this inserted state, each residue of the loop's "FxVTxK" motif is involved in coordinating UDP at the active site. Phe503 and Val505 rest on opposing sides above the uracil moiety while Thr506 and Lys508 coordinate its pyrophosphate (FIG. 5b). The pyrophosphate is further stabilized by Gln379 and Arg382 of the "QxxRW" motif, as well as a $Mg^{2+}$ ion coordinated in turn by Asp246 and Asp248 of the "DxD" motif and His249. Thus, the insertion of the gating loop is likely important for positioning the donor for catalysis. Indeed, in the absence of c-di-GMP, its insertion into the active site is prevented due to steric clashes of its backbone with the Arg580-Glu371 salt bridge (Supplementary FIG. 4b), further ensuring a catalytically inactive state.

C-di-GMP Releases an Auto-Inhibited State of BcsA

Activation by c-di-GMP is a characteristic of prokaryotic cellulose synthases[10,35]. Arg580 within the TM8-β-barrel linker either interacts with c-di-GMP or, in the absence of the allosteric activator, is stabilized towards the GT domain by forming a salt bridge with Glu371, thereby tethering the gating loop in the resting position (Example 2, FIG. 3). Although belonging to the evolutionarily conserved GT domain, Glu371 is only conserved among prokaryotic, c-di-GMP-responsive cellulose synthases, suggesting a regulatory function for the Arg580-Glu371 interaction (Example 2, Supplementary FIG. 4a).

Indeed, disrupting this salt bridge by replacing Glu371 with Ala increases the enzyme's catalytic activity in the absence of c-di-GMP approximately 6-fold compared to the wild type enzyme, (Example 2, FIGS. 5a and b). Under these conditions, Arg580 may still be able to interact with the gating loop's backbone. However, replacing Arg580 with Ala, either in the wild type or E371A background, renders BcsA constitutively active as observed by quantifying the formation of each reaction product, cellulose (Example 2, FIGS. 5a and b and Supplementary FIG. 5a) or UDP (Example 2, FIG. 5c) Importantly, the R580A mutant still binds c-di-GMP, although with slightly reduced affinity (Example 2, Supplementary FIG. 5b); yet, even at a c-di-GMP concentration more than 50-fold above its dissociation constant, no further stimulation of cellulose biosynthesis is observed (Example 2, FIG. 5d). These observations suggest that the Arg580-Glu371 salt bridge and the subsequent interaction of Arg580 with the gating loop are responsible for auto-inhibiting the synthase. This inhibition is then released when Arg580 rotates away from the GT domain to interact with c-di-GMP.

The TM Channel Entrance Forms the Acceptor-Binding Site

Following sugar transfer, processive GTs, including cellulose, chitin, alginate and hyaluronan synthases, must translocate the elongated polysaccharide, such that the newly formed product sits in a position where it can serve as the acceptor in a subsequent glycosyl transfer reaction. BcsA contacts the acceptor end of the translocating cellulose polymer via a "finger helix" that belongs to the conserved GT domain (Example 2, FIG. 1). The finger helix contains the "TED" motif at its N terminus, of which Asp343 most likely forms the general base for catalysis[27]. In contrast to our previously reported structure in which the finger helix points away from the TM channel entrance ("down" state)[27], this helix is bent towards the entrance to the channel in both of our new structures and the cellulose polymer is moved into the channel by one glucose unit (Example 2, FIG. 6a). The finger helix bends near its last C-terminal helical turn and around the conserved His351 (Example 2, Supplementary FIG. 6a), which is stabilized via side chain interactions with the conserved Ser357 and Tyr410, thereby forming a pivot (Example 2, Supplementary FIG. 6b). Asp343 at the tip of the finger helix moves by approximately 5 Å towards the TM channel entrance, which is in agreement with the length of a glucopyranose unit (Example 2, FIGS. 6a and b).

A network of conserved hydrophilic and hydrophobic interactions stabilizes the "up" position of the finger helix near the TM channel entrance, including residues from the gating loop, IF2 and the TM channel. Phe316 and Phe317 of the "FFCGS" motif (Example 2, Supplementary FIG. 7) at the TM channel entrance straddle the helix and additional van-der-Waals interactions are mediated via Gly386 and Met390 of IF2 and Tyr410 within the N-terminal amphipathic section of TM helix 5 (Example 2, FIG. 6c and Supplementary FIG. 6b). In addition, Thr339, preceding the "TED" motif of the finger helix, hydrogen bonds with the conserved Gln389 of IF2, which in turn interacts with Pro498 at the N-terminal end of the gating loop (Example 2, FIG. 6c).

The transition of the finger helix towards the channel entrance is supported by a small peripheral loop (residues 333 to 338) that precedes the finger helix. The loop carries a conserved Gly residue (Gly334) at its midpoint, which is followed by a bulky hydrophobic residue, mostly Phe or Ile (Example 2, FIGS. 6a and c and Supplementary FIG. 6a). In the c-di-GMP-bound state, the loop moves towards the GT domain and Phe335 plugs into a conserved hydrophobic pocket beneath the active site, where it is surrounded by the side chains of Met230, Leu234, Val244, Phe317, Leu324 and Leu329 (Example 2, FIG. 6c and Supplementary FIG. 6c).

Figure 6C:
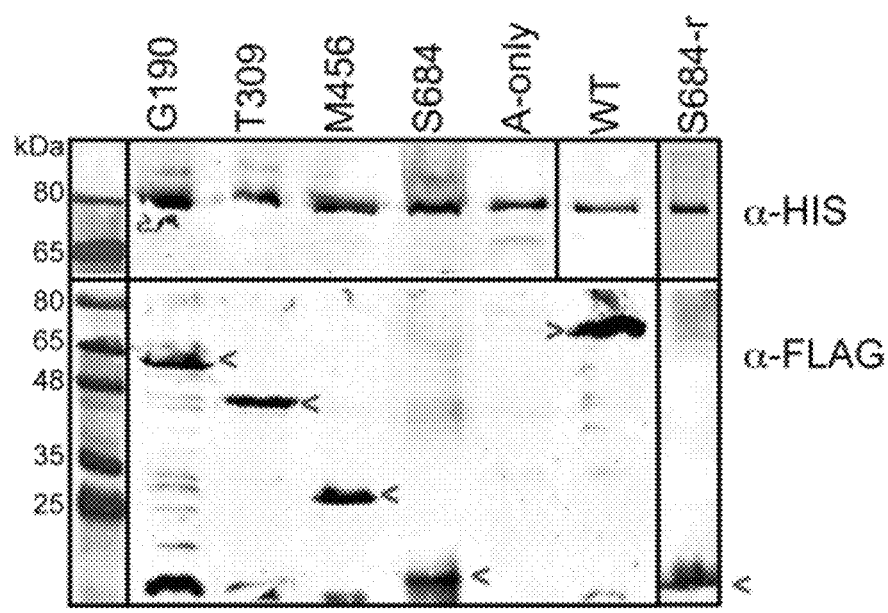

The position of the translocating glucan's terminal glucose unit in the c-di-GMP-bound BcsA-B complex suggests that the acceptor coordination site is located just inside the entrance to the TM channel (Example 2, FIGS. 6a and d). One face of the acceptors glucopyranose ring forms CH-π stacking interactions[36] with Trp383 of the "QxxRW" motif, which is characteristic of processive GTs, while its opposite side contacts the carbonyl oxygen of Cys318 of the "FFCGS" motif (Example 2, FIG. 6c and Supplementary FIG. 7). The N-terminal part of the finger helix contacts the acceptor via the "TED" motif, of which Thr341 and Asp343 form hydrogen bonds with the acceptor's 2' or 6' (depending on its orientation) and 4' hydroxyl groups (FIGS. 6c and d). In particular, the side chain carboxylate of Asp343 is within 2.6 Å of the acceptor's 4' hydroxyl group, consistent with its putative role as the catalytic base during glycosyl transfer[27]. The acceptor further interacts with Tyr302, also located at the entrance to the TM channel (Example 2, FIG. 6d). Accordingly, this implies that cellulose synthase forms the acceptor coordination site with the invariant "QxxRW" and "FFCGS" motifs at the entrance to the TM channel (Example 2, Supplementary FIG. 7). The stabilization of the terminal glucose unit at this position resembles the coordination of a single galactose molecule in the sodium-coupled sugar transporter vSGLT[37], (Example 2, FIG. 6e), suggesting that BcsA's acceptor binding site might also suffice to coordinate a single glucose molecule to initiate cellulose synthesis.

Example 2 Discussion

Comparing the structures of the c-di-GMP-activated and resting states of the BcsA-B complex, at intermediate states during cellulose translocation provides unique insights into the mechanism of cellulose biosynthesis. In the absence of c-di-GMP, BcsA is catalytically inactive and its gating loop blocks the entrance to the active site[23,27]. Allosteric activation by c-di-GMP displaces the gating loop from the active site, thereby forming a large opening towards the substrate-binding pocket, wide enough for substrate diffusion. However, opening and closing the active site is unlikely to be the only function of BcsA's gating loop. When UDP binds to the active site, the gating loop inserts deeply into the catalytic pocket and coordinates the nucleotide via conserved residues. Most likely, this also reflects how BcsA interacts with its substrate UDP-Glc, positioning it for catalysis, excluding water from the active site and perhaps also stabilizing the UDP leaving group during glycosyl transfer. A similar mechanism of substrate-dependent loop insertion and de-insertion has been described for non-processive galactosyltransferases[38,39].

The functional importance of the gating loop is further underlined by its sequence homology with the location of the isoxaben resistance mutation in *Arabidopsis thaliana* cellulose synthase 3 (Example 2, Supplementary FIG. 3*a*). Here, Thr942 of the "FxVTxK" motif is mutated to Ile, thereby allowing growth in the presence of the herbicide isoxaben[40]. However, because pro- and eukaryotic cellulose synthases differ in their predicted TM topologies[28], further experimental analyses are required to confirm a similar eukaryotic gating loop function.

UDP, the second reaction product of many GTs[24,41], competitively inhibits BcsA, which has also been observed for hyaluronan synthases[23,42]. BcsA binds UDP and UDP-Glc with similar affinities[23], however, the large excess of UDP-Glc over UDP under physiological conditions would favor substrate binding upon gating loop opening[43]. Presumably during or after UDP-Glc binding, the gating loop inserts into the active site to initiate catalysis. Following glycosyl transfer and with the newly extended glucan at the active site, the gating loop may retract from the GT domain, thereby allowing UDP to UDP-Glc exchange. Because the gating loop undergoes its full range of motion in the presence of c-di-GMP, it is likely that the allosteric activator remains bound during catalysis. In vivo, c-di-GMP-stimulated cellulose biosynthesis may terminate upon depletion of the activator, whose cytosolic concentration is in turn controlled by the synergy of diguanylate cyclases and diesterases[1].

The BcsA-B complex contains a translocating cellulose polymer that spans the distance from the GT domain to the periplasmic BcsA-B interface. In the c-di-GMP activated structure, the polymer's acceptor terminus rests at the entrance to the TM channel, one glucose unit further into the pore compared to its position in the absence of c-di-GMP[27]. Thus, while our previously reported structure likely represents a state post glycosyl transfer but prior to translocation, the c-di-GMP-activated BcsA-B structure is consistent with a state after polymer translocation. Cellulose translocation may be accomplished by BcsA's finger helix, which hydrogen bonds with the acceptor glucose and pivots towards the TM channel entrance in the c-di-GMP-activated complex. In this position, Asp343 of the finger helix is at an ideal distance to facilitate catalysis. Perhaps the finger helix returns to the "down" position after glycosyl transfer to interact with the new polymer terminus A similar mechanism involving a flexible loop or helical domain has been postulated for the processive translocation of unfolded polypeptide chains[44,45].

C-di-GMP stimulates the biosynthesis of several extracellular polysaccharides important for biofilm formation, including alginate and PNAG[46-48]. While the mechanism for activating PNAG biosynthesis most likely differs from BcsA[48], alginate and cellulose synthases share a strikingly similar organization[49]. Alginate is a major component of *Pseudomonas aeruginosa* biofilms in the respiratory tract of cystic fibrosis patients[18,49]. In contrast to BcsA-B, the alginate synthase's c-di-GMP-binding PilZ domain is located at the intracellular N terminus of Alg44, the non-catalytic subunit that resembles BcsB and likely interacts with the catalytic Alg8 subunit. Thus, c-di-GMP could exert control by a similar mechanism in alginate synthase as revealed for bacterial cellulose synthase.

Our analyses provide the first insights into how enzymatic functions can be modulated by c-di-GMP. A detailed mechanistic characterization of this bacterial signaling system is required for the development of novel anti-microbial therapeutics.

Accession Codes

Atomic coordinates and structure factors for the DP-free and UDP-bound complexes have been deposited at the Protein Data Bank under accession number 4P02 and 4P00, respectively.

The results of Example 2 have published since the provisional application was filed as Morgan et al., 2014, Nature Structural & Molecular Biology, 21:5:489.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

TABLE 1

Example 2,
Crystallographic data collection and refinement statistics.

|  | UDP-free | UDP-bound |
|---|---|---|
| Data collection | | |
| Space group | $P2_12_12_1$ | $P2_12_12_1$ |
| Cell dimensions | | |
| a, b, c (Å) | 67.6, 214.7, 220.4 | 67.5, 216.8, 219.6 |
| α, β, γ (°) | 90, 90, 90 | 90, 90, 90 |
| Resolution (Å) | 34.75-2.65 (2.70-2.65) * | 49.62-3.20 (3.30-3.20) |
| $R_{pim}$ | 0.056 (0.577) | 0.079 (0.499) |
| $CC_{1/2}$ | 0.995 (0.553) | 0.992 (0.566) |
| Mean I/σI | 7.8 (1.3) | 8.7 (2.1) |
| Completeness (%) | 92.3 (94.3) | 98.7 (99.5) |
| Redundancy | 4.5 (4.1) | 4.7 (4.7) |
| Refinement | | |
| Resolution (Å) | 20-2.65 | 49-3.2 |
| No. reflections | | |
| Total | 85,948 | 53,241 |
| $R_{free}$ | 4,307 | 2,714 |
| $R_{work}/R_{free}$ | 19.9/23.0 | 20.6/23.8 |
| No. atoms | | |
| Protein | 10,673 | 10,709 |
| β-1,4 glucan | 187 | 187 |
| c-di-GMP | 92 | 92 |
| UDP | — | 25 |
| $Mg^{2+}$ | 1 | 1 |
| Lipids | 89 | 58 |
| B-factors | | |
| Chain A | 74.5 | 74.6 |
| Chain B | 66.3 | 68.3 |
| Chain D | 77.2 | 91.3 |

TABLE 1-continued

Example 2,
Crystallographic data collection and refinement statistics.

|  | UDP-free | UDP-bound |
|---|---|---|
| β-1,4 glucan | 78.1 | 81.2 |
| c-di-GMP-A | 59.2 | 61.5 |
| c-di-GMP-B | 64.1 | 58.8 |
| UDP | — | 80.8 |
| Lipids | 85.6 | 113.6 |
| R.m.s deviations | | |
| Bond lengths (Å) | 0.003 | 0.002 |
| Bond angles (°) | 0.754 | 0.760 |

\* Values in parentheses refer to the highest-resolution shell.
^Correlation between intensities from random half-data sets[50].

Example 2 Bibliography

1. Römling, U., Galperin, M. Y. & Gomelsky, M. Cyclic di-GMP: the First 25 Years of a Universal Bacterial Second Messenger. *Microbiol. Mol. Biol. Rev.* 77, 1-52 (2013).
2. Gloag, E. S., Turnbull, L., Huang, A., Vallotton, P., Wang, H., Nolan, L. M., Mililli, L., Hunt, C., Lu, J., Osvath, S. R., Monahan, L. G., Cavaliere, R., Charles, I. G., Wand, M. P., Gee, M. L., Prabhakar, R. & Whitchurch, C. B. Self-organization of bacterial biofilms is facilitated by extracellular DNA. *Proc. Natl. Acad. Sci. USA* 110, 11541-11546 (2013).
3. McCrate, O. A., Zhou, X., Reichhardt, C. & Cegelski, L. Sum of the parts: composition and architecture of the bacterial extracellular matrix. *J. Mol. Biol.* 425, 4286-4294 (2013).
4. Wilking, J. N., Zaburdaev, V., De Volder, M., Losick, R., Brenner, M. P. & Weitz, D. A. Liquid transport facilitated by channels in *Bacillus subtilis* biofilms. *Proc. Natl. Acad. Sci. USA* 110, 848-852 (2013).
5. Stewart, P. S. & Costerton, J. W. Antibiotic resistance of bacteria in biofilms. *Lancet* 358, 135-138 (2001).
6. Romling, U. & Balsalobre, C. Biofilm infections, their resilience to therapy and innovative treatment strategies. *J. Intern. Med.* 272, 541-561 (2012).
7. Pritt, B., O'Brien, L. & Winn, W. Mucoid *Pseudomonas* in cystic fibrosis. *Am. J. Clin. Pathol.* 128, 32-34 (2007).
8. Gomes, F., Teixeira, P. & Oliveira, R. Mini-review: Staphylococcus epidermidis as the most frequent cause of nosocomial infections: old and new fighting strategies. *Biofouling* 30, 131-141 (2014).
9. Cotter, P. A. & Stibitz, S. c-di-GMP-mediated regulation of virulence and biofilm formation. *Curr. Op. Microbiol.* 10, 17-23 (2007).
10. Ross, P., Weinhouse, H., Aloni, Y., Michaeli, D., Weinberger-Ohana, P., Mayer, R., Braun, S., de Vroom, E., van der Marel, G. A., van Boom, J. H. & Benziman, M. Regulation of cellulose synthesis in *Acetobacter xylinum* by cyclic diguanylic acid. *Nature* 325, 279-281 (1987).
11. Zogaj, X., Bokranz, W., Nimtz, M. & Römling, U. Production of cellulose and curli fimbriae by members of the family Enterobacteriaceae isolated from the human gastrointestinal tract. *Infect. Immun.* 71, 4151-4158 (2003).
12. Zhang, Z., Kim, S., Gaffney, B. L. & Jones, R. A. Polymorphism of the signaling molecule c-di-GMP. *J. Am. Chem. Soc.* 128, 7015-7024 (2006).
13. Gentner, M., Allan, M. G., Zaehringer, F., Schirmer, T. & Grzesiek, S. Oligomer formation of the bacterial second messenger c-di-GMP: reaction rates and equilibrium constants indicate a monomeric state at physiological concentrations. *J. Am. Chem. Soc.* 134, 1019-1029 (2012).
14. Christen, M., Christen, B., Allan, M. G., Folcher, M., Jeno, P., Grzesiek, S. & Jenal, U. DgrA is a member of a new family of cyclic diguanosine monophosphate receptors and controls flagellar motor function in *Caulobacter crescentus*. *Proc. Natl. Acad. Sci. USA* 104, 4112-4117 (2007).
15. Amikam, D. & Galperin, M. Y. PilZ domain is part of the bacterial c-di-GMP binding protein. *Bioinformatics* 22, 3-6 (2006).
16. Ko, J., Ryu, K. S., Kim, H., Shin, J. S., Lee, J. O., Cheong, C. & Choi, B. S. Structure of PP4397 reveals the molecular basis for different c-di-GMP binding modes by Pilz domain proteins. *J. Mol. Biol.* 398, 97-110 (2010).
17. Benach, J., Swaminathan, S. S., Tamayo, R., Handelman, S. K., Folta-Stogniew, E., Ramos, J. E., Forouhar, F., Neely, H., Seetharaman, J., Camilli, A. & Hunt, J. F. The structural basis of cyclic diguanylate signal transduction by PilZ domains. *EMBO J.* 26, 5153-5166 (2007).
18. Hay, I. D., Ur Rehman, Z., Moradali, M. F., Wang, Y. & Rehm, B. H. Microbial alginate production, modification and its applications. *Microb. Biotechnol.* 6, 637-650 (2013).
19. Hay, I. D., Wang, Y., Moradali, M. F., Rehman, Z. U. & Rehm, B. H. Genetics and regulation of bacterial alginate production. *Environ Microbiol* (2014).
20. Whitney, J. C. & Howell, P. L. Synthase-dependent exopolysaccharide secretion in Gram-negative bacteria. *Trends Microbiol.* 21, 63-72 (2013).
21. Wang, X., Preston, J. F. r. & Romeo, T. The pgaABCD locus of *Escherichia coli* promotes the synthesis of a polysaccharide adhesin required for biofilm formation. *J. Bacteriol.* 186, 2724-2734 (2004).
22. Merzendorfer, H. Insect chitin synthases: a review. *J Comp Physiol B, Biochem Syst Environ Physiol* 176, 1-15 (2006).
23. Omadjela, O., Narahari, A., Strumillo, J., Melida, H., Mazur, O., Bulone, V. & Zimmer, J. BcsA and BcsB form the catalytically active core of bacterial cellulose synthase sufficient for in vitro cellulose synthesis. *Proc. Natl. Acad. Sci. USA* 110, 17856-17861 (2013).
24. Brown, C., Leijon, F. & Bulone, V. Radiometric and spectrophotometric in vitro assays of glycosyltransferases involved in plant cell wall carbohydrate biosynthesis. *Nat Protoc* 7, 1634-1650 (2012).
25. Mayer, R., Ross, P., Weinhouse, H., Amikam, D., Volman, G., Ohana, P., Calhoon, R. D., Wong, H. C., Emerick, A. W. & Benziman, M. Polypeptide composition of bacterial cyclic diguanylic acid-dependent cellulose synthase and the occurrence of immunologically crossreacting proteins in higher plants. *Proc. Natl. Acad. Sci. USA* 88, 5472-5476 (1991).
26. Saxena, I. M., Kudlicka, K., Okuda, K. & Brown, R. M. Characterization of genes in the cellulose-synthesizing operon (acs operon) of *Acetobacter xylinum*: implications for cellulose crystallization. *J. Bacteriol.* 176, 5735-5752 (1994).
27. Morgan, J. L., Strumillo, J. & Zimmer, J. Crystallographic snapshot of cellulose synthesis and membrane translocation. *Nature* 493, 181-186 (2013).
28. Slabaugh, E., Davis, J. K., Haigler, C. H., Yingling, Y. G. & Zimmer, J. Cellulose synthases: new insights from crystallography and modeling. *Trends Plant. Sci.* (2013).

29. Cantarel, B. L., Coutinho, P. M., Rancurel, C. & Bernard, T. The Carbohydrate-Active EnZymes database (CAZy): an expert resource for Glycogenomics. *Nucleic Acids Res.* 37, D233-8 (2009).
30. Hubbard, C., McNamara, J. T., Azumaya, C., Patel, M. S. & Zimmer, J. The hyaluronan synthase catalyzes the synthesis and membrane translocation of hyaluronan. *J. Mol. Biol.* 418, 21-31 (2012).
31. Merighi, M., Lee, V. T., Hyodo, M., Hayakawa, Y. & Lory, S. The second messenger bis-(3'-5')-cyclic-GMP and its PilZ domain-containing receptor Alg44 are required for alginate biosynthesis in *Pseudomonas aeruginosa. Mol. Microbiol.* 65, 876-895 (2007).
32. Faham, S. & Bowie, J. U. Bicelle crystallization: a new method for crystallizing membrane proteins yields a monomeric bacteriorhodopsin structure. *J. Mol. Biol.* 316, 1-6 (2002).
33. Faham, S., Boulting, G. L., Massey, E. A., Yohannan, S., Yang, D. & Bowie, J. U. Crystallization of bacteriorhodopsin from bicelle formulations at room temperature. *Protein Science* 14, 836-840 (2005).
34. Fujiwara, T., Komoda, K., Sakurai, N., Tajima, K., Tanaka, I. & Yao, M. The c-di-GMP recognition mechanism of the PilZ domain of bacterial cellulose synthase subunit A. *Biochem. Biophys. Res. Commun.* 431, 802-807 (2013).
35. Aloni, Y., Delmer, D. P. & Benziman, M. Achievement of high rates of in vitro synthesis of 1,4-beta-D-glucan: activation by cooperative interaction of the *Acetobacter xylinum* enzyme system with GTP, polyethylene glycol, and a protein factor. *Proc. Natl. Acad. Sci. USA* 79, 6448-6452 (1982).
36. Kumari, M., Sunoj, R. B. & Balaji, P. V. Exploration of CH . . . π mediated stacking interactions in saccharide: aromatic residue complexes through conformational sampling. *Carbohydr. Res.* 361, 133-140 (2012).
37. Faham, S., Watanabe, A., Besserer, G. M., Cascio, D., Specht, A., Hirayama, B. A., Wright, E. M. & Abramson, J. The crystal structure of a sodium galactose transporter reveals mechanistic insights into Na+/sugar symport. *Science* 321, 810-814 (2008).
38. Qasba, P. K., Ramakrishnan, B. & Boeggeman, E. Structure and Function of β-1,4-Galactosyltransferase. *Curr. Drug Targets* 4, 292-309 (2008).
39. Ramakrishnan, B., Ramasamy, V. & Qasba, P. K. Structural snapshots of beta-1,4-galactosyltransferase-I along the kinetic pathway. *J. Mol. Biol.* 357, 1619-1633 (2006).
40. Scheible, W. R., Eshed, R., Richmond, T., Delmer, D. & Somerville, C. Modifications of cellulose synthase confer resistance to isoxaben and thiazolidinone herbicides in *Arabidopsis* Ixr1 mutants. *Proc. Natl. Acad. Sci. USA* 98, 10079-10084 (2001).
41. Lairson, L. L., Henrissat, B., Davies, G. J. & Withers, S. G. Glycosyltransferases: structures, functions, and mechanisms. *Annu. Rev. Biochem.* 77, 521-555 (2008).
42. Tlapak-Simmons, V. L., Baron, C. A. & Weigel, P. H. Characterization of the purified hyaluronan synthase from *Streptococcus equisimilis. Biochemistry* 43, 9234-9242 (2004).
43. Buckstein, M. H., He, J. & Rubin, H. Characterization of nucleotide pools as a function of physiological state in *Escherichia coli. J. Bacteriol.* 190, 718-726 (2008).
44. Erlandson, K. J., Miller, S. B., Nam, Y., Osborne, A. R., Zimmer, J. & Rapoport, T. A. A role for the two-helix finger of the SecA ATPase in protein translocation. *Nature* 455, 984-987 (2008).
45. Martin, A., Baker, T. A. & Sauer, R. T. Pore loops of the AAA+ ClpX machine grip substrates to drive translocation and unfolding. *Nature Struct. Mol. Biol.* 15, 1147-1151 (2008).
46. Rehm, B. H. A. Alginate Production: Precursor Biosynthesis, Polymerization and Secretion. *Microbiology Monographs* 13, 55-71 (2009).
47. Itoh, Y., Rice, J. D., Goller, C., Pannuri, A., Taylor, J., Meisner, J., Beveridge, T. J., Preston, J. F. r. & Romeo, T. Roles of pgaABCD genes in synthesis, modification, and export of the *Escherichia coli* biofilm adhesin poly-beta-1,6-N-acetyl-D-glucosamine. *J. Bacteriol.* 190, 3670-3680 (2008).
48. Steiner, S., Lori, C., Boehm, A. & Jenal, U. Allosteric activation of exopolysaccharide synthesis through cyclic di-GMP-stimulated protein-protein interaction. *EMBO J.* 32, 354-368 (2013).
49. Keiski, C. L., Harwich, M., Jain, S., Neculai, A. M., Yip, P., Robinson, H., Whitney, J. C., Riley, L., Burrows, L. L., Ohman, D. E. & Howell, P. L. AlgK is a TPR-containing protein and the periplasmic component of a novel exopolysaccharide secretin. *Structure* 18, 265-273 (2010).
50. Karplus, P. A. & Diederichs, K. Linking crystallographic model and data quality. *Science* 336, 1030-1033 (2012).
51. Leslie, A. G. The integration of macromolecular diffraction data. *Acta Crystallogr. D Biol. Crystallogr.* 62, 48-57 (2006).
52. CCP4. The CCP4 suite: programs for protein crystallography. *Acta Crystallogr. D Biol. Crystallogr.* 50, 760-763 (1994).
53. McCoy, A. J., Grosse-Kunstleve, R. W., Adams, P. D., Winn, M. D., Storoni, L. C. & Read, R. J. Phaser crystallographic software. *J. Appl. Crystallogr.* 40, 658-674 (2007).
54. Vagin, A. & Teplyakov, A. Molecular replacement with MOLREP. *Acta Crystallogr. D Biol. Crystallogr.* 66, 22-25 (2010).
55. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C. & Zwart, P. H. PHENIX: a comprehensive Python-based system for macromolecular structure solution. *Acta Crystallogr. D Biol. Crystallogr.* 66, 213-221 (2010).
56. Cowtan, K. Recent developments in classical density modification. *Acta Crystallogr. D Biol. Crystallogr.* 66, 470-478 (2010).
57. Cowtan, K. D. & Zhang, K. Y. Density modification for macromolecular phase improvement. *Prog. Biophys. Mol. Biol.* 72, 245-270 (1999).
58. Emsley, P. & Cowtan, K. Coot: model-building tools for molecular graphics. *Acta Crystallogr. D Biol. Crystallogr.* 60, 2126-2132 (2004).
59. Terwilliger, T. C. Using prime-and-switch phasing to reduce model bias in molecular replacement. *Acta Crystallogr. D Biol. Crystallogr.* 60, 2144-2149 (2004).
60. Painter, J. TLSMD web server for the generation of multi-group TLS models. *J. Appl. Cryst.* 39, 109-111 (2006).
61. PyMol. The PYMOL Molecular Graphics System. *DeLano Scientific* (2000).
62. Ho, B. K. & Gruswitz, F. HOLLOW: generating accurate representations of channel and interior surfaces in molecular structures. *BMC Struct Biol* 8, 49 (2008).
63. Morin, A., Eisenbraun, B., Key, J., Sanschagrin, P. C., Timony, M. A., Ottaviano, M. & Sliz, P. Collaboration gets the most out of software. *Elife* 2, e01456 (2013).

What is claimed is:

1. A method for synthesizing cellulose In vitro using purified bacterial components, said method comprising adding purified bacterial cellulose synthase A (BcsA), or a biologically active fragment or homolog thereof, and purified bacterial cellulose synthase B (BcsB), or a biologically active fragment or homolog thereof, to a mixture of uridine diphosphate glucose (UDP-Glc) without lipid linked intermediates, a divalent cation, dimeric guanosine monophosphate (c-di-GMP) when the BcsA or a biologically active fragment or homolog thereof is not constitutively active, a membrane mimetic, and a physiologic buffer to form a mixture, wherein said BcsA and said BcsB are purified as a complex or said BcsA and said BcsB are purified separately, wherein said membrane mimetic is selected from the group consisting of a detergent micelle, lipid vesicle, and planar lipid bilayer, thereby synthesizing cellulose.

2. The method of claim 1, wherein said physiologic buffer has a pH of about 6.5 to about 9.5 and comprises 100 mM NaCl, about a 2 mM final concentration of UDP-Glc, and optionally about 10% glycerol as a protein stabilizer.

3. The method of claim 2, wherein said buffer has a pH of about 7.5.

4. The method of claim 1, wherein said mixture is incubated.

5. The method of claim 1, wherein said divalent cation is $Mn^{2+}$ or $Mg^{2+}$, further wherein said divalent cation is used at a concentration of 20 mM.

6. The method of claim 1, wherein said method is performed without added lipid-linked reactants.

7. The method of claim 1, wherein said active fragment of BcsB is selected from a group of fragments comprising amino acid residues 190-725, 309-725, 456-725, and 684-725 of SEQ ID NO:3 or the equivalent residues of SEQ ID NO:5 or other BcsB proteins.

8. The method of claim 1, wherein said BcsB or a biologically active fragment or homolog thereof mediates interaction with BcsA and maintains the catalytic activity of BcsA.

9. The method of claim 1, wherein said BcsB comprises an amino acid sequence having SEQ ID NOs:3, 4, or 5 or a biologically active fragment or homolog thereof.

10. The method of claim 1, wherein said BcsA comprises an amino acid sequence having SEQ ID NOs:1 or 2, or a biologically active fragment or homolog thereof.

11. The method of claim 10, wherein said BcsA, or a biologically active fragment or homolog thereof, comprises a mutation selected from the group consisting of a mutation at position 580 replacing arginine with alanine, a mutation at position 371 replacing glutamic acid with alanine, and mutations at position 580 replacing arginine with alanine and position 371 replacing glutamic acid with alanine.

12. The method of claim 11, wherein said mutation at position 580 confers constitutive catalytic activity on said BcsA, or a biologically active fragment or homolog thereof.

13. The method of claim 1, wherein said bacteria is *Rhodobacter sphaeroides* or *Escherichia coli*.

14. The method of claim 1, wherein said cellulose is high molecular weight cellulose.

15. The method of claim 14, wherein said cellulose comprises 1,4-linked glucosyl residues.

16. The method of claim 13, wherein said cellulose is useful for the synthesis of biofilms.

17. The method of claim 1, wherein said c-di-GMP is used at a final concentration of 0.3 μM and said UDP-glc is used at a final concentration of 2.0 mM.

18. The method of claim 1, wherein said method produces cellulose chains with a degree of polymerization is at least about 200.

19. The method of claim 1 wherein said method synthesizes cellulose in the absence of other synthase subunits.

20. The method of claim 1, wherein said BcsA and BcsB form a functional monomeric BcsA-BcsB cellulose synthase complex.

* * * * *

SEQUENCE LISTING

<160> NUMBER OF SEQ ID NOS: 5

<210> SEQ ID NO 1
<211> LENGTH: 788
<212> TYPE: PRT
<213> ORGANISM: Rhodobacter sphaeroides

<400> SEQUENCE: 1

```
Met Thr Val Arg Ala Lys Ala Arg Ser Pro Leu Arg Val Val Pro Val
1               5                   10                  15

Leu Leu Phe Leu Leu Trp Val Ala Leu Leu Val Pro Phe Gly Leu Leu
            20                  25                  30

Ala Ala Ala Pro Val Ala Pro Ser Ala Gln Gly Leu Ile Ala Leu Ser
            35                  40                  45

Ala Val Val Leu Val Ala Leu Leu Lys Pro Phe Ala Asp Lys Met Val
        50                  55                  60

Pro Arg Phe Leu Leu Leu Ser Ala Ala Ser Met Leu Val Met Arg Tyr
65                  70                  75                  80

Trp Phe Trp Arg Leu Phe Glu Thr Leu Pro Pro Ala Leu Asp Ala
                85                  90                  95

Ser Phe Leu Phe Ala Leu Leu Leu Phe Ala Val Glu Thr Phe Ser Ile
                100                 105                 110

Ser Ile Phe Phe Leu Asn Gly Phe Leu Ser Ala Asp Pro Thr Asp Arg
                115                 120                 125

Pro Phe Pro Arg Pro Leu Gln Pro Glu Glu Leu Pro Thr Val Asp Ile
            130                 135                 140

Leu Val Pro Ser Tyr Asn Glu Pro Ala Asp Met Leu Ser Val Thr Leu
145                 150                 155                 160

Ala Ala Ala Lys Asn Met Ile Tyr Pro Ala Arg Leu Arg Thr Val Val
                165                 170                 175

Leu Cys Asp Asp Gly Gly Thr Asp Gln Arg Cys Met Ser Pro Asp Pro
                180                 185                 190

Glu Leu Ala Gln Lys Ala Gln Glu Arg Arg Glu Leu Gln Gln Leu
            195                 200                 205

Cys Arg Glu Leu Gly Val Val Tyr Ser Thr Arg Glu Arg Asn Glu His
    210                 215                 220

Ala Lys Ala Gly Asn Met Ser Ala Ala Leu Glu Arg Leu Lys Gly Glu
225                 230                 235                 240

Leu Val Val Val Phe Asp Ala Asp His Val Pro Ser Arg Asp Phe Leu
                245                 250                 255

Ala Arg Thr Val Gly Tyr Phe Val Glu Asp Pro Asp Leu Phe Leu Val
                260                 265                 270

Gln Thr Pro His Phe Phe Ile Asn Pro Asp Pro Ile Gln Arg Asn Leu
            275                 280                 285

Ala Leu Gly Asp Arg Cys Pro Pro Glu Asn Glu Met Phe Tyr Gly Lys
            290                 295                 300

Ile His Arg Gly Leu Asp Arg Trp Gly Gly Ala Phe Phe Cys Gly Ser
305                 310                 315                 320

Ala Ala Val Leu Arg Arg Ala Leu Asp Glu Ala Gly Gly Phe Ala
                325                 330                 335

Gly Glu Thr Ile Thr Glu Asp Ala Glu Thr Ala Leu Glu Ile His Ser
                340                 345                 350

Arg Gly Trp Lys Ser Leu Tyr Ile Asp Arg Ala Met Ile Ala Gly Leu
            355                 360                 365
```

```
Gln Pro Glu Thr Phe Ala Ser Phe Ile Gln Gln Arg Gly Arg Trp Ala
    370                 375                 380
Thr Gly Met Met Gln Met Leu Leu Leu Lys Asn Pro Leu Phe Arg Arg
385                 390                 395                 400
Gly Leu Gly Ile Ala Gln Arg Leu Cys Tyr Leu Asn Ser Met Ser Phe
                405                 410                 415
Trp Phe Phe Pro Leu Val Arg Met Met Phe Leu Val Ala Pro Leu Ile
                420                 425                 430
Tyr Leu Phe Phe Gly Ile Glu Ile Phe Val Ala Thr Phe Glu Glu Val
                435                 440                 445
Leu Ala Tyr Met Pro Gly Tyr Leu Ala Val Ser Phe Leu Val Gln Asn
450                 455                 460
Ala Leu Phe Ala Arg Gln Arg Trp Pro Leu Val Ser Glu Val Tyr Glu
465                 470                 475                 480
Val Ala Gln Ala Pro Tyr Leu Ala Arg Ala Ile Val Thr Thr Leu Leu
                485                 490                 495
Arg Pro Arg Ser Ala Arg Phe Ala Val Thr Ala Lys Asp Glu Thr Leu
                500                 505                 510
Ser Glu Asn Tyr Ile Ser Pro Ile Tyr Arg Pro Leu Leu Phe Thr Phe
                515                 520                 525
Leu Leu Cys Leu Ser Gly Val Leu Ala Thr Leu Val Arg Trp Val Ala
530                 535                 540
Phe Pro Gly Asp Arg Ser Val Leu Leu Val Val Gly Gly Trp Ala Val
545                 550                 555                 560
Leu Asn Val Leu Leu Val Gly Phe Ala Leu Arg Ala Val Ala Glu Lys
                565                 570                 575
Gln Gln Arg Arg Ala Ala Pro Arg Val Gln Met Glu Val Pro Ala Glu
                580                 585                 590
Ala Gln Ile Pro Ala Phe Gly Asn Arg Ser Leu Thr Ala Thr Val Leu
                595                 600                 605
Asp Ala Ser Thr Ser Gly Val Arg Leu Leu Val Arg Leu Pro Gly Val
                610                 615                 620
Gly Asp Pro His Pro Ala Leu Glu Ala Gly Gly Leu Ile Gln Phe Gln
625                 630                 635                 640
Pro Lys Phe Pro Asp Ala Pro Gln Leu Glu Arg Met Val Arg Gly Arg
                645                 650                 655
Ile Arg Ser Ala Arg Arg Glu Gly Gly Thr Val Met Val Gly Val Ile
                660                 665                 670
Phe Glu Ala Gly Gln Pro Ile Ala Val Arg Glu Thr Val Ala Tyr Leu
                675                 680                 685
Ile Phe Gly Glu Ser Ala His Trp Arg Thr Met Arg Glu Ala Thr Met
                690                 695                 700
Arg Pro Ile Gly Leu Leu His Gly Met Ala Arg Ile Leu Trp Met Ala
705                 710                 715                 720
Ala Ala Ser Leu Pro Lys Thr Ala Arg Asp Phe Met Asp Glu Pro Ala
                725                 730                 735
Arg Arg Arg Arg Arg His Glu Glu Pro Lys Glu Lys Gln Ala His Leu
                740                 745                 750
Leu Ala Phe Gly Thr Asp Phe Ser Thr Glu Pro Asp Trp Ala Gly Glu
                755                 760                 765
Leu Leu Asp Pro Thr Ala Gln Val Ser Ala Arg Pro Asn Thr Val Ala
770                 775                 780
Trp Gly Ser Asn
```

-continued

785

<210> SEQ ID NO 2
<211> LENGTH: 803
<212> TYPE: PRT
<213> ORGANISM: Rhodobacter sphaeroides

<400> SEQUENCE: 2

```
Met Gly Thr Val Arg Ala Lys Ala Arg Ser Pro Leu Arg Val Val Pro
1               5                   10                  15

Val Leu Leu Phe Leu Leu Trp Val Ala Leu Leu Val Pro Phe Gly Leu
            20                  25                  30

Leu Ala Ala Ala Pro Val Ala Pro Ser Ala Gln Gly Leu Ile Ala Leu
        35                  40                  45

Ser Ala Val Val Leu Val Ala Leu Leu Lys Pro Phe Ala Asp Lys Met
    50                  55                  60

Val Pro Arg Phe Leu Leu Leu Ser Ala Ala Ser Met Leu Val Met Arg
65                  70                  75                  80

Tyr Trp Phe Trp Arg Leu Phe Glu Thr Leu Pro Pro Ala Leu Asp
                85                  90                  95

Ala Ser Phe Leu Phe Ala Leu Leu Leu Phe Ala Val Glu Thr Phe Ser
            100                 105                 110

Ile Ser Ile Phe Phe Leu Asn Gly Phe Leu Ser Ala Asp Pro Thr Asp
        115                 120                 125

Arg Pro Phe Pro Arg Pro Leu Gln Pro Glu Glu Leu Pro Thr Val Asp
    130                 135                 140

Ile Leu Val Pro Ser Tyr Asn Glu Pro Ala Asp Met Leu Ser Val Thr
145                 150                 155                 160

Leu Ala Ala Ala Lys Asn Met Ile Tyr Pro Ala Arg Leu Arg Thr Val
                165                 170                 175

Val Leu Cys Asp Asp Gly Gly Thr Asp Gln Arg Cys Met Ser Pro Asp
            180                 185                 190

Pro Glu Leu Ala Gln Lys Ala Gln Glu Arg Arg Glu Leu Gln Gln
        195                 200                 205

Leu Cys Arg Glu Leu Gly Val Val Tyr Ser Thr Arg Gly Arg Asn Glu
    210                 215                 220

His Ala Lys Ala Gly Asn Met Ser Ala Ala Leu Glu Arg Leu Lys Gly
225                 230                 235                 240

Glu Leu Val Val Val Phe Asp Ala Asp His Val Pro Ser Arg Asp Phe
                245                 250                 255

Leu Ala Arg Thr Val Gly Tyr Phe Val Glu Asp Pro Asp Leu Phe Leu
            260                 265                 270

Val Gln Thr Pro His Phe Phe Ile Asn Pro Asp Pro Ile Gln Arg Asn
        275                 280                 285

Leu Ala Leu Gly Asp Arg Cys Pro Pro Glu Asn Glu Met Phe Tyr Gly
    290                 295                 300

Lys Ile His Arg Gly Leu Asp Arg Trp Gly Ala Phe Phe Cys Gly
305                 310                 315                 320

Ser Ala Ala Val Leu Arg Arg Arg Ala Leu Asp Glu Ala Gly Gly Phe
                325                 330                 335

Ala Gly Glu Thr Ile Thr Glu Asp Ala Glu Thr Ala Leu Glu Ile His
            340                 345                 350

Ser Arg Gly Trp Lys Ser Leu Tyr Ile Asp Arg Ala Met Ile Ala Gly
        355                 360                 365
```

```
Leu Gln Pro Glu Thr Phe Ala Ser Phe Ile Gln Gln Arg Gly Arg Trp
    370                 375                 380

Ala Thr Gly Met Met Gln Met Leu Leu Leu Lys Asn Pro Leu Phe Arg
385                 390                 395                 400

Arg Gly Leu Gly Ile Ala Gln Arg Leu Cys Tyr Leu Asn Ser Met Ser
                405                 410                 415

Phe Trp Phe Phe Pro Leu Val Arg Met Met Phe Leu Val Ala Pro Leu
            420                 425                 430

Ile Tyr Leu Phe Phe Gly Ile Glu Ile Phe Val Ala Thr Phe Glu Glu
                435                 440                 445

Val Leu Ala Tyr Met Pro Gly Tyr Leu Ala Val Ser Phe Leu Val Gln
    450                 455                 460

Asn Ala Leu Phe Ala Arg Gln Arg Trp Pro Leu Val Ser Glu Val Tyr
465                 470                 475                 480

Glu Val Ala Gln Ala Pro Tyr Leu Ala Arg Ala Ile Val Thr Thr Leu
                485                 490                 495

Leu Arg Pro Arg Ser Ala Arg Phe Ala Val Thr Ala Lys Asp Glu Thr
            500                 505                 510

Leu Ser Glu Asn Tyr Ile Ser Pro Ile Tyr Arg Pro Leu Leu Phe Thr
                515                 520                 525

Phe Leu Leu Cys Leu Ser Gly Val Leu Ala Thr Leu Val Arg Trp Val
            530                 535                 540

Ala Phe Pro Gly Asp Arg Ser Val Leu Leu Val Val Gly Gly Trp Ala
545                 550                 555                 560

Val Leu Asn Val Leu Leu Val Gly Phe Ala Leu Arg Ala Val Ala Glu
                565                 570                 575

Lys Gln Gln Arg Arg Ala Ala Pro Arg Val Gln Met Glu Val Pro Ala
                580                 585                 590

Glu Ala Gln Ile Pro Ala Phe Gly Asn Arg Ser Leu Thr Ala Thr Val
                595                 600                 605

Leu Asp Ala Ser Thr Ser Gly Val Arg Leu Leu Val Arg Leu Pro Gly
    610                 615                 620

Val Gly Asp Pro His Pro Ala Leu Glu Ala Gly Gly Leu Ile Gln Phe
625                 630                 635                 640

Gln Pro Lys Phe Pro Asp Ala Pro Gln Leu Glu Arg Met Val Arg Gly
                645                 650                 655

Arg Ile Arg Ser Ala Arg Arg Glu Gly Gly Thr Val Met Val Gly Val
                660                 665                 670

Ile Phe Glu Ala Gly Gln Pro Ile Ala Val Arg Glu Thr Val Ala Tyr
                675                 680                 685

Leu Ile Phe Gly Glu Ser Ala His Trp Arg Thr Met Arg Glu Ala Thr
    690                 695                 700

Met Arg Pro Ile Gly Leu Leu His Gly Met Ala Arg Ile Leu Trp Met
705                 710                 715                 720

Ala Ala Ala Ser Leu Pro Lys Thr Ala Arg Asp Phe Met Asp Glu Pro
                725                 730                 735

Ala Arg Arg Arg Arg Arg His Glu Glu Pro Lys Glu Lys Gln Ala His
                740                 745                 750

Leu Leu Ala Phe Gly Thr Asp Phe Ser Thr Glu Pro Asp Trp Ala Gly
            755                 760                 765

Glu Leu Leu Asp Pro Thr Ala Gln Val Ser Ala Arg Pro Asn Thr Val
770                 775                 780

Ala Trp Gly Ser Asn His His His His His Lys Leu His His His
```

His His His

<210> SEQ ID NO 3
<211> LENGTH: 725
<212> TYPE: PRT
<213> ORGANISM: Rhodobacter sphaeroides

<400> SEQUENCE: 3

```
Met Asp Met Arg Leu Leu Pro Phe Leu Phe Leu Gly Thr Leu Ala Ser
1               5                   10                  15

Met Ala Ala Ala Gln Asp Ala Pro Met Ile Val Ile Glu Gly Leu Thr
            20                  25                  30

Ser Glu Glu Pro Gln Ala Ser Pro Asp Ala Val Ala Glu Ala Val Pro
        35                  40                  45

Ala Ala Glu Val Ala Pro Trp Ile Ile Pro Leu Arg Pro Leu Ala Glu
    50                  55                  60

Thr Ala Gln Val Gly Pro Leu Phe Arg Leu Gln Gly Gln Gln Ala Arg
65                  70                  75                  80

Ala Ala Phe Arg Leu Phe Leu Pro Thr Glu Ala Val Gly Gly Thr Leu
                85                  90                  95

Thr Leu Ala Gln Arg Ser Ser Ile Asp Ile Leu Pro Glu Ser Ser Gln
            100                 105                 110

Ile Ile Val Arg Met Asn Asp Gln Glu Ile Gly Arg Phe Thr Pro Arg
        115                 120                 125

Gln Phe Gly Ala Leu Gly Ala Val Thr Met Pro Leu Gly Glu Ala Val
    130                 135                 140

Arg Ala Gly Asp Asn Leu Val Thr Ile Glu Ala Gln His Arg His Arg
145                 150                 155                 160

Ile Tyr Cys Gly Ala Asp Ala Glu Phe Asp Leu Trp Thr Glu Val Asp
                165                 170                 175

Leu Ser Gln Ser Gly Val Ala Leu Pro Ala Ala Ile Gly Thr Glu
            180                 185                 190

Pro Thr Ser Phe Ile Ala Ala Leu Thr Ala Gln Ala Glu Ser Gly Arg
        195                 200                 205

Pro Val Glu Ile Arg Thr Pro Thr Pro Asp Glu Ala Thr Leu Arg
    210                 215                 220

Thr Leu Ala Gln Ala Leu Gly Arg Pro Leu Pro Asp Glu Ala Leu Pro
225                 230                 235                 240

Leu Ala Leu Ser Lys Pro Trp Ser Ala Glu Thr Gly Pro Thr Tyr Ala
                245                 250                 255

Arg Ile Thr Leu Leu Pro Ser Asp Ala Asp Arg Val Ser Ile Arg Arg
            260                 265                 270

Gly Gly Asp Gly Ala Val Val Leu Val Leu Glu His Pro Pro Glu Gly
        275                 280                 285

Ser Pro Asn Ala Ser Leu Val Ala Asp Leu Leu Gly Ala Thr Pro Thr
    290                 295                 300

Leu Pro Pro Pro Thr Leu Pro Gln Ile Pro Pro Gly Arg Val Val Thr
305                 310                 315                 320

Leu Ala Asp Met Gly Val Asp Thr Ile Leu Thr Asp Asn Arg Tyr Phe
                325                 330                 335

Asn Arg Asp Ile Asp Phe Gln Leu Pro Asp Asp Trp Leu Leu Leu Ala
            340                 345                 350

Ser Gln Lys Ala Gln Ile Gly Ile Asp Tyr Gly Phe Ala Gly Gly Leu
```

```
                355                 360                 365
Pro Glu Gly Ala Leu Leu Val Lys Val Asn Gly Thr Thr Val Arg
    370                 375                 380

Met Leu Pro Leu Asp Arg Asp Ala Ala Pro Val Lys Pro Arg Leu Asp
385                 390                 395                 400

Ile Arg Phe Pro Ala Arg Leu Leu His Pro Gly Pro Asn Arg Leu Ser
                405                 410                 415

Phe Glu Ser Val Ile Pro Gly Asn Pro Pro Asp Gln Pro Cys Pro Ala
            420                 425                 430

Ser Ala Gly Asp Leu Met Gln Val Leu Ser Ser Thr Asp Leu Glu Val
        435                 440                 445

Pro Pro Ser Pro Arg Met Gln Met Ala Asp Met Ala Arg Asp Leu Ala
    450                 455                 460

Gln Val Thr Pro Ala Ser Val His Pro Ala Thr Pro Asp Gly Leu Ala
465                 470                 475                 480

Arg Thr Leu Pro Phe Met Ala Ala Phe Arg Glu Val Pro Asp Ala Ala
                485                 490                 495

Pro Val Asp Leu Thr Val Ala Gly Leu His Asp Ile Ala Thr Val Pro
            500                 505                 510

Leu Asn Glu Glu Gly Leu Thr Pro Arg Leu Leu Ala Leu Thr Leu Leu
        515                 520                 525

Pro Ser Thr Val Ser Arg Leu Val Glu Arg Pro Ala Thr Pro Ala Gly
    530                 535                 540

Pro Pro Ala Asn Ala Leu Ala Pro Leu Gly Ala Ala Pro Gly Glu Gly
545                 550                 555                 560

Val Met Pro Pro Leu Val Glu Ser Asn Trp Ser Asp Arg Ala Gln Thr
                565                 570                 575

Phe Val Gln Ala Thr Leu Gln Pro Val Ile Gln Thr Val Arg Arg Met
            580                 585                 590

Leu Arg Pro Gly Asp Gly Asn Leu Ala Glu Trp Leu Ala Thr Arg Lys
        595                 600                 605

Gly Thr Ala Met Leu Leu Ala Pro Glu Pro Gly Lys Leu Trp Val Ile
    610                 615                 620

Leu Gly Pro Glu Ala Glu Pro Ala Arg Val Ala Glu Ala Leu Ala Met
625                 630                 635                 640

Ala Pro Arg Ser Pro Gly Gly Pro Arg Gly Gln Val Ala Val Leu Gly
                645                 650                 655

Ser Asp Gly Arg Trp Ser Ser Trp Ser Lys Pro Gly Leu Leu Pro Glu
            660                 665                 670

Leu Arg Glu Pro Val Ser Leu Asp Asn Val Arg Ser Val Val Gly Asn
        675                 680                 685

Val Ala Ser Ala Arg Pro Pro Leu Leu Leu Gly Met Leu Gly Leu
    690                 695                 700

Ala Trp Ile Ser Ala Ala Ile Ala Val Gly Phe Val Leu Arg Thr Arg
705                 710                 715                 720

Arg Lys Gly Leu Lys
            725

<210> SEQ ID NO 4
<211> LENGTH: 42
<212> TYPE: PRT
<213> ORGANISM: Rhodobacter sphaeroides

<400> SEQUENCE: 4
```

-continued

```
Ser Val Val Gly Asn Val Ala Ser Ala Arg Pro Pro Leu Leu Leu Gly
1               5                   10                  15
Gly Met Leu Gly Leu Ala Trp Ile Ser Ala Ala Ile Ala Val Gly Phe
            20                  25                  30
Val Leu Arg Thr Arg Arg Lys Gly Leu Lys
        35                  40
```

<210> SEQ ID NO 5
<211> LENGTH: 729
<212> TYPE: PRT
<213> ORGANISM: Artificial Sequence
<220> FEATURE:
<223> OTHER INFORMATION: Hybrid between E. Coli and Rhodobacter
      sphaeroides

<400> SEQUENCE: 5

```
Met Lys Tyr Leu Leu Pro Thr Ala Ala Ala Gly Leu Leu Leu Leu Ala
1               5                   10                  15
Ala Gln Pro Ala Met Ala Met Gly Gln Asp Ala Pro Met Ile Val Ile
            20                  25                  30
Glu Gly Leu Thr Ser Glu Glu Pro Gln Ala Ser Pro Asp Ala Val Ala
            35                  40                  45
Glu Ala Val Pro Ala Ala Glu Val Ala Pro Trp Ile Ile Pro Leu Arg
50                  55                  60
Pro Leu Ala Glu Thr Ala Gln Val Gly Pro Leu Phe Arg Leu Gln Gly
65                  70                  75                  80
Gln Gln Ala Arg Ala Ala Phe Arg Leu Phe Leu Pro Thr Glu Ala Val
            85                  90                  95
Gly Gly Thr Leu Thr Leu Ala Gln Arg Ser Ser Ile Asp Ile Leu Pro
            100                 105                 110
Glu Ser Ser Gln Ile Ile Val Arg Met Asn Asp Gln Glu Ile Gly Arg
            115                 120                 125
Phe Thr Pro Arg Gln Phe Gly Ala Leu Gly Ala Val Thr Met Pro Leu
        130                 135                 140
Gly Glu Ala Val Arg Ala Gly Asp Asn Leu Val Thr Ile Glu Ala Gln
145                 150                 155                 160
His Arg His Arg Ile Tyr Cys Gly Ala Asp Ala Glu Phe Asp Leu Trp
                165                 170                 175
Thr Glu Val Asp Leu Ser Gln Ser Gly Val Ala Leu Pro Ala Ala Ala
            180                 185                 190
Ile Gly Thr Glu Pro Thr Ser Phe Ile Ala Ala Leu Thr Ala Gln Ala
            195                 200                 205
Glu Ser Gly Arg Pro Val Glu Ile Arg Thr Pro Thr Pro Asp Glu
        210                 215                 220
Ala Thr Leu Arg Thr Leu Ala Gln Ala Leu Gly Arg Pro Leu Pro Asp
225                 230                 235                 240
Glu Ala Leu Pro Leu Ala Leu Ser Lys Pro Trp Ser Ala Glu Thr Gly
            245                 250                 255
Pro Thr Tyr Ala Arg Ile Thr Leu Leu Pro Ser Asp Ala Asp Arg Val
            260                 265                 270
Ser Ile Arg Arg Gly Gly Asp Gly Ala Val Val Leu Val Leu Glu His
        275                 280                 285
Pro Pro Glu Gly Ser Pro Asn Ala Ser Leu Val Ala Asp Leu Leu Gly
        290                 295                 300
Ala Thr Pro Thr Leu Pro Pro Thr Leu Pro Gln Ile Pro Pro Gly
305                 310                 315                 320
```

```
Arg Val Val Thr Leu Ala Asp Met Gly Val Asp Thr Ile Leu Thr Asp
                325                 330                 335

Asn Arg Tyr Phe Asn Arg Asp Ile Asp Phe Gln Leu Pro Asp Asp Trp
            340                 345                 350

Leu Leu Leu Ala Ser Gln Lys Ala Gln Ile Gly Ile Asp Tyr Gly Phe
            355                 360                 365

Ala Gly Gly Leu Pro Glu Gly Ala Leu Leu Val Lys Val Asn Gly
        370                 375                 380

Thr Thr Val Arg Met Leu Pro Leu Asp Arg Asp Ala Ala Pro Val Lys
385                 390                 395                 400

Pro Arg Leu Asp Ile Arg Phe Pro Ala Arg Leu Leu His Pro Gly Pro
                405                 410                 415

Asn Arg Leu Ser Phe Glu Ser Val Ile Pro Gly Asn Pro Pro Asp Gln
            420                 425                 430

Pro Cys Pro Ala Ser Ala Gly Asp Leu Met Gln Val Leu Ser Ser Thr
        435                 440                 445

Asp Leu Glu Val Pro Pro Ser Pro Arg Met Gln Met Ala Asp Met Ala
        450                 455                 460

Arg Asp Leu Ala Gln Val Thr Pro Ala Ser Val His Pro Ala Thr Pro
465                 470                 475                 480

Asp Gly Leu Ala Arg Thr Leu Pro Phe Met Ala Ala Phe Arg Glu Val
                485                 490                 495

Pro Asp Ala Ala Pro Val Asp Leu Thr Val Ala Gly Leu His Asp Ile
            500                 505                 510

Ala Thr Val Pro Leu Asn Glu Glu Gly Leu Thr Pro Arg Leu Leu Ala
            515                 520                 525

Leu Thr Leu Leu Pro Ser Thr Val Ser Arg Leu Val Glu Arg Pro Ala
        530                 535                 540

Thr Pro Ala Gly Pro Ala Asn Ala Leu Ala Pro Leu Gly Ala Ala
545                 550                 555                 560

Pro Gly Glu Gly Val Met Pro Pro Leu Val Glu Ser Asn Trp Ser Asp
                565                 570                 575

Arg Ala Gln Thr Phe Val Gln Ala Thr Leu Gln Pro Val Ile Gln Thr
            580                 585                 590

Val Arg Arg Met Leu Arg Pro Gly Asp Gly Asn Leu Ala Glu Trp Leu
        595                 600                 605

Ala Thr Arg Lys Gly Thr Ala Met Leu Leu Ala Pro Glu Pro Gly Lys
610                 615                 620

Leu Trp Val Ile Leu Gly Pro Glu Ala Glu Pro Ala Arg Val Ala Glu
625                 630                 635                 640

Ala Leu Ala Met Ala Pro Arg Ser Pro Gly Gly Pro Arg Gly Gln Val
                645                 650                 655

Ala Val Leu Gly Ser Asp Gly Arg Trp Ser Ser Trp Ser Lys Pro Gly
            660                 665                 670

Leu Leu Pro Glu Leu Arg Glu Pro Val Ser Leu Asp Asn Val Arg Ser
        675                 680                 685

Val Val Gly Asn Val Ala Ser Ala Arg Pro Leu Leu Leu Gly Gly
        690                 695                 700

Met Leu Gly Leu Ala Trp Ile Ser Ala Ala Ile Ala Val Gly Phe Val
705                 710                 715                 720

Leu Arg Thr Arg Arg Lys Gly Leu Lys
                725
```